(12) United States Patent
Schnable et al.

(10) Patent No.: US 12,336,472 B2
(45) Date of Patent: Jun. 24, 2025

(54) HIGHER-YIELDING PROSO

(71) Applicant: Dryland Genetics, Inc., Ames, IA (US)

(72) Inventors: Patrick S. Schnable, Ames, IA (US);
James C. Schnable, Lincoln, NE (US);
Santosh Rajput, Ames, IA (US)

(73) Assignee: Dryland Genetics, Inc., Ames, IA (US)

( * ) Notice: Subject to any disclaimer, the term of this patent is extended or adjusted under 35 U.S.C. 154(b) by 0 days.

(21) Appl. No.: 18/441,777

(22) Filed: Feb. 14, 2024

(65) Prior Publication Data
US 2024/0215510 A1 Jul. 4, 2024

Related U.S. Application Data

(63) Continuation of application No. 17/545,028, filed on Dec. 8, 2021, now Pat. No. 12,016,285.

(60) Provisional application No. 63/122,979, filed on Dec. 9, 2020.

(51) Int. Cl.
*A01H 6/46* (2018.01)
*A01H 5/10* (2018.01)

(52) U.S. Cl.
CPC ............. *A01H 6/4642* (2018.05); *A01H 5/10* (2013.01)

(58) Field of Classification Search
CPC .................................................. A01H 6/4642
See application file for complete search history.

(56) References Cited

U.S. PATENT DOCUMENTS

| 9,951,384 B2 | 4/2018 | Schnable et al. |
| 10,704,091 B2 | 7/2020 | Schnable et al. |

OTHER PUBLICATIONS

Santra, Dipak K. NebGuide No. G2219 University of Nebraska-Lincoln Extension, Institute of Agriculture and Natural Resources (Year: 2013).*
Cho et al., Development and characterization of twenty-five new polymorphic microsatellite markers in proso millet (Panicum miliaceum L.). Genes Genomics. 2010; 32: 267-73.
Colosi et al., Wild proso millet (Panicum miliaceum) is genetically variable and distinct from crop varieties of proso millet. Weed Sci. 1997. 45: 509-18.
Corpet. Multiple sequence alignment with hierarchical clustering. Nucleic Acids Res. Nov. 25, 1988;16(22):10881-90.
Dvořáková et al., Comparative analysis of genetic diversity of 8 millet genera revealed by ISSR markers. Emirates J. Food Agric. 2015; 27: 617-28.
He et al., Genotyping-by-sequencing (GBS), an ultimate marker-assisted selection (MAS) tool to accelerate plant breeding. Front Plant Sci. Sep. 30, 2014;5:484. 1-8.
Hu et al., Assessment of genetic diversity in broomcorn millet (Panicum miliaceum L.) using SSR markers. J Genet Genomics. Aug. 2009;36(8):491-500.
Hunt et al., Genetic diversity and phylogeography of broomcorn millet (Panicum miliaceum L.) across Eurasia. Mol Ecol. Nov. 2011;20(22):4756-71.
Hunt et al., Molecular basis of the waxy endosperm starch phenotype in broomcorn millet (Panicum miliaceum L.) Mol Biol Evol. Jul. 2010;27(7):1478-94.
Karam et al., Assessment of silver-stained AFLP markers for studying DNA polymorphism in proso millet (Panicum miliaceum L.). Rev. Brasil Bot. 2006; 29: 609-15.
Karam et al., Genetic diversity among proso millet (Panicum miliaceum) biotypes assessed by AFLP techniques. Planta Daninha. 2004; 22: 167-74.
Kumar et al., MEGA2: molecular evolutionary genetics analysis software. Bioinformatics. Dec. 2001;17(12):1244-5.
Lágler et al., Morphological and molecular analysis of common millet (P. miliaceum) cultivars compared to a DNA sample from the 15th century (Hungary). Euphytica. 2005; 146: 77-85.
M'Ribu et al., Detection of interspecific and intraspecific variation in Panicum millets through random amplified polymorphic DNA. Theor Appl Genet. Jun. 1994;88(3-4):412-6.
Needleman et al., A general method applicable to the search for similarities in the amino acid sequence of two proteins. J Mol Biol. Mar. 1970;48(3):443-53.
Nei et al., Mathematical model for studying genetic variation in terms of restriction endonucleases. Proc Natl Acad Sci U S A. Oct. 1979;76(10):5269-73.
Nielsen et al., Water use and environmental parameters influence proso millet yield. Field Crops Research. 2017; 212: 34-44.
Ott et al., Linked read technology for assembling large complex and polyploid genomes. BMC Genomics. Sep. 4, 2018;19(1):651. 15 pages.
Pearson et al., Improved tools for biological sequence comparison. Proc Natl Acad Sci U S A. Apr. 1988;85(8):2444-8.
Rajput et al., Development and characterization of SSR markers in proso millet (Panicum miliaceum L.) based on switchgrass genomics. Am. J. Plant Sci. 2014; 5: 175-86.
Rajput et al., Evaluation of genetic diversity of proso millet germplasm available in the United States using simple-sequence repeat markers. Crop Sci. 2016; 56: 2401-2409.
Smith et al., Comparison of biosequences. Adv. Appl. Math. 1981; 2:482-489.

(Continued)

*Primary Examiner* — David H Kruse
(74) *Attorney, Agent, or Firm* — Casimir Jones, S.C.; Thomas A. Isenbarger

(57) ABSTRACT

Several Proso cultivars are disclosed having improved yields. The technology relates to the seeds, plants, and plant parts of Proso cultivars; and further provides methods for producing progeny of Proso cultivars. The technology also relates to Proso cultivars or breeding cultivars, and plant parts derived from Proso cultivars; and to methods for producing other Proso cultivars, lines, or plant parts derived from Proso cultivars, and to the Proso plants, varieties, and their parts derived from use of those methods. The technology further relates to hybrid Proso seeds, plants, and plant parts produced by crossing improved-yield Proso cultivars with another Proso cultivar.

16 Claims, 4 Drawing Sheets

(56) References Cited

OTHER PUBLICATIONS

Thompson et al., The CLUSTAL_X windows interface: flexible strategies for multiple sequence alignment aided by quality analysis tools. Nucleic Acids Res. Dec. 15, 1997;25(24):4876-82.

Trivedi et al., Genetic variability in proso millet (Panicum miliaceum) germplasm of Central Himalayan Region based on morpho-physiological traits and molecular markers. Acta Physiol. Plant. 2015. 37(2): 23-38.

Zou et al., The genome of broomcorn millet. Nat Commun. Jan. 25, 2019;10(1):436. 1-11.

Baltensperger et al. Registration of "Huntsman" Proso Millet. Crop Science, 1995; 35(3), p. 941.

* cited by examiner

HIGHER-YIELDING PROSO

CROSS-REFERENCE TO RELATED APPLICATIONS

This application is a continuation of U.S. patent application Ser. No. 17/545,028, filed Dec. 8, 2021, which claims the benefit of U.S. Provisional Patent Application No. 63/122,979, filed Dec. 9, 2020, each of which is incorporated by reference herein in its entirety.

LENGTHY TABLE

The specification includes a lengthy table submitted via Patent Center in electronic format, titled "Proso_SNP_table", created Feb. 14, 2024, having the file size of 593,010 bytes, is hereby incorporated by reference in its entirety.

LENGTHY TABLES

The patent contains a lengthy table section. A copy of the table is available in electronic form from the USPTO web site (https://seqdata.uspto.gov/?pageRequest=docDetail&DocID=US12336472B2). An electronic copy of the table will also be available from the USPTO upon request and payment of the fee set forth in 37 CFR 1.19(b)(3).

FIELD

Provided herein is technology relating to plants and particularly, but not exclusively, to varieties of Proso (proso millet, *Panicum miliaceum*) with improved yields and methods and systems for improving the yield of Proso varieties and producing higher-yielding Proso varieties.

BACKGROUND

World production of the three major grain crops (corn, wheat, and rice) has more than tripled over the last fifty years. This rapid growth in production has been necessary to keep pace with increasing demand for grain from a growing world population, changing dietary preferences that require more grain to produce more meat, and production of grain-based biofuels. While increases in productivity per acre increased from 1960 to 2002, subsequent increases in productivity per acre and thus present crop production have failed to satisfy the increasing demand for grain. Increasing world population and limits on crop production due to climate change-induced changes in rainfall patterns, reduced availability of irrigation water, and a reduced supply of suitable farmland for crops are expected to create an increased demand for food and increased crop prices worldwide.

SUMMARY

In particular, inadequate supplies of freshwater have increased the risk of crop failures and food shortages worldwide. For example, fresh water is becoming increasingly limited as underground aquifers are depleted and expanding cities use water supplies previously reserved for agriculture. Furthermore, the increased variability in annual rainfall driven by global climate change has increased the risk of crop failure for non-irrigated farmland.

Accordingly, provided herein are varieties of Proso (proso millet, *Panicum miliaceum*), e.g., DLG40, DLG148, DLG149, and/or DLG240 as described herein that have improved yields, e.g., the technology provides a higher-yielding Proso. During the development of embodiments of the technology provided herein, diverse Proso germplasm (e.g., varieties) were collected. Further, during the development of embodiments of the technology provided herein, experiments were conducted to cross the collected germplasm (e.g., in a greenhouse or in a controlled plant growth facility (e.g., a growth room without windows and in which light is provided by light emitting diodes)). In some embodiments, breeding comprises crossing, collecting tissue samples (e.g., for DNA analyses), collecting plant phenotype data, and producing seed. During the development of embodiments of the technology described herein, phenotype data (e.g., seed weight, plant height and panicle architecture, and seed head shattering) linked to agronomical quality and yield were collected from measurements of plants, e.g., plants grown using controlled conditions (e.g., in a greenhouse, in a controlled plant growth facility (e.g., a growth room without windows and in which light is provided by light emitting diodes), etc.) and/or in a field. During the development of embodiments of the technology described herein, genotype and/or genomic data were collected from plants grown under controlled conditions and/or in a field.

In some embodiments, genotype and/or genomic analysis comprises analyzing a nucleic acid from a plant or a plant part (e.g., a plant grown using controlled conditions (e.g., in a greenhouse, in a growth room, etc.) and/or in a field). In some embodiments, genotype and/or genomic analysis comprises analysis of one or more polymorphic markers, e.g., one or more of amplified fragment length polymorphism (AFLP), random amplified polymorphic DNA (RAPD), cleaved amplified polymorphic DNA (CAP), inter simple sequence repeat (ISSR), sequence related amplified polymorphism (SRAP), and/or simple sequence repeat (SSR). In some embodiments, genotype and/or genomic analysis comprises determining a partial or whole genome sequence of a Proso variety, e.g., a partial or whole genome sequence of one or more nucleic acids, e.g., one or more chromosomes, genes, alleles, loci, or fragment of any of the foregoing. In some embodiments, genotype and/or genomic analysis comprises use of a genetic linkage maps of Proso. In some embodiments, genotype and/or genomic analysis comprises determining a nucleotide present at one or more SNP marker positions. In some embodiments, DNA analyses comprises genotyping, e.g., using a genotyping-by-sequencing technology. In some embodiments, SNP markers are identified using genotyping-by-sequencing (GBS) (see, e.g., He (2014) "Genotyping-by-sequencing (GBS), an ultimate marker assisted (MAS) tool to accelerate plant breeding" Front. Plant Sci. 5:484, incorporated herein by reference) or tunable genotyping-by-sequencing (see, e.g., U.S. Pat. Nos. 9,951,384 and 10,704,091, each of which is incorporated herein by reference). In some embodiments, genotype data is integrated (e.g., using statistical analysis) with phenotype data to determine (e.g., select and/or identify) plants having potential to exhibit high productivity (e.g., under field conditions). In some embodiments, statistical analyses are used to guide breeding decisions.

In some embodiments, the technology provided herein relates to new plant cultivars, e.g., new Proso cultivars (e.g., new higher-yielding Proso cultivars). Accordingly, in some embodiments, the technology relates to seeds of a Proso cultivar; plants of a Proso cultivar; and methods for producing a Proso plant comprising crossing Proso cultivar with itself or another Proso cultivar. In some embodiments, the technology relates to producing Proso variants by mutagenesis or transformation of a Proso cultivar.

For example, in some embodiments, the technology provided herein relates to new plant cultivars, e.g., new Proso cultivars. In some embodiments, the technology relates to one or more Proso cultivars that is/are Proso cultivar(s) DLG40, DLG148, DLG149, and/or DLG240 as described herein. Accordingly, in some embodiments, the technology relates to seeds of Proso cultivar DLG40, DLG148, DLG149, and/or DLG240; plants of Proso cultivar DLG40, DLG148, DLG149, and/or DLG240; and methods for producing a Proso plant comprising crossing Proso cultivar DLG40, DLG148, DLG149, and/or DLG240 with itself or another Proso cultivar. In some embodiments, the technology relates to producing Proso variants by mutagenesis or transformation of Proso cultivar DLG40, DLG148, DLG149, and/or DLG240.

In some embodiments, the technology relates to methods for introgressing a transgenic or mutant trait into Proso cultivar DLG40, DLG148, DLG149, and/or DLG240 and to the Proso plants and plant parts produced by those methods. In some embodiments, the technology also relates to Proso cultivars or breeding cultivars and plant parts derived from Proso cultivar DLG40, DLG148, DLG149, and/or DLG240; to methods for producing other Proso cultivars or plant parts derived from Proso cultivar DLG40, DLG148, DLG149, and/or DLG240; and to the Proso plants, varieties, and their parts derived from the use of those methods. In some embodiments, the technology relates to Proso seeds, plants, and plant parts produced by crossing Proso cultivar DLG40, DLG148, DLG149, and/or DLG240 with another Proso cultivar. Thus, the technology comprises any such methods using the Proso cultivar DLG40, DLG148, DLG149, and/or DLG240, e.g., for selfing, backcrossing, producing hybrids, crossing to populations, and the like. The technology includes all plants produced using Proso cultivar DLG40, DLG148, DLG149, and/or DLG240 as at least one parent. Moreover, in some embodiments, the Proso cultivar find use in crosses with other Proso plants to produce first generation ($F_1$) Proso hybrid seeds and plants with superior characteristics.

In some embodiments, the technology relates to regenerable cells for use in tissue culture of Proso cultivar DLG40, DLG148, DLG149, and/or DLG240. In some embodiments, the tissue culture is capable of regenerating plants having all the morphological and physiological characteristics of the foregoing Proso plant(s), and of regenerating plants having substantially the same genotype as the foregoing Proso plant(s). In some embodiments, the regenerable cells in tissue cultures are embryos, protoplasts, meristematic cells, callus, pollen, leaves, ovules, anthers, cotyledons, hypocotyl, pistils, roots, root tips, flowers, seeds, petiole, pods, or stems. In some embodiments, the present technology provides Proso plants regenerated from tissue cultures.

For example, in some embodiments, the technology provides a plant of Proso cultivar DLG40, representative seed of the Proso cultivar having been deposited under ATCC Accession No. PTA-127821 on Sep. 19, 2024, with the American Type Culture Collection, 10801 University Boulevard, Manassas, Virginia 20110. In some embodiments, the technology provides a seed that produces the plant of Proso cultivar DLG40. In some embodiments, the technology provides a cell of the plant of Proso cultivar DLG40. In some embodiments, the technology provides a tissue culture of regenerable cells comprising a cell of the plant of Proso cultivar DLG40.

In some embodiments, the technology provides a method of Proso breeding. For example, in some embodiments, the method comprises crossing the plant of Proso cultivar DLG40 with itself or a second Proso plant to produce Proso seed. In some embodiments, the method comprises crossing a plant of Proso cultivar DLG40 with a second Proso plant of a different genotype to produce hybrid Proso seed. In some embodiments, the method further comprises: (a) crossing a plant grown from the hybrid Proso seed with itself or a different Proso plant to produce a seed of a progeny plant of a subsequent generation. In some embodiments, the method further comprises (b) growing a progeny plant of a subsequent generation from the seed of a progeny plant of a subsequent generation and crossing the progeny plant of a subsequent generation with itself or a second plant to produce a progeny plant of a further subsequent generation. In some embodiments, the method further comprises (c) repeating steps (a) and (b) using the progeny plant of a further subsequent generation from step (b) in place of the plant grown from the hybrid Proso seed in step (a), wherein steps (a) and (b) are repeated with sufficient inbreeding to produce an inbred Proso plant derived from the Proso cultivar DLG40. In some embodiments, the technology provides an $F_1$ hybrid Proso seed produced by the method of Proso breeding.

In some embodiments, the technology provides a method of producing a plant comprising an added desired trait, the method comprising introducing a transgene conferring the desired trait into the plant of Proso cultivar DLG40. In some embodiments, the desired trait is selected from the group consisting of male sterility, herbicide tolerance, insect or pest resistance, disease resistance, modified fatty acid metabolism, altered water efficiency, altered nitrogen efficiency, altered protein quantity, modified protein composition, altered oil quantity, modified oil composition, altered starch quantity, modified starch composition, and modified carbohydrate metabolism. In some embodiments, the technology provides a plant or a selfed progeny thereof, wherein the plant or selfed progeny thereof comprises the transgene and otherwise comprises all of the morphological and physiological characteristics of Proso cultivar DLG40.

In some embodiments, the technology provides a method of introducing a locus conversion into a Proso plant. For example, in some embodiments, the method comprises: (a) crossing a plant of Proso cultivar DLG40 with a second plant comprising a desired locus to produce $F_1$ progeny plants, representative seed of the Proso cultivar DLG40 having been deposited under ATCC Accession No. PTA-127821 on Sep. 19, 2024, with the American Type Culture Collection, 10801 University Boulevard, Manassas, Virginia 20110; (b) selecting at least a first progeny plant from step (a) that comprises the locus to produce a selected progeny plant; (c) crossing the selected progeny plant from step (b) with a plant of Proso cultivar DLG40 to produce at least a first backcross progeny plant that comprises the locus; and (d) repeating steps (b) and (c) with the first backcross progeny plant produced from step (c) used in place of the first progeny plant of step (b) during the repeating, wherein steps (b) and (c) are repeated until at least a backcross progeny plant is produced comprising the locus conversion. In some embodiments, the locus confers a trait selected from the group consisting of male sterility, herbicide tolerance, insect or pest resistance, disease resistance, modified fatty acid metabolism, altered water efficiency, altered nitrogen efficiency, altered protein quantity, modified protein composition, altered oil quantity, modified oil composition, altered starch quantity, modified starch composition, abiotic stress resistance, and modified carbohydrate metabolism.

In some embodiments, the technology provides a Proso plant of Proso cultivar DLG40, further comprising a locus conversion, wherein the plant comprises the locus conversion and otherwise comprises all of the morphological and physiological characteristics of Proso cultivar DLG40, representative seed of Proso cultivar DLG40 having been deposited under ATCC Accession No. PTA-127821 on Sep. 19, 2024, with the American Type Culture Collection, 10801 University Boulevard, Manassas, Virginia 20110.

In some embodiments, the technology provides a method of introducing a mutation into the genome of Proso cultivar DLG40, the method comprising applying a mutagen to the plant of claim 1, or a part thereof, wherein the resulting plant comprises a genome mutation. In some embodiments, the mutagen is selected from the group consisting of ethyl methanesulfonate, gamma-rays, and sodium azide.

In some embodiments, the technology provides a method of producing a commodity plant product, the method comprising obtaining a Proso plant of Proso cultivar DLG40 or a part thereof and producing the commodity plant product therefrom. In some embodiments, the commodity plant product is seed, meal, flour, protein, or oil.

In addition, in some embodiments, the technology provides a plant of Proso cultivar DLG240. In some embodiments, the technology provides a seed that produces the plant of Proso cultivar DLG240. In some embodiments, the technology provides a cell of the plant of Proso cultivar DLG240. In some embodiments, the technology provides a tissue culture of regenerable cells comprising a cell of the plant of Proso cultivar DLG240.

In some embodiments, the technology provides a method of Proso breeding. For example, in some embodiments, the method comprises crossing the plant of Proso cultivar DLG240 with itself or a second Proso plant to produce Proso seed. In some embodiments, the method comprises crossing a plant of Proso cultivar DLG240 with a second Proso plant of a different genotype to produce hybrid Proso seed. In some embodiments, the method further comprises: (a) crossing a plant grown from the hybrid Proso seed with itself or a different Proso plant to produce a seed of a progeny plant of a subsequent generation. In some embodiments, the method further comprises (b) growing a progeny plant of a subsequent generation from the seed of a progeny plant of a subsequent generation and crossing the progeny plant of a subsequent generation with itself or a second plant to produce a progeny plant of a further subsequent generation. In some embodiments, the method further comprises (c) repeating steps (a) and (b) using the progeny plant of a further subsequent generation from step (b) in place of the plant grown from the hybrid Proso seed in step (a), wherein steps (a) and (b) are repeated with sufficient inbreeding to produce an inbred Proso plant derived from the Proso cultivar DLG240. In some embodiments, the technology provides an $F_1$ hybrid Proso seed produced by the method of Proso breeding.

In some embodiments, the technology provides a method of producing a plant comprising an added desired trait, the method comprising introducing a transgene conferring the desired trait into the plant of Proso cultivar DLG240. In some embodiments, the desired trait is selected from the group consisting of male sterility, herbicide tolerance, insect or pest resistance, disease resistance, modified fatty acid metabolism, altered water efficiency, altered nitrogen efficiency, altered protein quantity, modified protein composition, altered oil quantity, modified oil composition, altered starch quantity, modified starch composition, and modified carbohydrate metabolism. In some embodiments, the technology provides a plant or a selfed progeny thereof, wherein the plant or selfed progeny thereof comprises the transgene and otherwise comprises all of the morphological and physiological characteristics of Proso cultivar DLG240.

In some embodiments, the technology provides a method of introducing a locus conversion into a Proso plant. For example, in some embodiments, the method comprises: (a) crossing a plant of Proso cultivar DLG240 with a second plant comprising a desired locus to produce $F_1$ progeny plants; (b) selecting at least a first progeny plant from step (a) that comprises the locus to produce a selected progeny plant; (c) crossing the selected progeny plant from step (b) with a plant of Proso cultivar DLG240 to produce at least a first backcross progeny plant that comprises the locus; and (d) repeating steps (b) and (c) with the first backcross progeny plant produced from step (c) used in place of the first progeny plant of step (b) during the repeating, wherein steps (b) and (c) are repeated until at least a backcross progeny plant is produced comprising the locus conversion. In some embodiments, the locus confers a trait selected from the group consisting of male sterility, herbicide tolerance, insect or pest resistance, disease resistance, modified fatty acid metabolism, altered water efficiency, altered nitrogen efficiency, altered protein quantity, modified protein composition, altered oil quantity, modified oil composition, altered starch quantity, modified starch composition, abiotic stress resistance, and modified carbohydrate metabolism.

In some embodiments, the technology provides a Proso plant of Proso cultivar DLG240, further comprising a locus conversion, wherein the plant comprises the locus conversion and otherwise comprises all of the morphological and physiological characteristics of Proso cultivar DLG240.

In some embodiments, the technology provides a method of introducing a mutation into the genome of Proso cultivar DLG240, the method comprising applying a mutagen to the plant of claim 1, or a part thereof, wherein the resulting plant comprises a genome mutation. In some embodiments, the mutagen is selected from the group consisting of ethyl methanesulfonate, gamma rays, and sodium azide.

In some embodiments, the technology provides a method of producing a commodity plant product, the method comprising obtaining a Proso plant of Proso cultivar DLG240 or a part thereof and producing the commodity plant product therefrom. In some embodiments, the commodity plant product is seed, meal, flour, protein, or oil.

Furthermore, in some embodiments, the technology provides a plant of Proso cultivar DLG148. In some embodiments, the technology provides a seed that produces the plant of Proso cultivar DLG148. In some embodiments, the technology provides a cell of the plant of Proso cultivar DLG148. In some embodiments, the technology provides a tissue culture of regenerable cells comprising a cell of the plant of Proso cultivar DLG148.

In some embodiments, the technology provides a method of Proso breeding. For example, in some embodiments, the method comprises crossing the plant of Proso cultivar DLG148 with itself or a second Proso plant to produce Proso seed. In some embodiments, the method comprises crossing a plant of Proso cultivar DLG148 with a second Proso plant of a different genotype to produce hybrid Proso seed. In some embodiments, the method further comprises: (a) crossing a plant grown from the hybrid Proso seed with itself or a different Proso plant to produce a seed of a progeny plant of a subsequent generation. In some embodiments, the method further comprises (b) growing a progeny plant of a subsequent generation from the seed of a progeny plant of a subsequent generation and crossing the progeny plant of a subsequent generation with itself or a second plant to produce a progeny plant of a further subsequent generation. In some embodiments, the method further comprises (c) repeating steps (a) and (b) using the progeny plant of a further subsequent generation from step (b) in place of the plant grown from the hybrid Proso seed in step (a), wherein steps (a) and (b) are repeated with sufficient inbreeding to produce an inbred Proso plant derived from the Proso cultivar DLG148. In some embodiments, the technology provides an $F_1$ hybrid Proso seed produced by the method of Proso breeding.

In some embodiments, the technology provides a method of producing a plant comprising an added desired trait, the method comprising introducing a transgene conferring the desired trait into the plant of Proso cultivar DLG148. In some embodiments, the desired trait is selected from the group consisting of male sterility, herbicide tolerance, insect or pest resistance, disease resistance, modified fatty acid metabolism, altered water efficiency, altered nitrogen efficiency, altered protein quantity, modified protein composition, altered oil quantity, modified oil composition, altered starch quantity, modified starch composition, and modified carbohydrate metabolism. In some embodiments, the technology provides a plant or a selfed progeny thereof, wherein the plant or selfed progeny thereof comprises the transgene and otherwise comprises all of the morphological and physiological characteristics of Proso cultivar DLG148.

In some embodiments, the technology provides a method of introducing a locus conversion into a Proso plant. For example, in some embodiments, the method comprises: (a) crossing a plant of Proso cultivar DLG148 with a second plant comprising a desired locus to produce $F_1$ progeny plants; (b) selecting at least a first progeny plant from step (a) that comprises the locus to produce a selected progeny plant; (c) crossing the selected progeny plant from step (b) with a plant of Proso cultivar DLG148 to produce at least a first backcross progeny plant that comprises the locus; and (d) repeating steps (b) and (c) with the first backcross progeny plant produced from step (c) used in place of the first progeny plant of step (b) during the repeating, wherein steps (b) and (c) are repeated until at least a backcross progeny plant is produced comprising the locus conversion. In some embodiments, the locus confers a trait selected from the group consisting of male sterility, herbicide tolerance, insect or pest resistance, disease resistance, modified fatty acid metabolism, altered water efficiency, altered nitrogen efficiency, altered protein quantity, modified protein composition, altered oil quantity, modified oil composition, altered starch quantity, modified starch composition, abiotic stress resistance, and modified carbohydrate metabolism.

In some embodiments, the technology provides a Proso plant of Proso cultivar DLG148, further comprising a locus conversion, wherein the plant comprises the locus conversion and otherwise comprises all of the morphological and physiological characteristics of Proso cultivar DLG148.

In some embodiments, the technology provides a method of introducing a mutation into the genome of Proso cultivar DLG148, the method comprising applying a mutagen to the plant of claim 1, or a part thereof, wherein the resulting plant comprises a genome mutation. In some embodiments, the mutagen is selected from the group consisting of ethyl methanesulfonate, gamma-rays, and sodium azide.

In some embodiments, the technology provides a method of producing a commodity plant product, the method comprising obtaining a Proso plant of Proso cultivar DLG148 or a part thereof and producing the commodity plant product therefrom. In some embodiments, the commodity plant product is seed, meal, flour, protein, or oil.

Additionally, in some embodiments, the technology provides a plant of Proso cultivar DLG149. In some embodiments, the technology provides a seed that produces the plant of Proso cultivar DLG149. In some embodiments, the technology provides a cell of the plant of Proso cultivar DLG149. In some embodiments, the technology provides a tissue culture of regenerable cells comprising a cell of the plant of Proso cultivar DLG149.

In some embodiments, the technology provides a method of Proso breeding. For example, in some embodiments, the method comprises crossing the plant of Proso cultivar DLG149 with itself or a second Proso plant to produce Proso seed. In some embodiments, the method comprises crossing a plant of Proso cultivar DLG149 with a second Proso plant of a different genotype to produce hybrid Proso seed. In some embodiments, the method further comprises: (a) crossing a plant grown from the hybrid Proso seed with itself or a different Proso plant to produce a seed of a progeny plant of a subsequent generation. In some embodiments, the method further comprises (b) growing a progeny plant of a subsequent generation from the seed of a progeny plant of a subsequent generation and crossing the progeny plant of a subsequent generation with itself or a second plant to produce a progeny plant of a further subsequent generation. In some embodiments, the method further comprises (c) repeating steps (a) and (b) using the progeny plant of a further subsequent generation from step (b) in place of the plant grown from the hybrid Proso seed in step (a), wherein steps (a) and (b) are repeated with sufficient inbreeding to produce an inbred Proso plant derived from the Proso cultivar DLG149. In some embodiments, the technology provides an $F_1$ hybrid Proso seed produced by the method of Proso breeding.

In some embodiments, the technology provides a method of producing a plant comprising an added desired trait, the method comprising introducing a transgene conferring the desired trait into the plant of Proso cultivar DLG149. In some embodiments, the desired trait is selected from the group consisting of male sterility, herbicide tolerance, insect or pest resistance, disease resistance, modified fatty acid metabolism, altered water efficiency, altered nitrogen efficiency, altered protein quantity, modified protein composition, altered oil quantity, modified oil composition, altered starch quantity, modified starch composition, and modified carbohydrate metabolism. In some embodiments, the technology provides a plant or a selfed progeny thereof, wherein the plant or selfed progeny thereof comprises the transgene and otherwise comprises all of the morphological and physiological characteristics of Proso cultivar DLG149.

In some embodiments, the technology provides a method of introducing a locus conversion into a Proso plant. For example, in some embodiments, the method comprises: (a) crossing a plant of Proso cultivar DLG149 with a second plant comprising a desired locus to produce $F_1$ progeny plants; (b) selecting at least a first progeny plant from step (a) that comprises the locus to produce a selected progeny plant; (c) crossing the selected progeny plant from step (b) with a plant of Proso cultivar DLG149 to produce at least a first backcross progeny plant that comprises the locus; and (d) repeating steps (b) and (c) with the first backcross progeny plant produced from step (c) used in place of the first progeny plant of step (b) during the repeating, wherein steps (b) and (c) are repeated until at least a backcross progeny plant is produced comprising the locus conversion. In some embodiments, the locus confers a trait selected from the group consisting of male sterility, herbicide tolerance, insect or pest resistance, disease resistance, modified fatty acid metabolism, altered water efficiency, altered nitrogen efficiency, altered protein quantity, modified protein composition, altered oil quantity, modified oil composition, altered starch quantity, modified starch composition, abiotic stress resistance, and modified carbohydrate metabolism.

In some embodiments, the technology provides a Proso plant of Proso cultivar DLG149, further comprising a locus conversion, wherein the plant comprises the locus conversion and otherwise comprises all of the morphological and physiological characteristics of Proso cultivar DLG149.

In some embodiments, the technology provides a method of introducing a mutation into the genome of Proso cultivar DLG149, the method comprising applying a mutagen to the plant of claim 1, or a part thereof, wherein the resulting plant comprises a genome mutation. In some embodiments, the mutagen is selected from the group consisting of ethyl methanesulfonate, gamma-rays, and sodium azide.

In some embodiments, the technology provides a method of producing a commodity plant product, the method comprising obtaining a Proso plant of Proso cultivar DLG149 or a part thereof and producing the commodity plant product therefrom. In some embodiments, the commodity plant product is seed, meal, flour, protein, or oil.

In some embodiments, the technology relates to a method of planting crops. In some embodiments, the methods comprise planting a higher-yielding Proso (e.g., Proso cultivar DLG40, DLG240, DLG148, or DLG149); and planting a second plant. In some embodiments, the second plant is a plant comprising roots below approximately the top 100 to 150 cm (e.g., below approximately the top 90, 95, 100, 105, 110, 115, 120, 125, 130, 135, 140, 145, 150, 155, 160, 165, 170, or 175 cm) of soil. In some embodiments, the second plant is a row crop, a legume, a grass, a pulse, or a cereal. In some embodiments, the second plant is wheat, corn, soybeans, oats, sorghum, canola, field peas, lentils, or sunflower. In some embodiments, the methods further comprise planting a third plant. In some embodiments, the third plant is wheat, corn, soybeans, oats, sorghum, canola, field peas, lentils, or sunflower. In some embodiments, the method of planting crops is a method of crop rotation wherein the higher-yielding Proso and the second plant are planted in the same field in different growing seasons; or the method is a method of crop rotation wherein the higher-yielding Proso and the second plant are planted in different fields in the same growing season. In some embodiments, the method of planting crops is a companion planting (also known as "intercropping") method or nurse cropping method wherein the higher-yielding Proso and the second plant are planted in the same field in the same growing season.

In some embodiments, the technology provides a method for selecting a higher-yielding Proso plant (e.g., Proso cultivar DLG40, DLG240, DLG148, or DLG149). For example, in some embodiments, methods comprise detecting at least one alternative allele in a nucleic acid for a single nucleotide polymorphism (SNP); and selecting a Proso plant comprising the alternative allele, thereby selecting a higher-yielding Proso plant. In some embodiments, the SNP is provided by the table entitled "Proso_SNP_Table.txt" available in electronic form for this disclosure. In some embodiments, the technology provides a method for screening Proso seeds, plants, or plant parts; or DNA from such seeds, plants; or plant parts for the presence of one or more markers linked to an increased yield phenotype, the method comprising: detecting at least one alternative allele in a nucleic acid for a SNP provided by the table entitled "Proso_SNP_Table.txt" available in electronic form for this disclosure; and selecting one or more seeds, plants, or plant parts comprising a nucleic acid comprising the SNP. In some embodiments, the technology provides a method of producing a population of Proso plants with an increased yield phenotype, the method comprising: genotyping a first population of Proso plants or seeds; detecting in the first population of Proso plants or seeds a polymorphic nucleic acid marker linked by less than or equal to 10 cM to an allele associated with an increased yield phenotype; selecting based upon the genotyping a Proso plant or seed comprising the allele that was detected by genotyping; crossing or selfing the selected Proso plant or a plant produced from the selected seed; and producing from the crossing or selfing a population of progeny plants comprising the allele that is associated with the increased yield phenotype.

In some embodiments, the technology provides a method of producing a Proso plant that has improved yield relative to a control plant, the method comprising: isolating a nucleic acid from a Proso plant; detecting in the nucleic acid the presence of a genetic marker that is associated with improved yield; selecting a first Proso plant based on the presence of the genetic marker; crossing a second Proso plant with the first Proso plant, wherein the second Proso plant does not comprise in its genome the genetic marker; and producing seed from the crossing. In some embodiments, the method further comprises producing a Proso plant from the seed, wherein the Proso plant has improved yield compared to a control plant.

In some embodiments, the technology relates to uses, e.g., use of a plant of Proso cultivar DLG40, DLG240, DLG148, or DLG149 to produce seed. In some embodiments, the technology provides use of a plant of Proso cultivar DLG40, DLG240, DLG148, or DLG149 for crossing with a second Proso plant, for selfing, backcrossing, producing hybrids, and/or crossing to populations. In some embodiments, the technology provides use of a plant of Proso cultivar DLG40, DLG240, DLG148, or DLG149 to produce a plant having a desired trait by introducing a transgene conferring the desired trait into a plant of Proso cultivar DLG40, DLG240, DLG148, or DLG149. In some embodiments, the trait is male sterility, herbicide tolerance, insect or pest resistance, disease resistance, modified fatty acid metabolism, altered water efficiency, altered nitrogen efficiency, altered protein quantity, modified protein composition, altered oil quantity, modified oil composition, altered starch quantity, modified starch composition, or modified carbohydrate metabolism. In some embodiments, the technology provides use of a plant of Proso cultivar DLG40, DLG240, DLG148, or DLG149 to produce a plant having a locus conversion. In some embodiments, the technology provides use of a plant of Proso cultivar DLG40, DLG240, DLG148, or DLG149 to produce a commodity plant product. In some embodiments, the technology provides use of a plant of Proso cultivar DLG40, DLG240, DLG148, or DLG149 to produce a feed for an animal or a food for a human. In some embodiments, the technology provides use of a plant of Proso cultivar DLG40, DLG240, DLG148, or DLG149 to produce a biofuel. In some embodiments, the technology provides use of a plant of Proso cultivar DLG40, DLG240, DLG148, or DLG149 for crop rotation.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings.

Figure 1A:
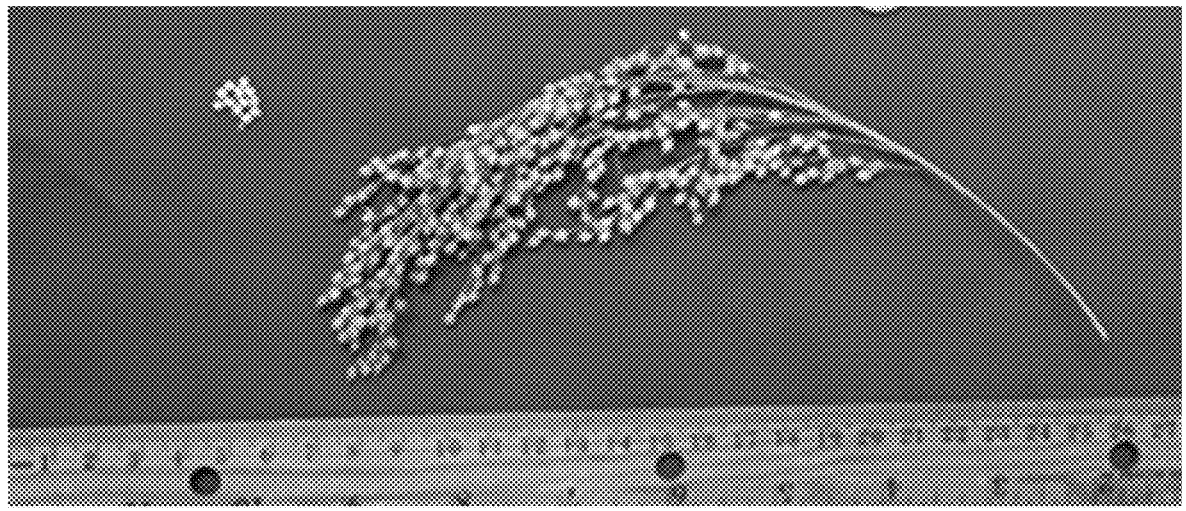
FIG. 1A is a photograph showing panicle type of DLG40 grown in 2020 at Ames IA.
Figure 1B:
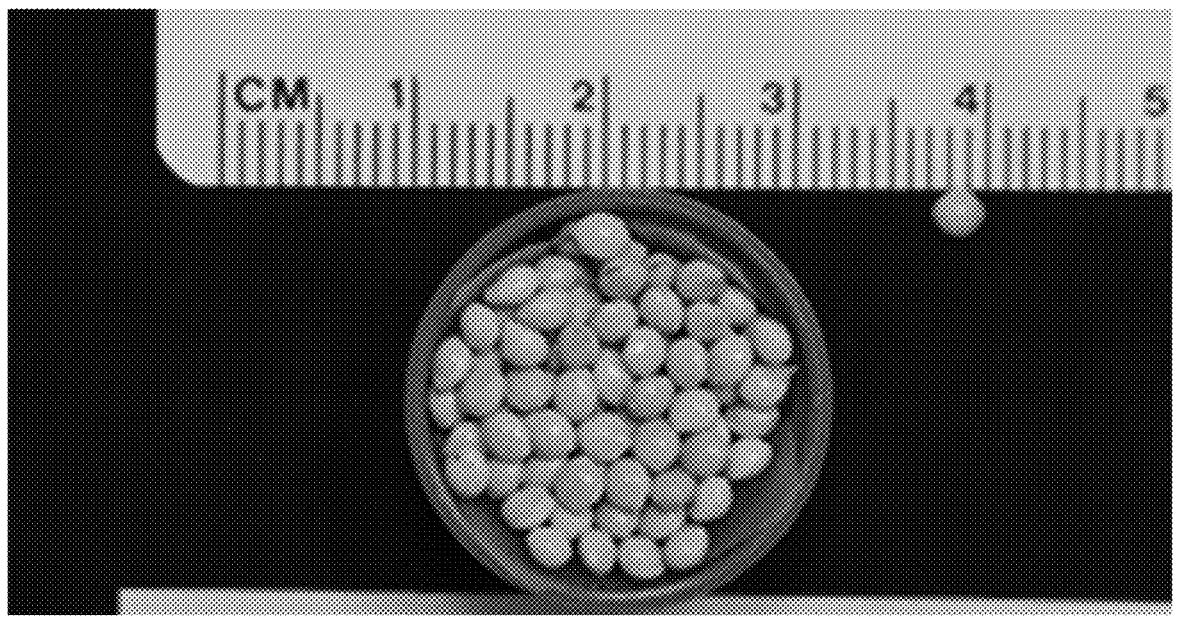
FIG. 1B is a photograph showing seeds of DLG40 grown in 2020 at Ames IA.
Figure 2A:
FIG. 2A is a photograph showing panicle type of DLG240 grown in 2020 at Ames IA.
Figure 2B:
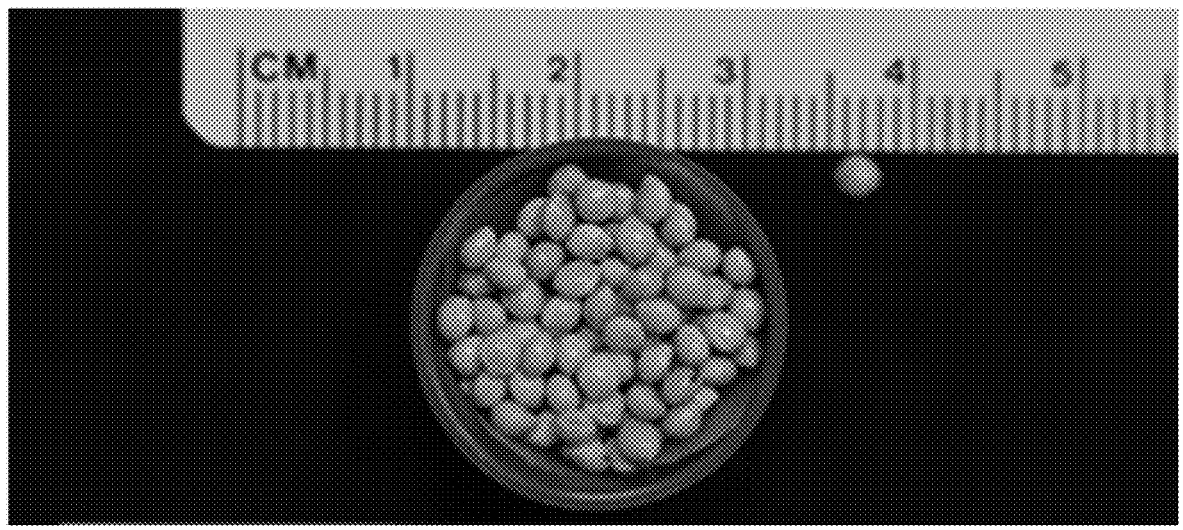
FIG. 2B is a photograph showing seeds of DLG240 grown in 2020 at Ames IA.
Figure 3A:
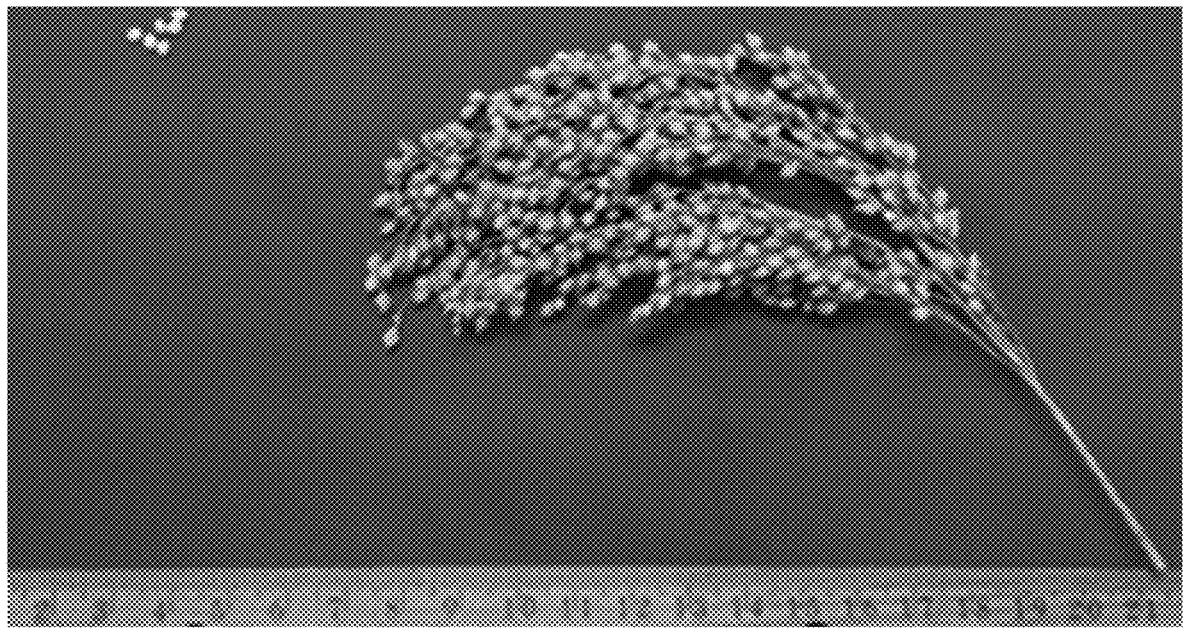
FIG. 3A is a photograph showing panicle type of DLG148 grown in 2020 at Ames IA.
Figure 3B:
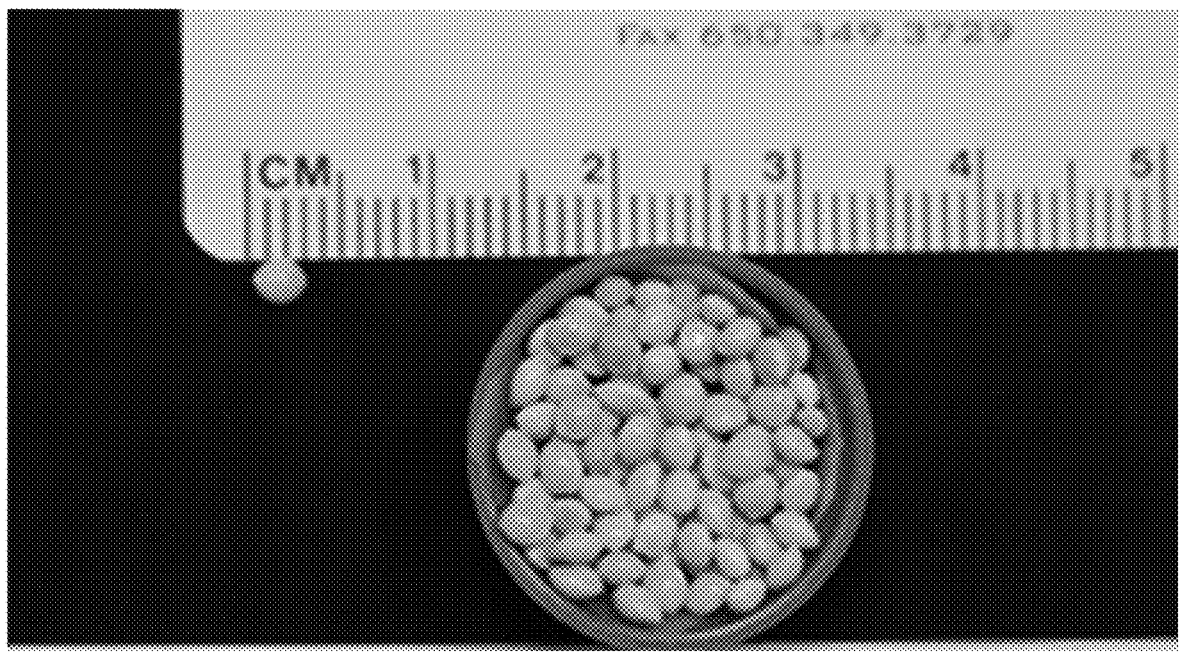
FIG. 3B is a photograph showing seeds of DLG148 grown in 2020 at Ames IA.
Figure 4A:
FIG. 4A is a photograph showing panicle type of DLG149 grown in 2020 at Ames IA.
Figure 4B:
FIG. 4B is a photograph showing seeds of DLG149 grown in 2020 at Ames IA.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

Provided herein is technology relating to water-efficient plants and particularly, but not exclusively, to varieties of Proso (proso millet, *Panicum miliaceum*) with improved yields and methods and systems for improving the yield of Proso varieties and producing higher-yielding Proso varieties.

Proso is a grain crop native to northern China and the Caucasus region that is currently grown in limited portions of the Great Plains in the United States. The technology provided herein relates to varieties of Proso produced using modern breeding approaches (e.g., genotyping-by-sequencing, high throughput phenotyping, and genomic selection). Accordingly, described herein are higher-yielding varieties of Proso that are more widely adapted than conventional varieties (e.g., Huntsman or other varieties that trace parentage to the Dawn variety). Other conventional varieties known in the art include, e.g., Earlybird, Dawn, Horizon, Sunrise, Sunup, Plateau, Dove, and Cerise.

Methods for genetic characterization of Proso include, e.g., amplified fragment length polymorphism (AFLP) (see, e.g., Karam (2004) "Genetic diversity among proso millet (*Panicum miliaceum*) biotypes assessed by AFLP techniques" Planta Daninha 22:167-74; and Karam (2006) "Assessment of silver-stained AFLP markers for studying DNA polymorphism in proso millet (*Panicum miliaceum* L.)" Rev. Brasil Bot. 29:609-15, each of which is incorporated herein by reference); random amplified polymorphic DNA (RAPD) (see, e.g., M'Ribu (1994) "Detection of inter specific and intraspecific variation in *Panicum* millets through random amplified polymorphic DNA" Theor. Appl. Genet. 88:412-16; and Colosi (1997) "Wild proso millet (*Panicum miliaceum*) is genetically variable and distinct from crop varieties of proso millet" Weed Sci. 45:509-18, each of which is incorporated herein by reference); cleaved amplified polymorphic DNA (CAP) (see, e.g., Lágler (2005) "Morphological and molecular analysis of common millet (*P. miliaceum*) cultivars compared to a DNA sample from the 15th century (Hungary)" Euphytica 146:77-85, incorporated herein by reference); inter simple sequence repeats (ISSR) (see, e.g., Lagler, supra; and Trivedi (2015) "Genetic variability in proso millet (*Panicum miliaceum*) germplasm of Central Himalayan Region based on morpho-physiological traits and molecular markers" Acta Physiol. 37:23-38, incorporated herein by reference); sequence related amplified polymorphism (SRAP) (see, e.g., Trivedi, supra); and simple sequence repeat (SSR) polymorphic markers (see, e.g., Hu (2009) "Assessment of genetic diversity in broomcorn millet (*Panicum miliaceum* L.) using SSR markers" J. Genet. Genomics 36:491-500; Cho (2010) "Development and characterization of twenty-five new polymorphic microsatellite markers in proso millet (*Panicum miliaceum* L.) Genes Genomics 32:267-73; Hunt (2010) "Molecular basis of the waxy endosperm starch phenotype in broomcorn millet (*Panicum miliaceum* L.) Mol. Biol. Evol. 27:1478-94; Hunt (2011) "Genetic diversity and phylogeography of broomcorn millet (*Panicum miliaceum* L.) across Eurasia" Mol. Ecol. 20:4756-71; Rajput (2014) "Development and characterization of SSR markers in proso millet (*Panicum miliaceum* L.) based on switchgrass genomics" Am. J. Plant Sci. 5:175-86; Dvořáková (2015) "Comparative analysis of genetic diversity of 8 millet genera revealed by ISSR markers" Emirates J. Food Agric. 27:617-28; and Rajput (2016) "Evaluation of genetic diversity of proso millet germplasm available in the United States using simple-sequence repeat markers" Crop Sci. 56:1-9, each of which is incorporated herein by reference). Further, genetic linkage maps of Proso are available, e.g., using SNP markers discovered through genotype-by-sequencing (GBS) (see, e.g., He (2014) "Genotyping-by-sequencing (GBS), an ultimate marker-assisted (MAS) tool to accelerate plant breeding" Front. Plant Sci. 5:484, incorporated herein by reference).

In some embodiments, the technology relates to varieties of Proso that are characterized genetically and/or genomically, e.g., using one or more genetic markers, e.g., one or more SNPs. In some embodiments, the Proso varieties described herein have a genome comprising one or more SNPs determined relative to a reference genome sequence.

For example, during the development of the technology provided herein, experiments were conducted to determine the nucleotide bases present at approximately 20,000 positions in the Proso genome for the Proso varieties described herein. Accordingly, in some embodiments, the technology provides Proso varieties that are genetically and/or genomically characterized according to one or more genetic marker positions (e.g., SNPs).

SNP data provided herein for Proso varieties are described at these approximately 20,000 genomic positions using a reference genome sequence assembly available for *Panicum*

*milianceum* as published by Zou (2019) "The genome of broomcorn millet" Nature Communications 10:436, incorporated herein by reference.

As used herein, the term "reference Proso genomic sequence" or "reference Proso genome sequence" refers to the *Panicum milianceum* genome sequence published by Zou (Zou (2019) "The genome of broomcorn millet" Nature Communications 10:436, incorporated herein by reference). Further, in some embodiments, a Proso genome sequence provided by Ott et al. (2018) "Linked read technology for assembling large complex and polyploid genomes" BMC Genomics 19:651, incorporated herein by reference, may also find use in embodiments of the technology provided herein (e.g., as a reference genome sequence).

As used herein, a "reference allele" has the nucleotide sequence (e.g., at a SNP location) provided by the reference Proso genomic sequence, e.g., the genome sequence published by Zou and/or Ott. As used herein, the term "alternative allele" has a nucleotide sequence that differs from the nucleotide sequence (e.g., at a SNP location) provided by the reference Proso genomic sequence published by Zou and/or Ott.

Proso is an allotetraploid with 36 chromosomes. The reference Proso genomic sequence comprises 18 chromosomal sequences and a chloroplast sequence. The genome assembly and sequence data for the reference Proso genomic sequence is available at NCBI under BioProject number PRJNA431363 and through CoGe (genomevolution.org, Genome ID: 52484). In particular, the reference Proso genomic sequence is available at NCBI at the accession numbers provided in Table 33, each of which is incorporated herein by reference.

For example, in some embodiments, the Proso varieties described herein comprise a genome having one or more nucleotides that differ from the reference Proso genomic sequence. In some embodiments, the Proso varieties described herein comprise a genome having one or more polymorphic positions having the sequence of the reference allele (e.g., as provided by the reference genome sequence) and one or more polymorphic positions having the sequence of the alternate allele.

Proso is a water-efficient plant. In particular, Proso uses less water, requires less nitrogen, and/or thrives on land where some other crops fail in the absence of irrigation. Under water-limiting conditions Proso can produce 2× more grain per gallon of water than corn and can substitute for corn in both animal feed and ethanol production. For example, in some previous measures of water use and yield, data collected indicated that Proso had a water-limited yield relationship of 32.57 kg ha-1 per mm of water use. (Nielsen (2017) "Water use and environmental parameters influence proso millet yield" Field Crops Research 212:34-44, incorporated herein by reference).

In some embodiments, the Proso varieties provide herein have very limited water requirements. For example, in some embodiments, the Proso varieties have maximal yields with less than 12 inches (e.g., less than 12.0, 11.9, 11.8, 11.7, 11.6, 11.5, 11.4, 11.3, 11.2, 11.1, 11.0, 10.9, 10.8, 10.7, 10.6, 10.5, 10.4, 10.3, 10.2, 10.1, 10.0, 9.9, 9.8, 9.7, 9.6, 9.5, 9.4, 9.3, 9.2, 9.1, 9.0, 8.9, 8.8, 8.7, 8.6, 8.5, 8.4, 8.3, 8.2, 8.1, 8.0, 7.9, 7.8, 7.7, 7.6, 7.5, 7.4, 7.3, 7.2, 7.1, 7.0, 6.9, 6.8, 6.7, 6.6, 6.5, 6.4, 6.3, 6.2, 6.1, or 6.0 inches) of water in a growing season. In some embodiments, the Proso varieties grow and produce seed with less than 6 inches (e.g., less than 6.0, 5.9, 5.8, 5.7, 5.6, 5.5, 5.4, 5.3, 5.2, 5.1, 5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, or 2.0 inches) of water in a growing season. Accordingly, in some embodiments, the Proso varieties provided herein can be grown on inexpensive and under-utilized land (e.g., land where corn and wheat production is not economically viable). In some embodiments, the Proso varieties have a water efficiency of more than 250 pounds/acre per inch of water (e.g., more than 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 pounds/acre per inch of water).

During the development of embodiments of the technology described herein, experiments were conducted to measure absolute yields and yields relative to known Proso varieties. In some embodiments, the Proso varieties described herein (e.g., DLG40, DLG240, DLG148, and/or DLG149) have a yield that is greater than known Proso varieties (e.g., Dawn, Earlybird, Horizon, Huntsman, Plateau, and/or Sunup). For example, in some embodiments, the Proso varieties described herein (e.g., DLG40, DLG240, DLG148, and/or DLG149) have a yield that is at least 1.1× greater than known Proso varieties (e.g., Dawn, Earlybird, Horizon, Huntsman, Plateau, and/or Sunup). For example, in some embodiments, the Proso varieties described herein (e.g., DLG40, DLG240, DLG148, and/or DLG149) have a yield that is 1.1× to 3× greater (e.g., 1.1×, 1.2×, 1.3×, 1.4×, 1.5×, 1.6×, 1.7×, 1.8×, 1.9×, 2.0×, 2.1×, 2.2×, 2.3×, 2.4×, 2.5×, 2.6×, 2.7×, 2.8×, 2.9×, or 3.0× greater) than known Proso varieties (e.g., Dawn, Earlybird, Horizon, Huntsman, Plateau, and/or Sunup). See, e.g., the Examples. In some embodiments, the Proso varieties described herein (e.g., DLG40, DLG240, DLG148, and/or DLG149) have an average dry weight grain yield, an average GPS adjusted mean grain yield, an average as-is grain yield, and/or an average test weight that is 1.1× to 3× greater (e.g., 1.1×, 1.2×, 1.3×, 1.4×, 1.5×, 1.6×, 1.7×, 1.8×, 1.9×, 2.0×, 2.1×, 2.2×, 2.3×, 2.4×, 2.5×, 2.6×, 2.7×, 2.8×, 2.9×, or 3.0× greater) than known Proso varieties (e.g., Dawn, Earlybird, Horizon, Huntsman, Plateau, and/or Sunup).

In some embodiments, the Proso varieties described herein (e.g., DLG40, DLG240, DLG148, and/or DLG149) have a yield that is 400-5000 pounds/acre (e.g., 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, 1490, 1500, 1510, 1520, 1530, 1540, 1550, 1560, 1570, 1580, 1590, 1600, 1610, 1620, 1630, 1640, 1650, 1660, 1670, 1680, 1690, 1700, 1710, 1720, 1730, 1740, 1750, 1760, 1770, 1780, 1790, 1800, 1810, 1820, 1830, 1840, 1850, 1860, 1870, 1880, 1890, 1900, 1910, 1920, 1930, 1940, 1950, 1960, 1970, 1980, 1990, 2000, 2010, 2020, 2030, 2040, 2050, 2060, 2070, 2080, 2090, 2100, 2110, 2120, 2130, 2140, 2150, 2160, 2170, 2180, 2190, 2200, 2210, 2220, 2230, 2240, 2250, 2260, 2270, 2280, 2290, 2300, 2310, 2320, 2330, 2340, 2350, 2360, 2370, 2380, 2390, 2400, 2410, 2420, 2430, 2440, 2450, 2460, 2470, 2480, 2490, 2500, 2510, 2520, 2530, 2540, 2550, 2560, 2570, 2580, 2590, 2600, 2610, 2620, 2630, 2640, 2650, 2660, 2670, 2680, 2690, 2700, 2710, 2720, 2730, 2740, 2750, 2760, 2770, 2780, 2790, 2800, 2810, 2820, 2830, 2840, 2850, 2860, 2870, 2880, 2890, 2900, 2910, 2920, 2930, 2940, 2950, 2960, 2970, 2980, 2990, 3000, 3010, 3020, 3030, 3040, 3050, 3060, 3070, 3080, 3090, 3100, 3110, 3120, 3130, 3140, 3150, 3160, 3170, 3180, 3190, 3200, 3210, 3220, 3230, 3240, 3250, 3260, 3270, 3280, 3290, 3300, 3310, 3320, 3330, 3340, 3350, 3360, 3370, 3380, 3390, 3400, 3410, 3420, 3430, 3440, 3450, 3460, 3470, 3480, 3490, 3500, 3510, 3520, 3530, 3540, 3550, 3560, 3570, 3580, 3590, 3600, 3610, 3620, 3630, 3640, 3650, 3660, 3670, 3680, 3690, 3700, 3710, 3720, 3730, 3740, 3750, 3760, 3770, 3780, 3790, 3800, 3810, 3820, 3830, 3840, 3850, 3860, 3870, 3880, 3890, 3900, 3910, 3920, 3930, 3940, 3950, 3960, 3970, 3980, 3990, 4000, 4010, 4020, 4030, 4040, 4050, 4060, 4070, 4080, 4090, 4100, 4110, 4120, 4130, 4140, 4150, 4160, 4170, 4180, 4190, 4200, 4210, 4220, 4230, 4240, 4250, 4260, 4270, 4280, 4290, 4300, 4310, 4320, 4330, 4340, 4350, 4360, 4370, 4380, 4390, 4400, 4410, 4420, 4430, 4440, 4450, 4460, 4470, 4480, 4490, 4500, 4510, 4520, 4530, 4540, 4550, 4560, 4570, 4580, 4590, 4600, 4610, 4620, 4630, 4640, 4650, 4660, 4670, 4680, 4690, 4700, 4710, 4720, 4730, 4740, 4750, 4760, 4770, 4780, 4790, 4800, 4810, 4820, 4830, 4840, 4850, 4860, 4870, 4880, 4890, 4900, 4910, 4920, 4930, 4940, 4950, 4960, 4970, 4980, 4990, or 5000 pounds per acre). In some embodiments, the Proso varieties described herein (e.g., DLG40, DLG240, DLG148, and/or DLG149) have an average test weight that is greater than 40 pounds per bushel, e.g., approximately 40-60 pounds per bushel (e.g., 40, 41, 42, 43, 44, 45, 46, 47, 48, 49, 50, 51, 52, 53, 54, 55, 56, 57, 58, 59, or 60 pounds per bushel).

Proso can be substituted for corn in both animal feed and ethanol production. Accordingly, in some embodiments, the Proso varieties provided herein find use in animal feed. In some embodiments, the Proso varieties provided herein find use in producing a biofuel (e.g., ethanol). In some embodiments, the Proso varieties provided herein find use in producing an ethanol for human consumption. In some embodiments, the Proso varieties provided herein find use in producing an ethanol for commercial and/or industrial use. In some embodiments, Proso provides a food for a human, e.g., a gluten-free food for a human. In some embodiments, Proso provides a food for a human having an adverse inflammatory, immunological, and/or autoimmune reaction to gluten (e.g., celiac disease, non-celiac gluten sensitivity, dermatitis herpetiformis, gluten ataxia, and/or gluten intolerance).

Proso has a rapid generation time (e.g., approximately 45 to 60 days to produce seed after planting). Accordingly, in some embodiments, the technology provided herein provides a breeding program comprising breeding up to five generations per year (e.g. using a controlled plant growth facility (e.g., a growth room without windows and in which light is provided by light emitting diodes)). In some embodiments, the technology provides a breeding program in which a 36-month breeding program replaces a 15-year conventional breeding program using genomic selection to guide intercrossing of individuals at each generation and/or at one or more but not all generations(s).

In some embodiments, the technology comprises use of quantitative genetic approaches (e.g., genomic selection) to produce improved Proso varieties, e.g., Proso having improved yields (higher-yielding Proso). During genomic selection, a statistical model for the value of different alleles at different chromosomal sites is constructed using genotypic and phenotypic data from the founding parents of a breeding population. Subsequently, this statistical model is used as a guide for selecting individuals to mate to produce subsequent generations. In some embodiments, the statistical model identifies individuals for mating without collecting reliable trait and/or yield data, e.g., when a crop is grown in a controlled plant growth facility (e.g., a growth room without windows and in which light is provided by light emitting diodes). In some embodiments, quantitative genetic methods (e.g., genomic selection) comprise providing (e.g., producing, obtaining, recording, and/or acquiring) high density genotyping data from individual plants (e.g., from thousands of individuals); and providing (e.g., producing, obtaining, recording, and/or acquiring) accurate, high-resolution phenotyping information from individual plants (e.g., from thousands of individuals).

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control. The section headings used herein are for organizational purposes only and are not to be construed as limiting the described subject matter in any way.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, the terms "about", "approximately", "substantially", and "significantly" are understood by persons of ordinary skill in the art and will vary to some extent on the context in which they are used. If there are uses of these terms that are not clear to persons of ordinary skill in the art given the context in which they are used, "about" and "approximately" mean plus or minus less than or equal to 10% of the particular term and "substantially" and "significantly" mean plus or minus greater than 10% of the particular term.

As used herein, disclosure of ranges includes disclosure of all values and further divided ranges within the entire range, including endpoints and sub-ranges given for the ranges.

As used herein, the suffix "-free" refers to an embodiment of the technology that omits the feature of the base root of the word to which "-free" is appended. That is, the term "X-free" as used herein means "without X", where X is a feature of the technology omitted in the "X-free" technology. For example, a "calcium-free" composition does not comprise calcium, a "mixing-free" method does not comprise a mixing step, etc.

Although the terms "first", "second", "third", etc. may be used herein to describe various steps, elements, compositions, components, regions, layers, and/or sections, these steps, elements, compositions, components, regions, layers, and/or sections should not be limited by these terms, unless otherwise indicated. These terms are used to distinguish one step, element, composition, component, region, layer, and/or section from another step, element, composition, component, region, layer, and/or section. Terms such as "first", "second", and other numerical terms when used herein do not imply a sequence or order unless clearly indicated by the context. Thus, a first step, element, composition, component, region, layer, or section discussed herein could be termed a second step, element, composition, component, region, layer, or section without departing from technology.

As used herein, the word "presence" or "absence" (or, alternatively, "present or "absent") is used in a relative sense to describe the amount or level of a particular entity (e.g., an analyte). For example, when an analyte is said to be "present" in a test sample, it means the level or amount of this analyte is above a pre determined threshold; conversely, when an analyte is said to be "absent" in a test sample, it means the level or amount of this analyte is below a pre determined threshold. The pre determined threshold may be the threshold for detectability associated with the particular test used to detect the analyte or any other threshold. When an analyte is "detected" in a sample it is "present" in the sample; when an analyte is "not detected" it is "absent" from the sample. Further, a sample in which an analyte is "detected" or in which the analyte is "present" is a sample that is "positive" for the analyte. A sample in which an analyte is "not detected" or in which the analyte is "absent" is a sample that is "negative" for the analyte.

As used herein, an "increase" or a "decrease" refers to a detectable (e.g., measured) positive or negative change, respectively, in the value of a variable relative to a previously measured value of the variable, relative to a pre-established value, and/or relative to a value of a standard control. An increase is a positive change preferably at least 10%, more preferably 50%, still more preferably 2-fold, even more preferably at least 5-fold, and most preferably at least 10-fold relative to the previously measured value of the variable, the pre-established value, and/or the value of a standard control. Similarly, a decrease is a negative change preferably at least 10%, more preferably 50%, still more preferably at least 80%, and most preferably at least 90% of the previously measured value of the variable, the pre-established value, and/or the value of a standard control. Other terms indicating quantitative changes or differences, such as "more" or "less," are used herein in the same fashion as described above. As used herein, the term "increasing tolerance" or "increased tolerance" refers to an increase relative to a control (e.g., a wild-type control or a non-transformed control plant or non-transformed plant part), such as when a transgenic plant or leaf from a transgenic plant of the present technology is compared to a closely related non-transformed wild-type plant or a leaf from a non-transformed wild-type plant.

As used herein, a "system" refers to a plurality of real and/or abstract components operating together for a common purpose. In some embodiments, a "system" is an integrated assemblage of hardware and/or software components. In some embodiments, each component of the system interacts with one or more other components and/or is related to one or more other components. In some embodiments, a system refers to a combination of components and software for controlling and directing methods.

Proso (*Panicum miliaceum*) can be referred to as "millet" or "proso millet". Proso is also known in the art by the names Proso, hog millet, yellow hog, broomcorn millet, and common millet.

As used herein, the term "abiotic stress" relates to all non-living chemical and physical factors in the environment. Examples of abiotic stress include, but are not limited to, drought, flooding, salinity, temperature, and climate change.

As used herein, the term "abiotic stress tolerance" refers to resistance to abiotic stress conferred by traits of a plant. Examples of abiotic stress tolerance include, but are not limited to, altered or modified nitrogen utilization efficiency, altered or modified nitrogen responsiveness, altered water use efficiency, altered cold resistance, and altered or modified salt resistance.

As used herein, the terms "altered" or "modified" are used in some embodiments to describe a quantitative and/or qualitative change in some observable, detectable, and/or measurable value or quality or characteristic of something, e.g., a plant or plant part. For example, an "altered" characteristic (e.g., trait, phenotype), parameter, or variable has increased or decreased (e.g., according to some quantitative measurement of the characteristic (e.g., trait, phenotype), parameter, or variable). For example, a "modified" characteristic (e.g., trait), parameter, or variable has changed in quality, appearance, structure, arrangement, composition, etc. (e.g., according to a qualitative measurement of the characteristic (e.g., trait, phenotype), parameter, or variable). In some embodiments, the altered or modified change is expressed relative to an unaltered or unmodified state or condition (e.g., prior to having been "altered" or "modified"), respectively.

As used herein, the term "resistance" or "tolerance" refers to the ability of a plant to withstand exposure to an insect, disease, herbicide, drought, or other condition. A resistant plant variety will have a level of resistance higher than a comparable wild-type variety.

As used herein, the term "allele" refers to any of one or more alternative forms of a genetic sequence. In a polyploid (e.g., diploid, triploid, tetraploid, etc.) cell or organism, the alleles of a given sequence typically occupy corresponding loci on homologous chromosomes. Thus, the terms "allele" and "alleles" refer to each version of a gene for a same locus that has more than one sequence.

As used herein, the term "anthesis" refers to the time of a flower opening.

As used herein, the term "backcrossing" refers to a process in which a breeder crosses progeny back to one of the parental genotypes one or more times. In some embodiments, backcrossing finds use in introducing one or more locus conversions from one genetic background into another.

As used herein, the term "breeding" refers to the genetic manipulation of living organisms.

As used herein, the term "backcross progeny" refers to progeny plants produced by crossing one Proso line (recurrent parent) with plants of another Proso line (donor) that comprise a desired trait or locus, selecting progeny plants that comprise the desired trait or locus, and crossing them with the recurrent parent one or more times to produce backcross progeny plants that comprise said trait or locus.

As used herein, the term "breeding cross" refers to a cross to introduce new genetic material into a plant for the development of a new variety. For example, one could cross plant A with plant B, wherein plant B would be genetically different from plant A. After the breeding cross, the resulting $F_1$ plants could then be selfed or sibbed for one, two, three, or more times ($F_1$, $F_2$, $F_3$, etc.) until a new inbred variety is developed.

As used herein, the term "Fa:Fb", where each of "a" and "b" is an integer and b is a+1, e.g., when used to refer to an "Fa:Fb line", "Fa:Fb head row", "Fa:Fb seed", "Fa:Fb generation", and the like, refers to a line, head row, seed, generation, and the like produced by harvesting a single Fa plant and planting the Fb seeds (e.g., in a row) to produce the line, row (e.g., head row), seed, generation, or the like.

As used herein, the term "Fa:Fc", where each of "a", "b", and "c" is an integer and a<b<c, e.g., when used to refer to an "Fa:Fc line", "Fa:Fc head row", "Fa:Fc seed", "Fa:Fc generation", and the like, refers to a line, head row, seed, generation, or the like produced by harvesting a single Fa plant, planting the Fb seeds (e.g., in a row), harvesting all Fb seeds in bulk, using the Fb seeds to plant (e.g., in a row) the next (b+1) generation, and repeating until the cth generation to produce the line, row (e.g., head row), seed, generation, or the like.

As used herein, the term "BU/A" refers to the yield of the grain at harvest by weight or volume (bushels) per unit area (acre).

As used herein, the term "cell" refers to a plant cell, whether isolated, in tissue culture, or incorporated in a plant or plant part.

As used herein, the term "cross pollination" refers to fertilization by the union of two gametes from different plants.

As used herein, the term "crossing" refers to the combination of genetic material by traditional methods such as a breeding cross or backcross, but also including protoplast fusion and other molecular biology methods of combining genetic material from two sources.

As used herein, the term "diploid" refers to a cell or organism having two sets of chromosomes.

As used herein, the term "diploid plant part" refers to a plant part or cell that has a diploid genotype.

As used herein, the term "triploid" refers to a cell or organism having three sets of chromosomes.

As used herein, the term "triploid plant part" refers to a plant part or cell that has a triploid genotype.

As used herein, the term "tetraploid" refers to a cell or organism having four sets of chromosomes.

As used herein, the term "tetraploid plant part" refers to a plant part or cell that has a tetraploid genotype.

As used herein, the term "polyploid" refers to a cell or organism having two or more sets of chromosomes.

As used herein, the term "polyploid plant part" refers to a plant part or cell that has a polyploid genotype.

As used herein, the term "embryo" refers to the small plant contained within a mature seed.

As used herein, the term "expression" when used in reference to a nucleic acid sequence, such as a gene, refers to the process of converting genetic information encoded in a gene into RNA (e.g., mRNA, rRNA, tRNA, or snRNA) through "transcription" of the gene (i.e., via the enzymatic action of an RNA polymerase), and into protein where applicable (as when a gene encodes a protein), through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down regulation are often called "activators" and "repressors", respectively.

As used herein, the term "$F_n$" refers to a filial generation. The "F" denotes the filial generation, and the subscript "n" is the generation number, such as $F_1$, $F_2$, $F_3$, etc.

As used herein the term "$F_1$ progeny" refers to a progeny plant produced by crossing a plant of one Proso line with a plant of another Proso line.

As used herein, the term "gene" refers to a unit of inheritance corresponding to DNA or RNA that code for a protein or for an RNA that has a function in the organism. In particular, the term "gene" refers to a nucleic acid (e.g., DNA or RNA) sequence that comprises coding sequences necessary for the production of an RNA, or a polypeptide or its precursor. A functional polypeptide can be encoded by a full-length coding sequence or by any portion of the coding sequence as long as the desired activity or functional properties (e.g., enzymatic activity, ligand binding, signal transduction, etc.) of the polypeptide are retained. The term "gene" encompasses the coding regions of a structural gene and includes sequences located adjacent to the coding region on both the 5' and 3' ends for a distance of approximately 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences.

As used herein, the term "gene" encompasses both cDNA and genomic forms of a gene. A genomic form or clone of a gene contains the coding region termed "exon" or "expressed regions" or "expressed sequences" interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, posttranscriptional cleavage and polyadenylation. The term "portion" when used in reference to a gene refers to fragments of that gene. The fragments may range in size from a few nucleotides to the entire gene sequence minus one nucleotide.

As used herein, the term "genotype" refers to the genetic constitution of a cell or organism.

As used herein, the term "grain" refers to a non-dehulled seed (i.e., a hull, endosperm, and embryo). Grain can be various colors such as red, brown, black, white, cream, and shades of these colors.

As used herein, the term "kernel" refers to a dehulled seed (i.e, endosperm and embryo). A kernel is typically whitish to yellowish.

As used herein, the term "haploid" refers to a cell or organism having a number of sets of chromosomes normally found in a gamete for that organism, e.g., one set of the two sets of chromosomes in a diploid (e.g., a "monoploid"), two sets of the four sets of chromosomes in a tetraploid, etc.

As used herein, the term "haploid plant part" refers to a plant part or cell having a haploid genotype.

As used herein, the term "heterologous nucleic acid" (e.g., a "heterologous gene") refers to any nucleic acid that is introduced into the genome of an organism or tissue of an organism or a host cell by experimental manipulations, such as those described herein, and may include gene sequences found in that organism provided that the introduced gene does not reside in the same location as does the naturally occurring gene. For example, a heterologous gene includes a gene from one species introduced into another species. A heterologous gene also includes a gene native to an organism that has been changed in some way (e.g., mutated, added in multiple copies, linked to a non-native promoter or enhancer sequence, etc.). Heterologous genes may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (e.g., genes expressed in loci where the gene is not normally expressed).

As used herein, the terms "homolog", "homologue", "homologous", and "homology" when used in reference to a polypeptide, protein, amino acid sequence, nucleic acid, or nucleotide refers to a degree of sequence identity to a given sequence, or to a degree of similarity between conserved regions, or to a degree of similarity between three-dimensional structures, or to a degree of similarity between the active site, or to a degree of similarity between the mechanism of action, or to a degree of similarity between functions. In some embodiments, a homolog has a greater than 30% sequence identity to a given sequence. In some embodiments, a homolog has a greater than 40% sequence identity to a given sequence. In some embodiments, a homolog has a greater than 60% sequence identity to a given sequence. In some embodiments, a homolog has a greater than 70% sequence identity to a given sequence. In some embodiments, a homolog has a greater than 90% sequence identity to a given sequence. In some embodiments, a homolog has a greater than 95% sequence identity to a given sequence. In some embodiments, homology is determined by comparing internal conserved sequences to a given sequence. In some embodiments, homology is determined by comparing designated conserved functional and/or structural regions, for example a domain, a low complexity region or a transmembrane region. In some embodiments, homology is determined by comparing designated conserved "motif" regions, such as a zinc finger domain motif. In some embodiments, means of determining homology are described in the Examples.

As used herein, the term "homology" when used in relation to nucleic acids or proteins refers to a degree of identity. There may be partial homology or complete homology. The following terms are used to describe the sequence relationships between two or more polynucleotides and between two or more polypeptides: "identity", "percentage identity", "identical", "reference sequence", "sequence identity", "percentage of sequence identity", and "substantial identity." "Sequence identity" refers to a measure of relatedness between two or more nucleic acids or proteins and is described as a given as a percentage "of homology" with reference to the total comparison length. A "reference sequence" is a defined sequence used as a basis for a sequence comparison; a reference sequence may be a subset of a larger sequence, for example, the sequence that forms an active site of a protein or a segment of a full-length cDNA sequence or may comprise a complete gene sequence, genome sequence, or portion of a genome sequence. Calculations of identity may be performed by algorithms implemented by computer programs such as the ClustalX algorithm (Thompson, Nucleic Acids Res. 24, 4876-4882 (1997)), incorporated herein by reference); MEGA2 (version 2.1) (Kumar, Bioinformatics 17, 1244-1245 (2001), incorporated herein by reference); "GAP" (Genetics Computer Group, Madison, Wis.), "ALIGN" (DNAStar, Madison, Wis.), BLAST (National Center for Biotechnology Information), and MultAlin (Multiple sequence alignment (Corpet, Nucl. Acids Res., 16 (22), 10881-10890 (1988), incorporated herein by reference). Alignment of sequences may be conducted by the local homology algorithm of Smith and Waterman (Smith and Waterman, Adv. Appl. Math. 2:482 (1981), incorporated herein by reference), by the homology alignment algorithm of Needleman and Wunsch (Needleman and Wunsch, J. Mol. Biol. 48:443 (1970), incorporated herein by reference), by the search for similarity method of Pearson and Lipman (Pearson and Lipman, Proc. Natl. Acad. Sci. U.S.A. 85:2444 (1988), incorporated herein by reference), by computerized implementations of these algorithms (GAP, BESTFIT, FASTA, and TFASTA in the Wisconsin Genetics Software Package Release 7.0, Genetics Computer Group, 575 Science Dr., Madison, Wis., incorporated herein by reference), or by inspection, and the best alignment (i.e., resulting in the highest percentage of homology over the comparison window) generated by the various methods is selected.

As used herein, the term "sequence identity" means that two polynucleotide or two polypeptide sequences are identical (i.e., on a nucleotide-by-nucleotide basis or amino acid-by-amino acid basis) over the window of comparison. The term "percentage of sequence identity" is calculated by comparing two optimally aligned sequences; determining the number of positions at which the identical nucleotide base (e.g., A, T, C, G, U, or I) or amino acid, in which often conserved amino acids are taken into account, occurs in both sequences to yield the number of matched positions; dividing the number of matched positions by the total number of positions in a window of comparison; and multiplying the result by 100 to yield the percentage of sequence identity. The term "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present technology.

As used herein, the term "ortholog" refers to a gene in different species that evolved from a common ancestral gene by speciation. In some embodiments, orthologs retain the same function. As used herein, the term "paralog" refers to genes related by duplication within a genome. In some embodiments, paralogs evolve new functions. In further embodiments, a new function of a paralog is related to the original function.

As used herein, the term "hybrid variety" refers to a substantially heterozygous hybrid line and minor genetic modifications thereof that retain the overall genetics of the hybrid line.

As used herein, the term "inbred" refers to a variety developed through inbreeding or doubled haploidy that preferably comprises homozygous alleles at about 95% or more of its loci. An inbred can be reproduced by selfing or growing in isolation so that the plants can only pollinate with the same inbred variety. While this approach is typically used for cross-pollinated crops (e.g., maize), it is generally not used for Proso because it naturally self-pollinates.

As used herein, the term "isolated" when used in relation to a nucleic acid or polypeptide, as in "an isolated oligonucleotide" or "an isolated polypeptide" refers to a nucleic acid or polypeptide that is identified and separated from at least one contaminant (e.g., nucleic acid and/or polypeptide with which it is ordinarily associated in its natural source). Isolated nucleic acid and/or polypeptide is present in a form or setting that is different from that in which it is found in nature. In contrast, non-isolated polypeptides and nucleic acids, such as DNA and RNA, are found in the state they exist in nature.

As used herein, the term "purified" refers to molecules, e.g., nucleic acids or polypeptides, that are removed from their natural environment. An "isolated nucleic acid sequence" is therefore a purified nucleic acid sequence and an "isolated polypeptide" is therefore a purified polypeptide. "Substantially purified" molecules are at least 60% free, preferably at least 75% free, and more preferably at least 90% free from other components with which they are naturally associated. As used herein, the terms "purified" and "to purify" also refer to the removal of contaminants from a sample.

As used herein, the term "linkage" refers to a phenomenon wherein alleles on the same chromosome tend to segregate together more often than expected by chance if their transmission was independent.

As used herein, the term "linkage disequilibrium" refers to a phenomenon wherein alleles tend to remain together in linkage groups when segregating from parents to offspring, with a greater frequency than expected from their individual frequencies.

As used herein, the term "locus" refers to a specific location on a chromosome, e.g., a defined segment of a DNA.

As used herein, the term "locus conversion" or "trait conversion" refers to plants within a variety that have been modified in a manner that retains the overall genetics of the variety and further comprises one or more loci with a specific desired trait, such as increased water efficiency. Examples of locus conversions include mutant genes, transgenes, and native traits finely mapped to a locus. One or more locus conversion traits may be introduced into a single Proso variety. In some embodiments, a "locus conversion" is a "single locus conversion". However, the term "locus conversion" is not limited to refer to a "single locus conversion" and thus the term "locus conversion" may refer to conversion of more than one locus (e.g., conversion of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 200, 300, 400, 500, 600, 700, 800, 900, 1000, or more than 1000 loci).

As used herein, the term "male sterile plant" refers to a plant that produces no viable pollen (no pollen that is able to fertilize the egg to produce a viable seed). Male sterility prevents self-pollination. Male sterile plants are therefore useful in hybrid plant production.

As used herein, the term "Nei distance" refers to a quantitative measure of percent similarity between two varieties. Nei distance between varieties A and B can be defined as 1-(2× number alleles in common)/(number alleles in A+number alleles in B). For example, if varieties A and B are the same for 95 out of 100 alleles, the Nei distance would be 0.05. If varieties A and B are the same for 98 out of 100 alleles, the Nei distance would be 0.02. Free software for calculating Nei distance is available on the internet at multiple locations. See, e.g., Proc Natl Acad Sci, 76:5269-73 (1979), incorporated herein by reference.

As used herein, the terms "nucleic acid", and "oligonucleotide" or "polynucleotide", refer to a molecule comprising two or more deoxyribonucleotides or ribonucleotides, preferably more than three, and usually more than ten. The exact size will depend on many factors, which in turn depends on the ultimate function or use of the nucleic acid. As used herein, the term "polynucleotide" refers to a molecule comprising several deoxyribonucleotides or ribonucleotides and is used interchangeably with oligonucleotide. Typically, oligonucleotide refers to shorter lengths of nucleic acids and polynucleotide refers to longer lengths of nucleic acids. The sequence of nucleotides in a nucleic acid is the "nucleotide sequence" of the nucleic acid.

As used herein, the terms "nucleotide sequence of interest" or "nucleic acid of interest" refer to any nucleic acid and/or nucleotide sequence (e.g., RNA or DNA), the manipulation of which may be deemed desirable for any reason (e.g., treat disease, confer improved qualities, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences that do not encode an mRNA or protein product (e.g., promoter sequence, polyadenylation sequence, termination sequence, enhancer sequence, etc.)

As used herein, the terms "protein" and "polypeptide" refer to molecules comprising amino acids joined via peptide bonds and are used interchangeably. A "protein" or "polypeptide" encoded by a gene is not limited to the amino acid sequence encoded by the gene but includes post-translational modifications of the protein. Where the term "amino acid sequence" is recited herein to refer to an amino acid sequence of a protein molecule, "amino acid sequence" and like terms such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein.

As used herein, the term "pedigree" refers to the lineage or genealogical descent of a plant.

As used herein, the term "pedigree distance" refers to the relationship among generations based on their ancestral links as evidenced in pedigrees. In some embodiments, pedigree distance is measured by the distance of the pedigree from a given starting point in the ancestry.

As used herein, the term "percent identity" refers to the comparison of the homozygous alleles of two Proso varieties. Percent identity is determined by comparing a statistically significant number of the homozygous alleles of two developed varieties. For example, a percent identity of 90% between Proso cultivar 1 and Proso cultivar 2 means that the two cultivars have the same allele at 90% of their loci.

As used herein, the term "percent similarity" refers to the comparison of the homozygous alleles of a Proso cultivar (e.g., Proso cultivar DLG40 or DLG240) with another plant, and if the homozygous allele of the Proso cultivar matches at least one of the alleles from the other plant, then they are scored as similar. Percent similarity is determined by comparing a statistically significant number of loci and recording the number of loci with similar alleles as a percentage. A percent similarity of 90% between a Proso cultivar and another plant means that the Proso cultivar matches at least one of the alleles of the other plant at 90% of the loci.

As used herein, the term "plant" is used in its broadest sense. The term "plant" includes, but is not limited to, any species of grass (e.g., turf grass), ornamental or decorative, crop or cereal (e.g., Proso), fodder or forage, fruit or vegetable, fruit plant or vegetable plant, herb plant, woody plant, flower plant or tree. The term "plant" is not meant to limit a plant to any particular structure. The term "plant" also refers to a unicellular plant (e.g., microalga) and a plurality of plant cells that are largely differentiated into a colony (e.g., volvox) or a structure that is present at any stage of plant development. Such structures include, but are not limited to, a seed, a tiller, a sprig, a stolen, a plug, a rhizome, a shoot, a stem, a leaf, a flower petal, a fruit, etc. As used herein, the term "plant" includes reference to an immature or mature whole plant, including a plant from which seed or grain has been removed. Seed or embryo that will produce the plant is also considered to be the plant. The terms "crop" and "crop plant" are used herein in their broadest sense. The term "crop" or "crop plant" includes, but is not limited to, any species of plant or alga edible by humans or used as a feed for animals or fish or marine animals, or consumed by humans, or used by humans (natural pesticides), or viewed by humans (flowers), or any plant or alga used in industry or commerce or education.

As used herein, the term "plant part" (e.g., a "Proso plant part") refers to a plant structure or a plant tissue, for example, pollen, an ovule, a tissue, a pod, a seed, a leaf (e.g., a flag leaf), or a cell. Plant parts may comprise one or more of a tiller, plug, rhizome, sprig, stolen, meristem, crown, a ligule, a node, a leaf sheath, a leaf blade, internode, panicle, pillow, and the like. In some embodiments, plants are crop plants.

Proso leaves comprise a sheath (the basal portion of the leaf wrapped tightly around the stem) and a blade (the flat portion extending away from the stem). The ligule is a thin collar of filmy tissue that grows semi-perpendicularly at the junction of the leaf sheath and the leaf blade on the adaxial (upper) surface of the leaf. Nodes are slightly swollen regions along the length of a stem from which leaves, branches, and/or aerial roots emerge. An internode is the portion of the stem between nodes. A panicle is a branched inflorescence in which each branch has more than one flower. Pillows are small bulged portions of plant tissues at the junction of the primary branch and main axis of the panicle.

As used herein, the term "plant tissue" refers to differentiated and undifferentiated tissues of plants including but not limited to protoplasts, leaves, stems, roots, root tips, anthers, pistils, seed, grain, embryo, pollen, ovules, cotyledon, hypocotyl, pod, flower, shoot, tissue, petiole, cells, meristematic cells, tumors, and plant cells in culture (e.g., single cells, protoplasts, embryos, callus, etc.). Plant tissue may be in planta, in organ culture, tissue culture, or cell culture.

As used herein, the term "platform" refers to the variety with the base genetics and the variety with the base genetics comprising locus conversion(s). There can be a platform for an inbred Proso variety and/or a hybrid Proso variety.

As used herein, the term "progeny" includes an $F_1$ Proso plant produced from the cross of two Proso plants and progeny further includes, but is not limited to, subsequent $F_2$, $F_3$, $F_4$, $F_5$, $F_6$, $F_7$, $F_8$, $F_9$, and $F_{10}$ generational crosses with a recurrent parental line.

As used herein, the term "propagation" refers to the process of producing new plants, either by vegetative means involving the rooting or grafting of pieces of a plant, or by sowing seeds. The terms "vegetative propagation" and "asexual reproduction" refer to the ability of plants to reproduce without sexual reproduction, e.g., by producing new plants from existing vegetative structures that are clones, i.e., plants that are identical in all attributes to the parent plant and to one another. For example, the division of a clump, rooting of proliferations, or cutting of mature crowns can produce a new plant.

As used herein, the terms "tissue culture" and "micropropagation" refer to a form of asexual propagation undertaken in specialized laboratories, in which clones of plants are produced from small cell clusters from very small plant parts (e.g. buds, nodes, leaf segments, root segments, etc.) and grown aseptically (free from any microorganism) in a container where the environment and nutrition can be controlled.

As used herein, the term "quantitative trait loci" (QTL) refer to genetic loci that control to some degree numerically representable traits that are usually continuously distributed.

As used herein, the term "regeneration" refers to the development of a plant from tissue culture.

As used herein, the term "sample" is used in its broadest sense. In one sense it can refer to a plant cell or tissue, such as a leaf. In another sense, it is meant to include a specimen or culture obtained from any source, as well as biological and environmental samples. Biological samples may be obtained from plants or animals and encompass fluids, solids, tissues, and gases. Environmental samples include environmental material such as surface matter, soil, water, salt, and industrial samples. These examples are not to be construed as limiting the sample types applicable to the present technology.

As used herein, the term "seed" refers to a fertilized and ripened ovule comprising the plant embryo, stored food material, and a protective outer seed coat. The term "seed" is synonymous with the term "grain".

As used herein, the term "seed yield", e.g., expressed in units of bushels/acre or pounds/acre, refers to the actual yield of the grain at harvest.

As used herein, the term "higher-yielding Proso" refers to a Proso variety that has a higher seed yield than a conventional Proso variety (e.g., Huntsman, Earlybird, Horizon, Sunrise, Sunup, Plateau, Dove, Cerise) when both are grown under substantially and/or essentially the same conditions (e.g., amounts of water, light, nutrients, and/or spacing) or when each is grown under different conditions (e.g., amounts of water, light, nutrients, and/or spacing). In some embodiments, the yields of the higher yielding Proso variety and the conventional Proso variety (e.g., check variety) are maximized by growing each of the higher-yielding Proso variety and the conventional Proso variety (e.g., check variety) under conditions that are specific for the variety. Accordingly, in some embodiments, the higher-yielding Proso variety is grown under conditions appropriate to maximize yield of the higher-yielding Proso variety and the conventional Proso variety (e.g., check variety) is grown under conditions appropriate to maximize yield of the conventional variety.

Nevertheless, the term "higher-yielding Proso" can refer to a Proso variety that has a higher seed yield than a conventional Proso variety (e.g., Huntsman, Earlybird, Horizon, Sunrise, Sunup, Plateau, Dove, Cerise) when each is grown under different conditions (e.g., amounts of water, light, nutrients, and/or spacing), e.g., when each is grown using conditions to maximize yield of each of the higher yielding and conventional varieties.

As used herein, the term "self-pollination" refers to a pollination process in which pollen from one flower is transferred to the same or another flower of the same plant.

As used herein, the term "sib pollination" refers to a pollination process in which individuals within the same family or variety are used for pollination.

As used herein, the term "SNP" or "single nucleotide polymorphism" refers to a DNA sequence variation that occurs when a single nucleotide in the genome differs between individual plant or plant varieties. The differences can be equated with different alleles and indicate polymorphisms. A number of SNP markers can be used to determine a molecular profile of an individual plant or plant variety and can be used to compare similarities and differences among plants and plant varieties.

As used herein, the term "SSR" refers to a genetic marker based on polymorphisms in repeated nucleotide sequences, such as microsatellites. A marker system based on SSRs can be informative in linkage analysis relative to other marker systems in that multiple alleles may be present.

As used herein, the term "trait" in reference to a plant refers to an observable and/or measurable characteristic of an organism, such as yield.

As used herein, the term "transgene" refers to a heterologous gene that is placed into an organism or host cell by the process of transfection.

As used herein, the term "transgenic", when used in reference to a plant or leaf or fruit or seed or plant part (e.g., a "transgenic plant", "transgenic leaf", "transgenic fruit", "transgenic seed", or "transgenic host cell"), refers to a plant or leaf or fruit or seed or plant part or cell that comprises at least one heterologous gene in one or more of its cells. The term "transgenic plant material" refers broadly to a plant, a plant structure, a plant tissue, a plant seed, or a plant cell that comprises at least one heterologous gene in one or more of its cells. Accordingly, the term "non-transgenic" or "transgene free" refers to a plant or leaf or fruit or seed or plant part or cell that does not comprise a heterologous gene in one or more of its cells.

As used herein, the term "variety" refers to a Proso line and minor genetic modifications thereof that retain the overall genetics of the line including but not limited to a locus conversion, a mutation, or a somoclonal variant. For example, the term "variety" may refer to a biological classification for an intraspecific group or population that can be distinguished from the rest of the species by any characteristic (for example morphological, physiological, cytological, genotypic, etc.) A variety may originate in the wild but can also be produced through selected breeding (for example, see "cultivar"). As used herein, the term "cultivar", "cultivated variety", and "cv" refer to a group of cultivated plants distinguished by any characteristic (for example morphological, physiological, cytological, genotypic, etc.) that when reproduced (e.g., sexually or asexually) retain their distinguishing features to produce a cultivated variety.

As used herein, the term "water efficiency" refers to a measure of water use by a plant per unit of yield. For example, water efficiency can be expressed in terms of yield of seed in units of bushels/acre per gallon of water, yield of seed in units of pounds/acre per acre-inch of water, etc.

As used herein, the term "wild-type" when made in reference to a gene refers to a functional gene common throughout an outbred population. As used herein, the term "wild-type" when made in reference to a gene product refers to a functional gene product common throughout an outbred population. A functional wild-type gene is that which is most frequently observed in a population and is thus arbitrarily designated the "normal" or "wild-type" form of the gene.

As used herein, the term "modified" or "mutant" when made in reference to a gene or to a gene product refers, respectively, to a gene or to a gene product that displays modifications in sequence and/or functional properties (i.e., modified or altered characteristics) when compared to the wild-type gene or gene product. Thus, the terms "variant" and "mutant" when used in reference to a nucleic acid refer to a nucleotide sequence that differs by one or more nucleotides from another, usually related nucleotide sequence. A "variation" is a difference between two different nucleotide sequences; typically, one nucleotide sequence is a reference sequence.

As used herein, the term "yield" refers to the amount of grain harvested, e.g., expressed in pounds per unit area of land.

As used herein, the term "yield advantage" refers to the yield advantage of variety 1 over variety 2 as calculated by: (YIELD of variety 1-YIELD variety 2)=YIELD ADVANTAGE of variety 1 (e.g., a "differential yield advantage" or "absolute yield advantage" expressed as N where N is the result of the calculation, YIELD of variety 1 and YIELD variety 2 are expressed in the same units, and N has the same units as YIELD of variety 1 and YIELD variety 2).

A "yield advantage" may also be calculated as a ratio or a factor using (YIELD of variety 1/YIELD variety 2)=YIELD ADVANTAGE of variety 1 (e.g., "a factor yield advantage" or "relative yield advantage" expressed as N× where N is the result of the calculation and N× is unitless assuming YIELD of variety 1 and YIELD variety 2 are expressed in the same units).

As used herein, the term "growing degree days" (GDD) refers to a growth rate and/or development rate of a Proso plant. GDD are calculated from the air temperature for each day and accumulated from the time the Proso is planted. In some embodiments, GDD is calculated as GDD=(maximum temperature+minimum temperature)/(2-50). In some calculations, if the minimum temperature is less than 50° F. or above 86° F., 50° F. or 86° F. is used.

As used herein, the term "flag leaf" refers to the last leaf to emerge on a Proso plant.

As used herein, the term "flag leaf attitude of blade" refers to the position of the blade of the flag leaf relative to the stem (e.g., vertical, horizontal or semi-vertical).

As used herein, the term, "anthocyanin coloration" refers to the anthocyanin-like pigmentation in a plant part (e.g., a leaf (e.g., a leaf blade), glumes, etc.). In some embodiments, anthocyanin coloration is scored for a plant or plant part (e.g., leaf (e.g., leaf blade), glumes, etc.) as "present" or "absent".

As used herein, the term "intensity of anthocyanin coloration" refers to the strength and/or quality of anthocyanin-like pigmentation in a leaf (e.g., a leaf blade). In some embodiments, the intensity of anthocyanin coloration is scored for a plant (e.g., for a leaf (e.g., for a leaf blade) as "weak", "medium", or "strong".

As used herein, the term "flag leaf length" refers to the distance (e.g., in centimeters) from the beginning of the ligule to the tip of the leaf blade.

As used herein, the term "flag leaf width" refers to the maximum width (e.g., in centimeters) of the flag leaf.

As used herein, the term "number of nodes" refers to the number slightly swollen regions ("nodes") along the length of a stem from which leaves, branches, and/or aerial roots emerge.

As used herein, the term "length of upper internode" refers to the length (e.g., in centimeters) from the topmost node to the attachment point of the lowest primary panicle branch to the main panicle axis.

As used herein, the term "thickness of internode" refers to the thickness (e.g., in centimeters) across the middle of an internode, which is the portion of the stem between nodes. In some embodiments, the thickness of internode is measured at the middle internode on a stem. For an odd number of nodes N, the middle node is internode number $[(N/2)+0.5]$. For an even number of nodes N, the middle node is internode number $(N/2)$ or $[(N/2)+1]$. For example, if a plant has 5 internodes, then the 3rd internode from the base is used for the measurement. If a plant has 6 internodes, then either the 3rd or 4th internode from the base is used for the measurement.

As used herein, the term "time of panicle emergence" or "heading date" refers to the number of days after planting when the first panicle spikelet is visible in 50% of plants.

As used herein, the term "natural height" or "plant height" refers to the perpendicular distance (e.g., in centimeters) from the soil at the plant base to the highest point reached while all plant parts are in their natural positions.

As used herein, the term "angle of panicle branches" refers to the position of primary panicle branches relative to the panicle axis (e.g., vertical, horizontal, or semi-vertical).

As used herein, the term "panicle attitude" refers to the degree of curvature of the main panicle axis relative to the stem.

As used herein, the term "panicle length (excluding peduncle)" is the length (e.g., in centimeters) of the inflorescence from its base (the attachment point of the lowest primary branch) to the tip.

As used herein, the term "panicle width" refers to the maximum width (e.g., in centimeters) of the inflorescence.

As used herein, the term "panicle density" refers to the ratio of the number of primary branches to the length of the primary axis of the panicle.

As used herein, the term "degree of curvature of lateral branches" refers to the central angle formed by secondary branches relative to the rachis of the primary branches.

As used herein, the term "number of pillows" refers to the number of small bulged portions of plant tissues at the junction of the primary branch and main axis of the panicle ("pillows").

As used herein, the term "length of primary branches" refers to the distance (e.g., in centimeters) between the junction of the main panicle axis and a primary branch selected in the middle of panicle to the tip of that branch.

As used herein, the term "spikelet shape" refers to the external form, structure, and/or outline of a grass flower, which comprises a pistil and stamens enclosed by two bracts, the lemma, glumes, and the palea.

As used herein, the term "stigma color" refers to the pigmentation of the distal portion of the style (the female reproductive organ).

As used herein, the term "grain size" refers to the distance (e.g., in millimeters) of the longest axis of grains (seeds) with hulls.

As used herein, the term "grain shape" refers to the form and/or structure of ripe grains (seeds) with hulls.

As used herein, the term "grain color" refers to the strength and/or quality of pigmentation of the hulls of grains (seeds).

As used herein, the term "grain presence of spotting" refers to the presence or absence of pigmentation in the form ridges or spots on the hull of grains (seeds).

As used herein, the term "grain size of spots" refers to the relative size difference of color pigmentation on the hulls of grains (seeds). Color pigmentations may appear in shapes (e.g., approximately round shapes) of different sizes and/or diameters. In some embodiments, the grain size of spots is described using categorical or relative terms of small, medium, or large.

As used herein, the term "weight per 1000 grains" refers to the weight (e.g., in grams) of 1,000 mature seeds (with hulls).

As used herein, the term "kernel color (not polished)" refers to the color pigmentation of the edible central portion of the grain (seed) following removal of the hull.

As used herein, the term "intensity of brown color of placental spots" refers to the relative strength and/or quality difference in the intensity of brown color pigmentation present at the point of attachment of ovules inside the ovary.

As used herein, the term "kernel type of endosperm" refers to the type of starch in milled grain, typically as determined via the iodine color reaction. For example, waxy or glutinous starch contains high levels of amylopectin and non-waxy starch contains low levels of amylopectin).

As used herein, the term "test weight" refers to the weight of grain (e.g., measured in pounds) per bushel.

Breeding Methods

In some embodiments, the technology described herein is also directed to methods for producing a plant (e.g., a Proso plant) by crossing a first parent Proso plant as described herein (e.g., DLG40, DLG240, DLG148, and/or DLG149) with a second parent Proso plant. In some embodiments, the technology described herein relates to use of genotyping-by-sequencing (e.g., tunable genotyping-by-sequencing (e.g., as described in U.S. Pat. Nos. 9,951,384 and 10,704,091, each of which is incorporated herein by reference)) for breeding plants. For example, in some embodiments, tunable genotyping-by-sequencing is used to confirm progeny of a cross, to identify plants for crosses, to select plants for crosses, and/or to identify genetic markers associated with desirable phenotypes (e.g., yield). In some embodiments, the technology described herein relates to use of genotyping-by-sequencing (e.g., tunable genotyping-by-sequencing (e.g., as described in U.S. Pat. Nos. 9,951,384 and 10,704,091, each of which is incorporated herein by reference)) for breeding Proso plants. However, the technology is not limited to breeding Proso plants and finds use in any plant breeding method (e.g., for plants having a sequenced genome for use as a reference).

Uses

In some embodiments, the Proso varieties described herein find use in animal feed, e.g., for bird and livestock feed and/or in pet food. In some embodiments, the Proso varieties described herein find use in completely or partially replacing corn used in feed for beef cattle, poultry (e.g., turkeys, chickens), and hogs. In some embodiments, the Proso varieties described herein find use in completely or partially replacing corn used in pet food. In some embodiments, the Proso varieties described herein find use as forage or hay. In some embodiments, Proso finds use as a food for humans.

In some embodiments, the Proso varieties find use in producing a biofuel. In some embodiments, the Proso varieties provided herein find use in producing an ethanol for human consumption. In some embodiments, the Proso varieties provided herein find use in producing an ethanol for commercial and/or industrial use. For example, in some embodiments, Proso produces approximately 2.2 gallons or more of ethanol per bushel.

Although the disclosure herein refers to certain illustrated embodiments, it is to be understood that these embodiments are presented by way of example and not by way of limitation.

Examples

Breeding Program

During the development of embodiments of the technology described herein, an experimental breeding program was used to produce novel varieties of Proso. During these experiments, the breeding program screened thousands of potential lines to produce and identify new Proso varieties having improved phenotypes, e.g., higher yields, improved lodging tolerance, and other desirable agronomic characteristics.

Plants were grown in a plant growth facility. The plant growth facility was used to grow proso millet parental lines for crossing, to advance new populations, and to increase seed. The plant growth facility did not have any windows and light was provided by light emitting diodes.

The breeding program was established by collecting Proso germplasm from the USDA. From the germplasm that was received, 50 genetically diverse lines (including 6 "founder lines") were selected to use for crosses. Female flowers were emasculated and they were cross pollinated with selected male flowers to generate $F_1$ seed. Currently the breeding program is at an advanced stage and crosses are mostly made between pairs of elite lines.

The breeding program successfully addressed several challenges associated with making crosses between Proso lines. During the development of embodiments of the technology provided herein, data collected during the breeding and characterization of plants indicated that some fractions of the resulting seeds were "false positive" $F_1$s (e.g., were not progeny of the presumptive male parent). Accordingly, during the development of embodiments of the technology, the breeding program comprised having experiments conducted to check the correctness of parental assignments of putative $F_1$ plants using DNA markers (e.g., using genotyping-by-sequencing). In particular, true $F_1$ plants were grown in the plant growth facility, bagged, and selfed to generate $F_2$ seed. Further selfing generations (e.g., $F_2, F_3, F_4, F_5, F_6$, etc.) were completed in the plant growth facility. A single seed descent method (SSD) was followed from $F_2$ to one or more subsequent generations (e.g., to the $F_3, F_4, F_5$, and/or $F_6$ generation). For every population derived from a single $F_1$ plant, the breeding program was initiated with 384 $F_2$ plants. When a line reached the $F_5$ or $F_6$ generation (e.g., with an expected percentage homozygosity of more than 95%), plants with white seed color (which is desirable in the marketplace) and compact panicle type (which is preferred by farmers) were selected by visual observation. This screening significantly reduced the number of new lines by approximately 90%. This screening increased efficiency and maximized resource utilization to advance the best potential lines in the next stage of evaluation. Furthermore, in some embodiments, the breeding program comprises having genomic selection (GS) conducted and phenotypic scoring conducted to predict lines having desirable agronomic traits (e.g., having a desirable (e.g., improved) yield). In some embodiments, the breeding program comprises performing genomic selection (GS) and performing phenotypic scoring to predict lines having desirable agronomic traits (e.g., having a desirable (e.g., improved) yield).

A single seed of each of the selected lines was planted in a 6"×4" pot. The panicle of each individual plant was harvested separately to grow it as a single head row in the summer nursery. The head rows were planted as a non-replicated single 5' to 8' long row in fields field at Gilbert, Iowa; Sidney, Nebraska; and Akron, Colorado. In the field, head rows were scored for different traits such as flowering time (also called heading date), plant height, panicle type, panicle length, lodging tolerance, and physiological maturity. Post-harvest, seed color, grains per panicle, and 1,000 grain weight were scored. These phenotypic selections were used to reduce the number of lines by approximately 90%. Individual panicle heads of these 200 lines were harvested and the seed was cleaned for subsequent planting.

Subsequently, selected lines (e.g., 50, 100, 200, or more) were sent to Chile for seed increase during the winter season. In Chile, a contractor grew the seed as a small plot (8-foot·long×4 rows). Each plot was harvested by hand, the harvest was cleaned with a thrasher, and the seed was returned.

A contract statistician developed an experimental design to test each line in replicated yield plot trials in target environments (e.g., Colorado and Nebraska). The experimental design considered seed availability for each line and other factors. Seed packets were prepared (based on the experimental design) by measuring required seed amount, arranging the seed according to the experimental design, and shipping the seed to contractor growers (e.g., in target areas such as Colorado, Nebraska, South Dakota). The contract growers sowed seeds in small trial plots (30-foot-long× 5-foot-wide) at different locations (e.g., Burlington, Colorado; Fleming, Colorado; Akron, Colorado; and Sidney, Nebraska) in June of each year. Approximately 300-1200 plots were grown at each location. Contractors collected data (e.g., flowering time, plant height, and yield). Plots were visited in August (or close to physiological maturity) to score plants for other agronomic traits (e.g., uniformity, agronomic desirability, panicle type, lodging tolerance, maturity, and yield). Contractors harvested the plots and provide yield and other trait data. These data were analyzed to identify the highest yielding lines using a spatial correction model. The seeds for the highest yielding line(s) were sent to Chile to plant ¼-acre foundation seed increase plot(s).

Once the harvested foundation seed was returned from Chile, it was sent to a lab for germination and purity analyses. Varieties were certified based on field inspection reports and lab results. After seed certification, the certified varieties were planted for further foundation seed increase in target environments (e.g., in Colorado and Nebraska) in 5-10 acre plots. These plots were grown with plot isolation distances (e.g., to avoid cross pollination) according to state certification agency rules and guidelines. Contractors maintained strict quality control during harvesting and seed processing. At this stage, enough seed was produced for certified seed increase on a larger scale (500 acres or more), e.g., for commercial sales to farmers.

Breeding Histories

The breeding histories of the higher-yielding Proso varieties DLG240 (also known as "DLG-0024256"), DLG40 (also known as "DLG-0024888"), DLG148 (also known as "DLG-0024884"), and DLG149 (also known as "DLG-0025078") are summarized below. DLG240

The cross between PI 463225 and PI 578074 was made at Ames, Iowa in August to September 2015. The $F_1$ plant of this cross was grown from October to December 2015. A DNA based marker genotyping technology (e.g., genotyping-by-sequencing) was used to ensure that it was a true $F_1$. In addition, the same $F_1$ plant was compared with the original parents for phenotypic data comparison. The $F_2$, $F_3$, $F_4$, and $F_5$ generations of this cross were grown and advanced using a single seed decent (SSD) method at a plant growth room located at Iowa State University Research Park at Ames, Iowa.

In January 2017 a total of 16 $F_5$ plants from this cross were sown and harvested as a bulk seed ($F_5$:$F_6$ line). This bulked $F_5$:$F_6$ line was grown in the field as 8-foot-long head rows with replications in Sidney, NE and Akron, CO from June 2017 to September 2017. A single $F_5$:$F_6$ head row designated as DLG240 was selected based on uniformity, panicle type, yield, and was harvested as a bulk seed ($F_5$:$F_7$ seed) for seed purification and seed increase purpose. The harvested bulk $F_5$:$F_7$ seed were checked for any seed color segregation and any contaminant seed not of white color was removed. This $F_5$:$F_7$ seed was sent to Chile in November 2017 to March 2018 for seed increase where it was grown as a single four row plot (8-foot long rows with a 1 foot distance between each row) under drip irrigation. In March 2018 the increased $F_5$:$F_8$ seed were received.

During the summers of 2018, 2019, and 2020, DLG240 was evaluated in replicated yield trials under rainfed (dryland) production conditions at multiple locations across Colorado and Nebraska, which are current the major production areas for this crop in the United States. DLG240 was selected because of its high yield potential, medium maturity, white seed color, large seed size, compact panicle type, and overall agronomic desirability. This variety has been tested in Colorado and Nebraska and has shown excellent yield performance across the region relative to currently grown popular check cultivars. DLG240 exhibited no lodging in any location during these years. Based on visual observation, no insect or disease infestation was found. This variety finds use for dryland proso millet production. DLG240 received foundation seed certification in 2019 and 2020, and certified seed certification in 2020. The foundation seed plot in Sidney NE was in the $F_5$:$F_{10}$ generation.

DLG40

The cross between PI 578073 and PI 250786 was made at Ames, Iowa in August to September 2015. The $F_1$ plant of this cross was grown from October to December 2015. A DNA based marker genotyping technology (e.g., genotyping-by-sequencing) was used to ensure that it was a true $F_1$. In addition, the same $F_1$ plant was compared with the original parents for phenotypic data comparison. The $F_2$, $F_3$, and $F_4$ generations of this cross were grown and advanced using a single seed decent (SSD) method at a plant growth room located at Iowa State University Research Park at Ames, Iowa.

In January 2017 a total of 16 $F_4$ plants from this cross were sown and harvested as a bulk seed ($F_4$:$F_5$ line). This bulked $F_4$:$F_5$ line was grown in the field as 8-foot-long head rows with replications in Sidney, NE and Akron, CO from June 2017 to September 2017. A single $F_4$:$F_5$ head row designated as DLG40 was selected based on uniformity, panicle type, yield, and was harvested as a bulk seed ($F_4$:$F_6$ seed) for seed purification and seed increase purpose. The harvested bulk $F_4$:$F_6$ seed were checked for any seed color segregation and any contaminant seed not of white color was removed. This $F_4$:$F_6$ seed was sent to Chile in November 2017 to March 2018 for seed increase where it was grown as a single four row plot (8-foot long rows with a 1-foot distance between each row) under drip irrigation. In March 2018 the increased $F_4$:$F_7$ line seed was received.

During the summers of 2018, 2019, and 2020, DLG40 was evaluated in replicated yield trials under rainfed (dryland) production conditions at multiple locations across Colorado and Nebraska. DLG40 was selected because of its high yield potential, medium maturity, white seed color, large seed size, compact panicle type, and overall agronomic desirability. This variety has been tested in Colorado and Nebraska and has shown excellent yield performance across the region relative to currently grown popular check cultivars. DLG40 exhibited no lodging in any location during these years. Based on the visual observation, no insect or disease infestation was found. This variety finds use for dryland proso millet production. DLG40 received foundation seed certification in 2019 and 2020, and certified seed certification in 2020. The foundation seed plot in Sidney NE was in the $F_4$:$F_9$ generation.

DLG148

The cross between PI 578073 and PI 250786 was made at Ames, Iowa in August to September 2015. The $F_1$ plant of this cross was grown in a greenhouse from October to December 2015. A DNA based marker genotyping technology (e.g., genotyping-by-sequencing) was used to ensure that it was a true $F_1$. In addition, the same $F_1$ plant was compared with the original parents for phenotypic data comparison. The $F_2$, $F_3$, and $F_4$ generations of this cross were grown and advanced using a single seed decent (SSD)

method at a plant growth room located at Iowa State University Research Park at Ames, Iowa.

In January 2017 a total 16 $F_4$ plants were sown and harvested as a bulk seed ($F_4$:$F_5$ line). This bulked $F_4$:$F_5$ line was grown in a field as 8-foot-long head rows with replications in Sidney, NE and Akron, CO from June 2017 to September 2017. A single $F_4$:$F_5$ head row designated as DLG148 was selected based on uniformity, panicle type, and yield, and was harvested as a bulk seed ($F_4$:$F_6$ seed) for seed purification and seed increase. The harvested bulk $F_4$:$F_6$ seed were checked for any seed color segregation and any contaminant seed not of white color was removed. This $F_4$:$F_6$ seed was sent to Chile in November 2017 to March 2018 for seed increase where it was grown as a single four row plot (8-foot-long rows with 1-foot distance between each row) under drip irrigation. In March 2018 the increased $F_4$:$F_7$ seed were received.

In summer of 2018, 2019, and 2020, DLG148 was evaluated in replicated yield trials under rainfed (dryland) production conditions in different locations across Colorado and Nebraska. DLG148 was selected because of its high yield potential, early maturity, white seed color, seed size, compact panicle, and overall agronomic desirability. This variety has been tested in Colorado and Nebraska and has shown excellent yield performance across the region relative to currently grown popular check cultivars. DLG148 showed no lodging in any location during these years. Based on the visual observation, no insect or disease infestation was found. This variety finds use for dryland proso millet production. DLG148 received foundation seed certification in 2019. The foundation seed plot in Chile was in the $F_4$:$F_8$ generation, and Matheson CO was in the $F_4$:$F_9$ generation.

DLG149

The cross between PI 578073 and PI 250786 was made in a greenhouse in Ames, IA in August to September 2015. The $F_1$ plant of this cross was grown in a greenhouse from October to December 2015. A DNA based marker genotyping technology (e.g., genotyping-by-sequencing) was used to ensure that it was a true $F_1$. In addition, the same $F_1$ plant was compared with the original parents for phenotypic data comparison. The $F_2$, $F_3$, and $F_4$ generations of this cross were grown and advanced using a single seed decent (SSD) method from January 2016 to December 2016 at a plant growth room located at Iowa State University Research Park at Ames IA.

In January 2017 a total 16 $F_4$ plants were sown and harvested as a bulk seed ($F_4$:$F_5$ line). This bulked $F_4$:$F_5$ line were grown in a field as 8-foot-long head rows with replications in Sidney, NE and Akron, CO from June 2017 to September 2017. A single $F_4$:$F_5$ head row designated as DLG149 was selected based on uniformity, panicle type, and yield, and was harvested as a bulk seed ($F_4$:$F_6$ seed) for seed purification and seed increase. The harvested bulk $F_4$:$F_6$ seed were checked for any seed color segregation and any contaminant seed not of white color was removed. This $F_4$:$F_6$ seed was sent to Chile in November 2017 to March 2018 for seed increase where it was grown as a single four row plot (8-foot-long rows with 1-foot distance between each row) under drip irrigation. In March 2018 the increased $F_4$:$F_7$ seed were received.

In summer of 2018, 2019, and 2020, DLG149 was evaluated in replicated yield trials under rainfed (dryland) production conditions in different locations across the Colorado and Nebraska. DLG149 was selected because of its high yield potential, medium maturity, white seed color, seed size, compact panicle, and overall agronomic desirability. This variety has been tested in Colorado and Nebraska and has shown excellent yield performance across the region relative to currently grown popular check cultivars. DLG149 showed no lodging in any location across the years. Based on the visual observation, no insect or disease infestation was found. This variety finds use for dryland proso millet production. DLG149 received foundation seed certification in 2019. The foundation seed plot in Chile was in $F_4$:$F_8$ generation, and Matheson CO was in the $F_4$:$F_9$ generation.

Phenotypic Characteristics

The phenotypic characteristics of the higher-yielding Proso varieties are summarized below. Phenotypic traits were scored using the UPOV guidelines and photographs for proso millet. Burlington 2020 yield numbers for all four varieties reported below were calculated from reps that produced at least 2 pounds of harvested seed (to increase the accuracy of the yield data). Huntsman yield numbers reported below in all foundation plot yield tables are from commercial production plots in the grower's field.

DLG240

Tables 1 and 2 provide a detailed description of the morphological, physiological, and other characteristics of the DLG240 plants and seed that distinguish it from other varieties. In 2019, 30 plants of DLG240 and various commercial cultivars were space planted to collect the detailed data on each at Gilbert, IA (Table 1) and Ventura, IA (Table 2). The Gilbert Iowa trial was planted on Jun. 14, 2019 and harvested between Sep. 3-20, 2019. The Ventura, Iowa trial was planted on Jun. 20, 2019 and harvested between Sep. 3-20, 2019. These data were collected between June to September of 2019.

Tables 3A and 3B provide comparative yield data and other characteristics identifying the variety. Table 3A provides a summary of proso millet small plot yield trials grown during 2018-2020 in Colorado and Nebraska. Table 3B provides a summary of proso millet foundation and certified plots grown from 2019-2020 in Colorado and Nebraska.

Tables 4-8 provide a trait data comparison between DLG240 and other known released check varieties. Table 4A provides a summary of average grain yield (lbs/ac) based on dry weight basis of variety DLG240 as compared to commercial proso millet cultivars grown at various Colorado and Nebraska locations from 2018 to 2020 in small yield plot trials planted as per Table 3A. Yield/acre was calculated using small plot trial data, adjusted for grain moisture. Table 4B provides a summary of average grain yield (lbs/ac) based on GPS adjusted mean (spatially variation adjustment) of variety DLG240 as compared to commercial proso millet cultivars grown at various Colorado and Nebraska locations from 2018-2020 in small yield plot trials planted as per Table 3A. Yield/acre was calculated using small plot trial data and adjusted for grain moisture. Table 4C provides a summary of average as-is grain yields (lbs/ac) of DLG240 and Huntsman from foundation plots grown at various locations in Colorado and Nebraska during 2019-

2020 planted as per Table 3B. Table 5 provides a summary of average test weight (pounds per bushel) of DLG240 and commercial checks at various locations in Colorado and Nebraska in small yield plot trials grown from 2018 to 2020 planted as per Table 3A. Table 6 provides data for average heading date (days) of DLG240 and commercial checks (Dawn, Earlybird, Huntsman, Horizon, Plateau, Sunup) at Akron, CO and Sidney, NE in 2018 and 2020 small 5 plot trials planted as per Table 3A. Table 7 provides data for average plant height (cm) of DLG240 and commercial checks (Dawn, Earlybird, Huntsman, Horizon, Plateau, Sunup) at Akron, CO and Sidney, NE locations in 2018 and 2020 small plot trials planted as per Table 3A. Table 8 provides the average 1000 grain weight (in grams) of DLG240 and commercial checks (Dawn, Earlybird, Huntsman, Horizon, Plateau, Sunup) in 2018 yield plot trials planted as per Table 3A.

TABLE 1

DLG240 Gilbert IA

| Sr. | Trait | DLG240 | Dawn | Earlybird | Horizon |
|---|---|---|---|---|---|
| 1 | Flag leaf attitude of blade | Semi erect | Semi erect | Semi erect | Semi erect |
| 2 | Flag leaf anthocyanin coloration | Absent | Absent | Absent | Absent |
| 3 | Flag leaf intensity of anthocyanin coloration | Absent | Absent | Absent | Absent |
| 4 | Flag leaf length (cm) | 25.7 | 23.4 | 27.9 | 27.8 |
| 5 | Flag leaf width (cm) | 2.08 | 1.78 | 1.83 | 2.86 |
| 6 | Number of internodes | 6 | 4 | 5 | 5 |
| 7 | Length of upper internode (cm) | 14.07 | 13.45 | 15.64 | 14.15 |
| 8 | Thickness of internodes (cm) | 0.54 | 0.45 | 0.67 | 0.69 |
| 9 | Time of panicle emergence (days) | 41 | 26 | 37 | 37 |
| 10 | Natural height (cm) | 104.58 | 78.8 | 106.32 | 99.03 |
| 11 | Angle of panicle branches | Very acute | Very acute | Very acute | Very acute |
| 12 | Panicle attitude | Semi erect | Semi erect | Semi erect | Semi erect |
| 13 | Panicle length, excluding peduncle (cm) | 20.96 | 19.38 | 22.1 | 21.35 |
| 14 | Panicle width(cm) | 5.06 | 4.82 | 5.45 | 4.49 |
| 15 | Panicle density | Dense | Dense | Dense | Dense |
| 16 | Degree of curvature of lateral branches | Weak | Weak | Weak | Weak |
| 17 | Number of pillows | None | None | None | None |
| 18 | Length of primary branches (cm) | 14.10 | 12.21 | 14.70 | 13.57 |
| 19 | Spikelet shape | Broad Elliptic | Broad Elliptic | Broad Elliptic | Broad Elliptic |
| 20 | Glume anthocyanin coloration | Absent | Absent | Absent | Absent |
| 21 | Stigma color | White | White | White | White |
| 22 | Grain size | Large | Large | Large | Large |
| 23 | Grain shape | Broad Elliptic | Broad Elliptic | Broad Elliptic | Broad Elliptic |
| 24 | Grain color | White | White | White | White |
| 25 | Grain: presence of spotting/ridges | Absent | Absent | Absent | Absent |
| 26 | Grain: size of spots | Absent | Absent | Absent | Absent |
| 27 | Kernel (not polished) color | Light Yellow | Light Yellow | Light Yellow | Light Yellow |
| 28 | Kernel intensity of brown color of placental spot" | Dark | Medium | Dark | Dark |
| 29 | Type of endosperm | Non-waxy | Non-waxy | Non-waxy | Non-waxy |

| Sr. | Trait | DLG240 | Huntsman | Plateau | Sunup |
|---|---|---|---|---|---|
| 1 | Flag leaf attitude of blade | Semi erect | Semi erect | Semi erect | Semi erect |
| 2 | Flag leaf anthocyanin coloration | Absent | Absent | Absent | Absent |
| 3 | Flag leaf intensity of anthocyanin coloration | Absent | Absent | Absent | Absent |
| 4 | Flag leaf length (cm) | 25.7 | 29.4 | 28.9 | 33.3 |
| 5 | Flag leaf width (cm) | 2.08 | 2.15 | 2.05 | 1.88 |
| 6 | Number of internodes | 6 | 5 | 5 | 5 |
| 7 | Length of upper internode (cm) | 14.07 | 14.75 | 13.30 | 14.24 |
| 8 | Thickness of internodes (cm) | 0.54 | 0.53 | 0.51 | 0.52 |
| 9 | Time of panicle emergence (days) | 41 | 36 | 29 | 38 |
| 10 | Natural height (cm) | 104.58 | 101.09 | 98.13 | 102.41 |
| 11 | Angle of panicle branches | Very acute | Very acute | Moderately acute | Very acute |
| 12 | Panicle attitude | Semi erect | Semi erect | Moderately dropping | Semi erect |
| 13 | Panicle length, excluding peduncle (cm) | 20.96 | 23.03 | 30.85 | 21.82 |

TABLE 1-continued

| | | DLG240 Gilbert IA | | | |
|---|---|---|---|---|---|
| 14 | Panicle width (cm) | 5.06 | 7.6 | 7.68 | 3.44 |
| 15 | Panicle density | Dense | Dense | Medium | Dense |
| 16 | Degree of curvature of lateral branches | Weak | Medium | Strong | Weak |
| 17 | Number of pillows | None | None | None | None |
| 18 | Length of primary branches (cm) | 14.10 | 14.09 | 19.77 | 13.69 |
| 19 | Spikelet shape | Broad Elliptic | Broad Elliptic | Broad Elliptic | Broad Elliptic |
| 20 | Glume anthocyanin coloration | Absent | Absent | Absent | Absent |
| 21 | Stigma color | White | White | White | White |
| 22 | Grain size | Large | Large | Large | Large |
| 23 | Grain shape | Broad Elliptic | Broad Elliptic | Broad Elliptic | Broad Elliptic |
| 24 | Grain color | White | White | White | White |
| 25 | Grain: presence of spotting/ridges | Absent | Absent | Absent | Absent |
| 26 | Grain: size of spots | Absent | Absent | Absent | Absent |
| 27 | Kernel (not polished) color | Light Yellow | Light Yellow | Light Yellow | Light Yellow |
| 28 | Kernel intensity of brown color of placental spot" | Dark | Medium | Dark | Dark |
| 29 | Type of endosperm | Non-waxy | Non-waxy | Waxy | Non-waxy |

TABLE 2

| | | DLG240 Ventura IA | | | |
|---|---|---|---|---|---|
| Sr. | Trait | DLG240 | Dawn | Earlybird | Horizon |
| 1 | Flag leaf attitude of blade | Semi erect | Semi erect | Semi erect | Semi erect |
| 2 | Flag leaf anthocyanin coloration | Absent | Absent | Absent | Absent |
| 3 | Flag leaf intensity of anthocyanin coloration | Absent | Absent | Absent | Absent |
| 4 | Flag leaf length (cm) | 27.8 | 21.8 | 31.4 | 32.6 |
| 5 | Flag leaf width (cm) | 2.13 | 1.75 | 2.24 | 2.27 |
| 6 | Number of internodes | 5 | 4 | 5 | 5 |
| 7 | Length of upper internode (cm) | 15.7 | 16.3 | 16.2 | 15.7 |
| 8 | Thickness of internodes (cm) | 0.55 | 0.40 | 0.54 | 0.52 |
| 9 | Time of panicle emergence (days) | 41 | 28 | 35 | 33 |
| 10 | Natural height (cm) | 107.81 | 78.08 | 102.70 | 99.63 |
| 11 | Angle of panicle branches | Very acute | Very acute | Very acute | Very acute |
| 12 | Panicle attitude | Semi erect | Semi erect | Semi erect | Semi erect |
| 13 | Panicle length, excluding peduncle (cm) | 22.87 | 17.81 | 22.46 | 22.42 |
| 14 | Panicle width (cm) | 4.58 | 3.58 | 6.62 | 6 |
| 15 | Panicle density | Dense | Dense | Dense | Dense |
| 16 | Degree of curvature of lateral branches | Weak | Weak | Weak | Weak |
| 17 | Number of pillows | None | None | None | None |
| 18 | Length of primary branches (cm) | 13.71 | 11.53 | 13.58 | 13.31 |
| 19 | Spikelet shape | Broad Elliptic | Broad Elliptical | Broad Elliptical | Broad Elliptical |
| 20 | Glume anthocyanin coloration | Absent | Absent | Absent | Absent |
| 21 | Stigma color | White | White | White | White |
| 22 | Grain size | Large | Large | Large | Large |
| 23 | Grain shape | Broad Elliptic | Broad Elliptic | Broad Elliptic | Broad Elliptic |
| 24 | Grain color | White | White | White | White |
| 25 | Grain: presence of spotting/ridges | Absent | Absent | Absent | Absent |
| 26 | Grain: size of spots | Absent | Absent | Absent | Absent |
| 27 | Kernel (not polished) color | Light Yellow | Light Yellow | Light Yellow | Light Yellow |
| 28 | Kernel intensity of brown color of placental spot | Dark | Medium | Dark | Dark |
| 29 | Type of endosperm | Non-waxy | Non-waxy | Non-waxy | Non-waxy |
| Sr. | Trait | DLG240 | Huntsman | Plateau | Sunup |
| 1 | Flag leaf attitude of blade | Semi erect | Semi erect | Semi erect | Semi erect |
| 2 | Flag leaf anthocyanin coloration | Absent | Absent | Absent | Absent |

TABLE 2-continued

| | DLG240 Ventura IA | | | |
|---|---|---|---|---|
| 3 Flag leaf intensity of anthocyanin coloration | Absent | Absent | Absent | Absent |
| 4 Flag leaf length (cm) | 27.8 | 32.3 | 30.6 | 28.8 |
| 5 Flag leaf width (cm) | 2.13 | 2.16 | 1.92 | 1.98 |
| 6 Number of internodes | 5 | 5 | 5 | 5 |
| 7 Length of upper internode (cm) | 15.7 | 16.4 | 15 | 17.1 |
| 8 Thickness of internodes (cm) | 0.55 | 0.54 | 0.48 | 0.62 |
| 9 Time of panicle emergence (days) | 41 | 36 | 30 | 35 |
| 10 Natural height (cm) | 107.81 | 107.67 | 94.44 | 116.23 |
| 11 Angle of panicle branches | Very acute | Very acute | Moderately acute | Very acute |
| 12 Panicle attitude | Semi erect | Semi erect | Moderately dropping | Semi erect |
| 13 Panicle length, excluding peduncle (cm) | 22.87 | 22.79 | 32.25 | 23.01 |
| 14 Panicle width (cm) | 4.58 | 6.47 | 5.39 | 4.63 |
| 15 Panicle density | Dense | Dense | Medium | Dense |
| 16 Degree of curvature of lateral branches | Weak | Medium | Strong | Weak |
| 17 Number of pillows | None | None | None | None |
| 18 Length of primary branches (cm) | 13.71 | 13.71 | 19.07 | 13.74 |
| 19 Spikelet shape | Broad Elliptic | Broad Elliptical | Broad Elliptical | Broad Elliptical |
| 20 Glume anthocyanin coloration | Absent | Absent | Absent | Absent |
| 21 Stigma color | White | White | White | White |
| 22 Grain size | Large | Large | Large | Large |
| 23 Grain shape | Broad Elliptic | Broad Elliptic | Broad Elliptic | Broad Elliptic |
| 24 Grain color | White | White | White | White |
| 25 Grain: presence of spotting/ridges | Absent | Absent | Absent | Absent |
| 26 Grain: size of spots | Absent | Absent | Absent | Absent |
| 27 Kernel (not polished) color | Light Yellow | Light Yellow | Light Yellow | Light Yellow |
| 28 Kernel intensity of brown color of placental spot | Dark | Medium | Dark | Dark |
| 29 Type of endosperm | Non-waxy | Non-waxy | waxy | Non-waxy |

TABLE 3A

DLG240 small plot yield trials

| Year | Trial type | Location | Seeding rate | Plot size | Rows spacing (inch) |
|---|---|---|---|---|---|
| 2018 | Small plot | Akron CO | 20 lbs/ac | 125 sq. ft | 10 |
| 2018 | Small plot | Burlington CO | 20 lbs/ac | 125 sq. ft | 8 |
| 2018 | Small plot | Sidney NE | 20 lbs/ac | 125 sq. ft | 10 |
| 2019 | Small plot | Burlington CO | 20 lbs/ac | 125 sq. ft | 8 |
| 2019 | Small plot | Fleming CO | 20 lbs/ac | 125 sq. ft | 8 |
| 2019 | Small plot | Sidney NE | 20 lbs/ac | 125 sq. ft | 10 |
| 2020 | Small plot | Burlington CO | 20 lbs/ac | 125 sq. ft | 8 |
| 2020 | Small plot | Sidney NE | 20 lbs/ac | 125 sq. ft | 10 |

TABLE 3B

DLG240 foundation and certified plots

| Year | Plot type | Location | Seeding rate | Plot size | Row spacing (inch) |
|---|---|---|---|---|---|
| 2019 | Foundation | Rancagua Chile | 20 lbs/ac | 0.25 acres | 12 |
| 2019 | Foundation | Yuma CO | 17 lbs/ac | 10 acres | 10 |
| 2019 | Foundation | Sidney NE | 20 lbs/ac | 10 acres | 7.5 |
| 2020 | Certified | Matheson CO | 12 lbs/ac | 50 acres | 10 |
| 2020 | Foundation | Sidney NE | 20 lbs/ac | 4.6 acre | 7.5 |

TABLE 4A

DLG240 average grain yield (lbs/ac dry weight)

| | 2018 | | | 2019 | | | 2020 | |
|---|---|---|---|---|---|---|---|---|
| Variety | Akron | Burlington | Sidney | Fleming | Burlington | Sidney | Burlington | Sidney |
| DLG240 | 1464 | 4774 | 1715 | 2411 | 2021 | 1568 | 798 | 1558 |
| Dawn | 1150 | 1568 | 725 | na | 1011 | 1011 | 892 | 1958 |
| Earlybird | 1324 | 3032 | 1307 | na | 1742 | 1454 | 770 | 1674 |
| Horizon | 1394 | 3101 | 1721 | na | 1429 | 1394 | 676 | 1536 |
| Huntsman | 1499 | 3136 | 1512 | 2195 | 1673 | 1429 | 753 | 1518 |

TABLE 4A-continued

DLG240 average grain yield (lbs/ac dry weight)

| | 2018 | | | 2019 | | | 2020 | |
|---|---|---|---|---|---|---|---|---|
| Variety | Akron | Burlington | Sidney | Fleming | Burlington | Sidney | Burlington | Sidney |
| Plateau | 488 | 2335 | 1349 | na | 1708 | 1289 | 627 | 1288 |
| Sunup | 1568 | 3554 | 1495 | na | 1812 | 1812 | 732 | 1539 |
| Mean | 1270 | 3071 | 1403 | 2303 | 1628 | 1422 | 750 | 1582 |

TABLE 4B

DLG240 average grain yield (lbs/ac GPS adjusted mean)

| | 2018 | | | 2019 | | | 2020 | |
|---|---|---|---|---|---|---|---|---|
| Variety | Akron | Burlington | Sidney | Fleming | Burlington | Sidney | Burlington | Sidney |
| DLG240 | 1803 | 5499 | 1993 | 2481 | 1917 | 1620 | 474 | 1654 |
| Dawn | 728 | 1896 | 896 | na | 1021 | 958 | 606 | 1826 |
| Earlybird | 1523 | 3628 | 1415 | na | 1777 | 1394 | 655 | 1565 |
| Horizon | 1620 | 3642 | 1896 | na | 1453 | 1282 | 700 | 1582 |
| Huntsman | 1760 | 3729 | 1666 | 2265 | 1652 | 1432 | 519 | 1641 |
| Plateau | 1261 | 2600 | 1537 | na | 1746 | 1195 | 446 | 1425 |
| Sunup | 1798 | 4203 | 1655 | na | 1889 | 1715 | 575 | 1516 |
| Mean | 1499 | 3600 | 1580 | 2373 | 1636 | 1371 | 568 | 1601 |

TABLE 4C

DLG240 average as-is grain yield (lbs/ac)

| | 2019 | | | 2020 | |
|---|---|---|---|---|---|
| Variety | Gurley | Matheson | Yuma | Gurley | Matheson |
| DLG240 | 2400 | 2400 | 3350 | 2400 | 1265 |
| Huntsman | 2250 | 1750 | 2400 | 1400 | 1280 |

TABLE 5

DLG240 average test weight (pounds per bushel)

| | 2018 | | | 2019 | | | 2020 | |
|---|---|---|---|---|---|---|---|---|
| Variety | Akron | Burlington | Sidney | Fleming | Burlington | Sidney | Burlington | Sidney |
| DLG240 | 50 | 57 | 56 | 54 | 53 | 50 | 46 | 48 |
| Dawn | na | 51 | na | na | 54 | 48 | 53 | 49 |
| Earlybird | 52 | 55 | 51 | na | 55 | 47 | 46 | 49 |
| Horizon | 54 | 53 | 54 | na | 54 | 50 | 42 | 49 |
| Huntsman | 48 | 54 | 54 | 54 | 54 | 48 | 45 | 49 |
| Plateau | na | 53 | 49 | na | 51 | 46 | 41 | 47 |
| Sunup | 52 | 55 | 51 | na | 55 | 50 | 47 | 48 |
| Mean | 51 | 54 | 53 | 54 | 54 | 48 | 46 | 48 |

TABLE 6

DLG240 average heading date (days)

| | 2018 | | 2020 |
|---|---|---|---|
| Variety | Akron | Sidney | Sidney |
| DLG240 | 50 | 44 | 50 |
| Dawn | 42 | 45 | 47 |
| Earlybird | 45 | 45 | 48 |
| Huntsman | 48 | 45 | 47 |
| Horizon | 46 | 45 | 49 |
| Plateau | 43 | 43 | 44 |

TABLE 6-continued

DLG240 average heading date (days)

| | 2018 | | 2020 |
|---|---|---|---|
| Variety | Akron | Sidney | Sidney |
| Sunup | 47 | 46 | 50 |
| Mean | 46 | 45 | 48 |

TABLE 7

DLG240 average plant height (cm)

| | 2018 | | 2020 |
|---|---|---|---|
| Variety | Akron | Sidney | Sidney |
| DLG240 | 68.07 | 100.58 | 45.72 |
| Dawn | 51.82 | 61.98 | 43.18 |
| Earlybird | 62.99 | 107.70 | 43.18 |
| Huntsman | 68.07 | 102.62 | 43.18 |
| Horizon | 59.94 | 96.52 | 43.18 |
| Plateau | 77.22 | 105.66 | 45.72 |

TABLE 7-continued

DLG240 average plant height (cm)

| Variety | 2018 | | 2020 |
| --- | --- | --- | --- |
| | Akron | Sidney | Sidney |
| Sunup | 67.06 | 106.68 | 45.72 |
| Mean | 65.02 | 97.00 | 44.00 |

TABLE 8

DLG240 average 1000 grain weight (in grams)

| Line name | 2018 | | 2020 | |
| --- | --- | --- | --- | --- |
| | Burlington | Sidney | Burlington | Sidney |
| DLG240 | 7.5 | 7.8 | 5.9 | 6.0 |
| Dawn | 6.4 | 7.1 | 5.6 | 5.8 |
| Earlybird | 7.1 | 7.0 | 5.8 | 6.1 |
| Huntsman | 7.5 | 7.3 | 6.0 | 5.9 |
| Horizon | 7.9 | 7.0 | 6.2 | 6.2 |
| Plateau | 5.8 | 6.2 | 5.4 | 5.4 |
| Sunup | 7.8 | 7.1 | 6.6 | 6.4 |
| Mean | 7.1 | 7.1 | 5.9 | 5.9 |

DLG40

Tables 9 and 10 provide a detailed description of the morphological, physiological, and other characteristics of the DLG40 plants and seed that distinguish it from other varieties. In 2019, 30 plants of DLG40 and various commercial cultivars were space planted to collect the detailed data on each at Gilbert, IA (Table 9) and Ventura, IA (Table 10). The Gilbert Iowa trial was planted on Jun. 14, 2019 and harvested between Sep. 3-20, 2019. The Ventura, Iowa trial was planted on Jun. 20, 2019 and harvested between Sep. 3-20, 2019. These data were collected between June to September of 2019.

Tables 11A and 11B provide comparative yield data and other characteristics identifying the variety. Table 11A provides a summary of proso millet small plot yield trials grown during 2019-2020 in Colorado and Nebraska. Table 11B provides a summary of proso millet foundation plots grown from 2018-2020 in Colorado and Nebraska.

Tables 12-16 provide a trait data comparison between DLG40 and other known released check varieties. Table 12A provides a summary of average grain yield (lbs/ac) based on dry weight basis of variety DLG40 as compared to commercial proso millet cultivars grown at various Colorado and Nebraska locations from 2018 to 2020 in small yield plot trials planted as per Table 11A. Yield/acre was calculated using small plot trial data, adjusted for grain moisture. Table 12B provides a summary of average grain yield (lbs/ac) based on GPS adjusted mean (spatially variation adjustment) of variety DLG40 as compared to commercial proso millet cultivars grown at various Colorado and Nebraska locations from 2018-2020 in small yield plot trials planted as per Table 11A. Yield/acre was calculated using small plot trial data and adjusted for grain moisture. Table 12C provides a summary of average as-is grain yields (lbs/ac) of DLG40 and Huntsman from foundation plots grown at various locations in Colorado and Nebraska during 2019-2020 planted as per Table 11B. Table 13 provides a summary of average test weight (pounds per bushel) of DLG40 and commercial checks at various locations in Colorado and Nebraska in small yield plot trials grown from 2018 to 2020 planted as per Table 11A. Table 14 provides data for average heading date (days) of DLG40 and commercial checks (Dawn, Earlybird, Huntsman, Horizon, Plateau, Sunup) at Akron, CO and Sidney, NE in 2018 and 2020 small plot trials planted as per Table 11A. Table 15 provides data for average plant height (cm) of DLG40 and commercial checks (Dawn, Earlybird, Huntsman, Horizon, Plateau, Sunup) at Akron, CO and Sidney, NE locations in 2018 and 2020 small plot trials planted as per Table 11A. Table 16 provides the average 1000 grain weight (in grams) of DLG40 and commercial checks (Dawn, Earlybird, Huntsman, Horizon, Plateau, Sunup) in 2018 yield plot trials planted as per Table 11A.

TABLE 9

DLG40 Gilbert IA

| Sr. | Trait | DLG40 | Dawn | Earlybird | Horizon |
| --- | --- | --- | --- | --- | --- |
| 1 | Flag leaf attitude of blade | Semi erect | Semi erect | Semi erect | Semi erect |
| 2 | Flag leaf anthocyanin coloration | Absent | Absent | Absent | Absent |
| 3 | Flag leaf intensity of anthocyanin coloration | Absent | Absent | Absent | Absent |
| 4 | Flag leaf length (cm) | 25.8 | 23.4 | 27.9 | 27.8 |
| 5 | Flag leaf width (cm) | 2.04 | 1.78 | 1.83 | 2.86 |
| 6 | Number of internodes | 5 | 4 | 5 | 5 |
| 7 | Length of upper internode (cm) | 14.04 | 13.45 | 15.64 | 14.15 |
| 8 | Thickness of internodes (cm) | 0.57 | 0.45 | 0.67 | 0.69 |
| 9 | Time of panicle emergence (days) | 44 | 26 | 37 | 37 |
| 10 | Natural height (cm) | 97.76 | 78.8 | 106.32 | 99.03 |
| 11 | Angle of panicle branches | Very acute | Very acute | Very acute | Very acute |
| 12 | Panicle attitude | Semi erect | Semi erect | Semi erect | Semi erect |
| 13 | Panicle length, excluding peduncle (cm) | 20.94 | 19.38 | 22.1 | 21.35 |
| 14 | Panicle width (cm) | 4.81 | 4.82 | 5.45 | 4.49 |
| 15 | Panicle density | Dense | Dense | Dense | Dense |
| 16 | Degree of curvature of lateral branches | Weak | Weak | Weak | Weak |
| 17 | Number of pillows | None | None | None | None |
| 18 | Length of primary branches (cm) | 12.27 | 12.21 | 14.70 | 13.57 |
| 19 | Spikelet shape | Broad Elliptic | Broad Elliptic | Broad Elliptic | Broad Elliptic |
| 20 | Glume anthocyanin coloration | Absent | Absent | Absent | Absent |
| 21 | Stigma color | White | White | White | White |
| 22 | Grain size | Large | Large | Large | Large |
| 23 | Grain shape | Broad Elliptic | Broad Elliptic | Broad Elliptic | Broad Elliptic |

TABLE 9-continued

DLG40 Gilbert IA

| Sr. | Trait | | | | |
|---|---|---|---|---|---|
| 24 | Grain color | White | White | White | White |
| 25 | Grain: presence of spotting/ridges | Absent | Absent | Absent | Absent |
| 26 | Grain: size of spots | Absent | Absent | Absent | Absent |
| 27 | Kernel (not polished) color | Light Yellow | Light Yellow | Light Yellow | Light Yellow |
| 28 | Kernel intensity of brown color of placental spot | Dark | Medium | Dark | Dark |
| 29 | Type of endosperm | Non-waxy | Non-waxy | Non-waxy | Non-waxy |

| Sr. | Trait | DLG40 | Huntsman | Plateau | Sunup |
|---|---|---|---|---|---|
| 1 | Flag leaf attitude of blade | Semi erect | Semi erect | Semi erect | Semi erect |
| 2 | Flag leaf anthocyanin coloration | Absent | Absent | Absent | Absent |
| 3 | Flag leaf intensity of anthocyanin coloration | Absent | Absent | Absent | Absent |
| 4 | Flag leaf length (cm) | 25.8 | 29.4 | 28.9 | 33.3 |
| 5 | Flag leaf width (cm) | 2.04 | 2.15 | 2.05 | 1.88 |
| 6 | Number of internodes | 5 | 5 | 5 | 5 |
| 7 | Length of upper internode (cm) | 14.04 | 14.75 | 13.30 | 14.24 |
| 8 | Thickness of internodes (cm) | 0.57 | 0.53 | 0.51 | 0.52 |
| 9 | Time of panicle emergence (days) | 44 | 36 | 29 | 38 |
| 10 | Natural height (cm) | 97.76 | 101.09 | 98.13 | 102.41 |
| 11 | Angle of panicle branches | Very acute | Very acute | Moderately acute | Very acute |
| 12 | Panicle attitude | Semi erect | Semi erect | Moderately dropping | Semi erect |
| 13 | Panicle length, excluding peduncle (cm) | 20.94 | 23.03 | 30.85 | 21.82 |
| 14 | Panicle width (cm) | 4.81 | 7.6 | 7.68 | 3.44 |
| 15 | Panicle density | Dense | Dense | Medium | Dense |
| 16 | Degree of curvature of lateral branches | Weak | Medium | Strong | Weak |
| 17 | Number of pillows | None | None | None | None |
| 18 | Length of primary branches (cm) | 12.27 | 14.09 | 19.77 | 13.69 |
| 19 | Spikelet shape | Broad Elliptic | Broad Elliptic | Broad Elliptic | Broad Elliptic |
| 20 | Glume anthocyanin coloration | Absent | Absent | Absent | Absent |
| 21 | Stigma color | White | White | White | White |
| 22 | Grain size | Large | Large | Large | Large |
| 23 | Grain shape | Broad Elliptic | Broad Elliptic | Broad Elliptic | Broad Elliptic |
| 24 | Grain color | White | White | White | White |
| 25 | Grain: presence of spotting/ridges | Absent | Absent | Absent | Absent |
| 26 | Grain: size of spots | Absent | Absent | Absent | Absent |
| 27 | Kernel (not polished) color | Light Yellow | Light Yellow | Light Yellow | Light Yellow |
| 28 | Kernel intensity of brown color of placental spot | Dark | Medium | Dark | Dark |
| 29 | Type of endosperm | Non-waxy | Non-waxy | Waxy | Non-waxy |

TABLE 10

DLG40 Ventura IA

| Sr. | Trait | DLG40 | Dawn | Earlybird | Horizon |
|---|---|---|---|---|---|
| 1 | Flag leaf attitude of blade | Semi erect | Semi erect | Semi erect | Semi erect |
| 2 | Flag leaf anthocyanin coloration | Absent | Absent | Absent | Absent |
| 3 | Flag leaf intensity of anthocyanin coloration | Absent | Absent | Absent | Absent |
| 4 | Flag leaf length (cm) | 26.77 | 21.8 | 31.4 | 32.6 |
| 5 | Flag leaf width (cm) | 1.81 | 1.75 | 2.24 | 2.27 |
| 6 | Number of internodes | 5 | 4 | 5 | 5 |
| 7 | Length of upper internode (cm) | 13.96 | 16.3 | 16.2 | 15.7 |
| 8 | Thickness of internodes (cm) | 0.57 | 0.40 | 0.54 | 0.52 |
| 9 | Time of panicle emergence (days) | 37 | 28 | 35 | 33 |
| 10 | Natural height (cm) | 99.58 | 78.08 | 102.70 | 99.63 |
| 11 | Angle of panicle branches | Very acute | Very acute | Very acute | Very acute |
| 12 | Panicle attitude | Semi erect | Semi erect | Semi erect | Semi erect |
| 13 | Panicle length, excluding peduncle (cm) | 20.84 | 17.81 | 22.46 | 22.42 |
| 14 | Panicle width (cm) | 6.66 | 3.58 | 6.62 | 6 |
| 15 | Panicle density | Dense | Dense | Dense | Dense |
| 16 | Degree of curvature of lateral branches | Weak | Weak | Weak | Weak |

TABLE 10-continued

DLG40 Ventura IA

| Sr. | Trait | | | | |
|---|---|---|---|---|---|
| 17 | Number of pillows | None | None | None | None |
| 18 | Length of primary branches (cm) | 12.45 | 11.53 | 13.58 | 13.31 |
| 19 | Spikelet shape | Broad Elliptic | Broad Elliptical | Broad Elliptical | Broad Elliptical |
| 20 | Glume anthocyanin coloration | Absent | Absent | Absent | Absent |
| 21 | Stigma color | White | White | White | White |
| 22 | Grain size | Large | Large | Large | Large |
| 23 | Grain shape | Broad Elliptic | Broad Elliptic | Broad Elliptic | Broad Elliptic |
| 24 | Grain color | White | White | White | White |
| 25 | Grain: presence of spotting/ridges | Absent | Absent | Absent | Absent |
| 26 | Grain: size of spots | Absent | Absent | Absent | Absent |
| 27 | Kernel (not polished) color | Light Yellow | Light Yellow | Light Yellow | Light Yellow |
| 28 | Kernel intensity of brown color of placental spot | Dark | Medium | Dark | Dark |
| 29 | Type of endosperm | Non-waxy | Non-waxy | Non-waxy | Non-waxy |

| Sr. | Trait | DLG40 | Huntsman | Plateau | Sunup |
|---|---|---|---|---|---|
| 1 | Flag leaf attitude of blade | Semi erect | Semi erect | Semi erect | Semi erect |
| 2 | Flag leaf anthocyanin coloration | Absent | Absent | Absent | Absent |
| 3 | Flag leaf intensity of anthocyanin coloration | Absent | Absent | Absent | Absent |
| 4 | Flag leaf length (cm) | 26.77 | 32.3 | 30.6 | 28.8 |
| 5 | Flag leaf width (cm) | 1.81 | 2.16 | 1.92 | 1.98 |
| 6 | Number of internodes | 5 | 5 | 5 | 5 |
| 7 | Length of upper internode (cm) | 13.96 | 16.4 | 15 | 17.1 |
| 8 | Thickness of internodes (cm) | 0.57 | 0.54 | 0.48 | 0.62 |
| 9 | Time of panicle emergence (days) | 37 | 36 | 30 | 35 |
| 10 | Natural height (cm) | 99.58 | 107.67 | 94.44 | 116.23 |
| 11 | Angle of panicle branches | Very acute | Very acute | Moderately acute | Very acute |
| 12 | Panicle attitude | Semi erect | Semi erect | Moderately dropping | Semi erect |
| 13 | Panicle length, excluding peduncle (cm) | 20.84 | 22.79 | 32.25 | 23.01 |
| 14 | Panicle width (cm) | 6.66 | 6.47 | 5.39 | 4.63 |
| 15 | Panicle density | Dense | Dense | Medium | Dense |
| 16 | Degree of curvature of lateral branches | Weak | Medium | Strong | Weak |
| 17 | Number of pillows | None | None | None | None |
| 18 | Length of primary branches (cm) | 12.45 | 13.71 | 19.07 | 13.74 |
| 19 | Spikelet shape | Broad Elliptic | Broad Elliptical | Broad Elliptical | Broad Elliptical |
| 20 | Glume anthocyanin coloration | Absent | Absent | Absent | Absent |
| 21 | Stigma color | White | White | White | White |
| 22 | Grain size | Large | Large | Large | Large |
| 23 | Grain shape | Broad Elliptic | Broad Elliptic | Broad Elliptic | Broad Elliptic |
| 24 | Grain color | White | White | White | White |
| 25 | Grain: presence of spotting/ridges | Absent | Absent | Absent | Absent |
| 26 | Grain: size of spots | Absent | Absent | Absent | Absent |
| 27 | Kernel (not polished) color | Light Yellow | Light Yellow | Light Yellow | Light Yellow |
| 28 | Kernel intensity of brown color of placental spot | Dark | Medium | Dark | Dark |
| 29 | Type of endosperm | Non-waxy | Non-waxy | waxy | Non-waxy |

TABLE 11A

DLG40 small plot yield trials

| Year | Trial type | Location | Seeding rate | Plot size | Rows spacing (inch) |
|---|---|---|---|---|---|
| 2018 | Small plot | Akron CO | 20 lbs/ac | 125 sq. ft | 10 |
| 2018 | Small plot | Burlington CO | 20 lbs/ac | 125 sq. ft | 8 |
| 2018 | Small plot | Sidney NE | 20 lbs/ac | 125 sq. ft | 10 |
| 2019 | Small plot | Burlington CO | 20 lbs/ac | 125 sq. ft | 8 |
| 2019 | Small plot | Fleming CO | 20 lbs/ac | 125 sq. ft | 8 |
| 2019 | Small plot | Sidney NE | 20 lbs/ac | 125 sq. ft | 10 |
| 2020 | Small plot | Burlington CO | 20 lbs/ac | 125 sq. ft | 8 |
| 2020 | Small plot | Sidney NE | 20 lbs/ac | 125 sq. ft | 10 |

TABLE 11B

DLG40 foundation plots

| Year | Plot type | Location | Seeding rate | Plot size | Row spacing (inch) |
|---|---|---|---|---|---|
| 2019 | Foundation | Matheson CO | 12 lbs/ac | 10 acres | 10 |
| 2019 | Foundation | Rancagua Chile | 20 lbs/ac | 0.25 acre | 12 |
| 2020 | Foundation | Sidney NE | 20 lbs/ac | 4.6 acre | 7.5 |

TABLE 12A

DLG40 average grain yield (lbs/ac dry weight)

| Variety | 2018 | | | 2019 | | | 2020 | |
|---|---|---|---|---|---|---|---|---|
| | Akron | Burlington | Sidney | Fleming | Burlington | Sidney | Burlington | Sidney |
| DLG40 | 2021 | 3589 | 1547 | 2648 | 1951 | 1185 | 648 | 1526 |
| Dawn | 1150 | 1568 | 725 | na | 1011 | 1011 | 892 | 1958 |
| Earlybird | 1324 | 3032 | 1307 | na | 1742 | 1454 | 770 | 1674 |
| Horizon | 1394 | 3101 | 1721 | na | 1429 | 1394 | 676 | 1536 |
| Huntsman | 1499 | 3136 | 1512 | 2195 | 1673 | 1429 | 753 | 1518 |
| Plateau | 488 | 2335 | 1349 | na | 1708 | 1289 | 627 | 1288 |
| Sunup | 1568 | 3554 | 1495 | na | 1812 | 1812 | 732 | 1539 |
| Mean | 1349 | 2902 | 1379 | 2422 | 1618 | 1368 | 728 | 1577 |

TABLE 12B

DLG40 average grain yield (lbs/ac GPS adjusted mean)

| Variety | 2018 | | | 2019 | | | 2020 | |
|---|---|---|---|---|---|---|---|---|
| | Akron | Burlington | Sidney | Fleming | Burlington | Sidney | Burlington | Sidney |
| DLG40 | 2237 | 4251 | 1892 | 2736 | 1885 | 1234 | 448 | 1646 |
| Dawn | 728 | 1896 | 896 | na | 1021 | 958 | 606 | 1826 |
| Earlybird | 1523 | 3628 | 1415 | na | 1777 | 1394 | 655 | 1565 |
| Horizon | 1620 | 3642 | 1896 | na | 1453 | 1282 | 700 | 1582 |
| Huntsman | 1760 | 3729 | 1666 | 2265 | 1652 | 1432 | 519 | 1641 |
| Plateau | 1261 | 2600 | 1537 | na | 1746 | 1195 | 446 | 1425 |
| Sunup | 1798 | 4203 | 1655 | na | 1889 | 1715 | 575 | 1516 |
| Mean | 1561 | 3421 | 1565 | 2500 | 1631 | 1315 | 564 | 1600 |

TABLE 12C

DLG40 average as-is grain yield (lbs/ac)

| Variety | 2019 Chile | 2019 Matheson | 2020 Gurley |
|---|---|---|---|
| DLG40 | 2900 | 1700 | 2250 |
| Huntsman | na | 1750 | 1400 |

TABLE 13

DLG40 average test weight (pounds per bushel)

| Variety | 2018 | | | 2019 | | | 2020 | |
|---|---|---|---|---|---|---|---|---|
| | Akron | Burlington | Sidney | Fleming | Burlington | Sidney | Burlington | Sidney |
| DLG40 | 56 | 56 | 53 | 52 | 52 | 48 | 44 | 47 |
| Dawn | na | 51 | na | na | 54 | 48 | 53 | 49 |
| Earlybird | 52 | 55 | 51 | na | 55 | 47 | 46 | 49 |
| Horizon | 54 | 53 | 54 | na | 54 | 50 | 42 | 49 |
| Huntsman | 48 | 54 | 54 | 54 | 54 | 48 | 45 | 49 |
| Plateau | na | 53 | 49 | na | 51 | 46 | 41 | 47 |
| Sunup | 52 | 55 | 51 | na | 55 | 50 | 47 | 48 |
| Mean | 52 | 54 | 52 | 53 | 54 | 48 | 45 | 48 |

TABLE 14

DLG40 average heading date (days)

| Variety | 2018 | | 2020 |
|---|---|---|---|
| | Akron | Sidney | Sidney |
| DLG40 | 46 | 45 | 48 |
| Dawn | 42 | 45 | 47 |
| Earlybird | 45 | 45 | 48 |
| Huntsman | 48 | 45 | 47 |
| Horizon | 46 | 45 | 49 |
| Plateau | 43 | 43 | 44 |

TABLE 14-continued

DLG40 average heading date (days)

| Variety | 2018 | | 2020 |
|---|---|---|---|
| | Akron | Sidney | Sidney |
| Sunup | 47 | 46 | 50 |
| Mean | 45 | 45 | 48 |

TABLE 15

DLG40 average plant height (cm)

| Variety | 2018 | | 2020 |
|---|---|---|---|
| | Akron | Sidney | Sidney |
| DLG40 | 67.05 | 88.39 | 45.72 |
| Dawn | 51.82 | 61.98 | 43.18 |
| Earlybird | 62.99 | 107.70 | 43.18 |
| Huntsman | 68.07 | 102.62 | 43.18 |
| Horizon | 59.94 | 96.52 | 43.18 |
| Plateau | 77.22 | 105.66 | 45.72 |
| Sunup | 67.06 | 106.68 | 45.72 |
| Mean | 64.88 | 65.65 | 44.27 |

TABLE 16

DLG40 average 1000 grain weight (in grams)

| Line name | 2018 | | 2020 | |
|---|---|---|---|---|
| | Burlington | Sidney | Burlington | Sidney |
| DLG40 | 7.3 | 7.2 | 6.1 | 6.1 |
| Dawn | 6.4 | 7.1 | 5.6 | 5.8 |
| Earlybird | 7.1 | 7.0 | 5.8 | 6.1 |
| Huntsman | 7.5 | 7.3 | 6.0 | 5.9 |
| Horizon | 7.9 | 7.0 | 6.2 | 6.2 |
| Plateau | 5.8 | 6.2 | 5.4 | 5.4 |
| Sunup | 7.8 | 7.1 | 6.6 | 6.4 |
| Mean | 7.1 | 7.0 | 5.9 | 5.9 |

DLG148

Tables 17 and 18 provide a detailed description of the morphological, physiological, and other characteristics of the DLG148 plants and seed that distinguish it from other varieties. In 2019, 30 plants of DLG148 and various commercial cultivars were space planted to collect the detailed data on each at Gilbert, IA (Table 17) and Ventura, IA (Table 18). The Gilbert Iowa trial was planted on Jun. 14, 2019 and harvested between Sep. 3-20, 2019. The Ventura, Iowa trial was planted on Jun. 20, 2019 and harvested between Sep. 3-20, 2019. These data were collected between June to September of 2019.

Tables 19A and 19B provide comparative yield data and other characteristics identifying the variety. Table 19A provides a summary of proso millet small plot yield trials grown during 2018-2020 in Colorado and Nebraska. Table 19B provides a summary of a proso millet foundation plot grown in 2019 in Colorado.

Tables 20-24 provide a trait data comparison between DLG148 and other known released check varieties. Table 20A provides a summary of average grain yield (lbs/ac) based on dry weight basis of variety DLG148 as compared to commercial proso millet cultivars grown at various Colorado and Nebraska locations from 2018 to 2020 in small yield plot trials planted as per Table 19A. Yield/acre was calculated using small plot trial data, adjusted for grain moisture. Table 20B provides a summary of average grain yield (lbs/ac) based on GPS adjusted mean (spatially variation adjustment) of variety DLG148 as compared to commercial proso millet cultivars grown at various Colorado and Nebraska locations from 2018-2020 in small yield plot trials planted as per Table 19A. Yield/acre was calculated using small plot trial data and adjusted for grain moisture. Table 20C provides a summary of average as-is grain yields (lbs/ac) of DLG148 and Huntsman from foundation plots grown in Colorado during 2019 planted as per Table 19B. Table 21 provides a summary of average test weight (pounds per bushel) of DLG148 and commercial checks at various locations in Colorado and Nebraska in small yield plot trials grown from 2018 to 2020 planted as per Table 19A. Table 22 provides data for average heading date (days) of DLG148 and commercial checks (Dawn, Earlybird, Huntsman, Horizon, Plateau, Sunup) at Akron, CO and Sidney, NE in 2018 and 2020 small plot trials planted as per Table 19A. Table 23 provides data for average plant height (cm) of DLG148 and commercial checks (Dawn, Earlybird, Huntsman, Horizon, Plateau, Sunup) at Akron, CO and Sidney, NE locations in 2018 and 2020 small plot trials planted as per Table 19A. Table 24 provides the average 1000 grain weight (in grams) of DLG148 and commercial checks (Dawn, Earlybird, Huntsman, Horizon, Plateau, Sunup) in 2018 yield plot trials planted as per Table 19A.

TABLE 17

| | DLG148 Gilbert IA | | | | |
|---|---|---|---|---|---|
| Sr. | Trait | DLG148 | Dawn | Earlybird | Horizon |
| 1 | Flag leaf attitude of blade | Semi erect | Semi erect | Semi erect | Semi erect |
| 2 | Flag leaf anthocyanin coloration | Absent | Absent | Absent | Absent |
| 3 | Flag leaf intensity of anthocyanin coloration | Absent | Absent | Absent | Absent |
| 4 | Flag leaf length (cm) | 23.7 | 23.4 | 27.9 | 27.8 |
| 5 | Flag leaf width (cm) | 2.33 | 1.78 | 1.83 | 2.86 |
| 6 | Number of internodes | 5 | 4 | 5 | 5 |
| 7 | Length of upper internode (cm) | 20.24 | 13.45 | 15.64 | 14.15 |
| 8 | Thickness of internodes (cm) | 0.54 | 0.45 | 0.67 | 0.69 |
| 9 | Time of panicle emergence (days) | 41 | 26 | 37 | 37 |
| 10 | Natural height (cm) | 93.73 | 78.8 | 106.32 | 99.03 |
| 11 | Angle of panicle branches | Very acute | Very acute | Very acute | Very acute |
| 12 | Panicle attitude | Semi erect | Semi erect | Semi erect | Semi erect |
| 13 | Panicle length, excluding peduncle (cm) | 20.43 | 19.38 | 22.1 | 21.35 |

TABLE 17-continued

| | | DLG148 Gilbert IA | | | |
|---|---|---|---|---|---|
| 14 | Panicle width (cm) | 5.44 | 4.82 | 5.45 | 4.49 |
| 15 | Panicle density | Dense | Dense | Dense | Dense |
| 16 | Degree of curvature of lateral branches | Weak | Weak | Weak | Weak |
| 17 | Number of pillows | None | None | None | None |
| 18 | Length of primary branches (cm) | 13.31 | 12.21 | 14.70 | 13.57 |
| 19 | Spikelet shape | Broad Elliptic | Broad Elliptic | Broad Elliptic | Broad Elliptic |
| 20 | Glume anthocyanin coloration | Absent | Absent | Absent | Absent |
| 21 | Stigma color | White | White | White | White |
| 22 | Grain size of spots | Large | Large | Large | Large |
| 23 | Grain shape | Broad Elliptic | Broad Elliptic | Broad Elliptic | Broad Elliptic |
| 24 | Grain color | White | White | White | White |
| 25 | Grain: presence of spotting/ridges | Absent | Absent | Absent | Absent |
| 26 | Grain: size of spots | Absent | Absent | Absent | Absent |
| 27 | Kernel (not polished) color | Light Yellow | Light Yellow | Light Yellow | Light Yellow |
| 28 | Kernel intensity of brown color of placental spot | Medium | Medium | Dark | Dark |
| 29 | Kernel: type of endosperm | Non-waxy | Non-waxy | Non-waxy | Non-waxy |
| Sr. | Trait | DLG148 | Huntsman | Plateau | Sunup |
| 1 | Flag leaf attitude of blade | Semi erect | Semi erect | Semi erect | Semi erect |
| 2 | Flag leaf anthocyanin coloration | Absent | Absent | Absent | Absent |
| 3 | Flag leaf intensity of anthocyanin coloration | Absent | Absent | Absent | Absent |
| 4 | Flag leaf length (cm) | 23.7 | 29.4 | 28.9 | 33.3 |
| 5 | Flag leaf width (cm) | 2.33 | 2.15 | 2.05 | 1.88 |
| 6 | Number of internodes | 5 | 5 | 5 | 5 |
| 7 | Length of upper internode (cm) | 20.24 | 14.75 | 13.30 | 14.24 |
| 8 | Thickness of internodes (cm) | 0.54 | 0.53 | 0.51 | 0.52 |
| 9 | Time of panicle emergence (days) | 41 | 36 | 29 | 38 |
| 10 | Natural height (cm) | 93.73 | 101.09 | 98.13 | 102.41 |
| 11 | Angle of panicle branches | Very acute | Very acute | Moderately acute | Very acute |
| 12 | Panicle attitude | Semi erect | Semi erect | Moderately dropping | Semi erect |
| 13 | Panicle length, excluding peduncle (cm) | 20.43 | 23.03 | 30.85 | 21.82 |
| 14 | Panicle width (cm) | 5.44 | 7.6 | 7.68 | 3.44 |
| 15 | Panicle density | Dense | Dense | Medium | Dense |
| 16 | Degree of curvature of lateral branches | Weak | Medium | Strong | Weak |
| 17 | Number of pillows | None | None | None | None |
| 18 | Length of primary branches (cm) | 13.31 | 14.09 | 19.77 | 13.69 |
| 19 | Spikelet shape | Broad Elliptic | Broad Elliptic | Broad Elliptic | Broad Elliptic |
| 20 | Glume anthocyanin coloration | Absent | Absent | Absent | Absent |
| 21 | Stigma color | White | White | White | White |
| 22 | Grain size of spots | Large | Large | Large | Large |
| 23 | Grain shape | Broad Elliptic | Broad Elliptic | Broad Elliptic | Broad Elliptic |
| 24 | Grain color | White | White | White | White |
| 25 | Grain: presence of spotting/ridges | Absent | Absent | Absent | Absent |
| 26 | Grain: size of spots | Absent | Absent | Absent | Absent |
| 27 | Kernel (not polished) color | Light Yellow | Light Yellow | Light Yellow | Light Yellow |
| 28 | Kernel intensity of brown color of placental spot | Medium | Medium | Dark | Dark |
| 29 | Kernel: type of endosperm | Non-waxy | Non-waxy | Waxy | Non-waxy |

TABLE 18

| | | DLG148 Ventura IA | | | |
|---|---|---|---|---|---|
| Sr. | Trait | DLG148 | Dawn | Earlybird | Horizon |
| 1 | Flag leaf attitude of blade | Semi erect | Semi erect | Semi erect | Semi erect |
| 2 | Flag leaf anthocyanin coloration | Absent | Absent | Absent | Absent |
| 3 | Flag leaf intensity of anthocyanin coloration | Absent | Absent | Absent | Absent |
| 4 | Flag leaf length (cm) | 30.54 | 21.8 | 31.4 | 32.6 |
| 5 | Flag leaf width (cm) | 2.05 | 1.75 | 2.24 | 2.27 |
| 6 | Number of internodes | 5 | 4 | 5 | 5 |

TABLE 18-continued

| | DLG148 Ventura IA | | | |
|---|---|---|---|---|
| 7 Length of upper internode (cm) | 14.06 | 16.3 | 16.2 | 15.7 |
| 8 Thickness of internodes (cm) | 0.54 | 0.40 | 0.54 | 0.52 |
| 9 Time of panicle emergence (days) | 35 | 28 | 35 | 33 |
| 10 Natural height (cm) | 108.59 | 78.08 | 102.70 | 99.63 |
| 11 Angle of panicle branches | Very acute | Very acute | Very acute | Very acute |
| 12 Panicle attitude | Semi erect | Semi erect | Semi erect | Semi erect |
| 13 Panicle length, excluding peduncle (cm) | 22.79 | 17.81 | 22.46 | 22.42 |
| 14 Panicle width (cm) | 5.46 | 3.58 | 6.62 | 6 |
| 15 Panicle density | Dense | Dense | Dense | Dense |
| 16 Degree of curvature of lateral branches | Weak | Weak | Weak | Weak |
| 17 Number of pillows | None | None | None | None |
| 18 Length of primary branches (cm) | 12.38 | 11.53 | 13.58 | 13.31 |
| 19 Spikelet shape | Broad Elliptic | Broad Elliptical | Broad Elliptical | Broad Elliptical |
| 20 Glume anthocyanin coloration | Absent | Absent | Absent | Absent |
| 21 Stigma color | White | White | White | White |
| 22 Grain size of spots | Large | Large | Large | Large |
| 23 Grain shape | Broad Elliptic | Broad Elliptic | Broad Elliptic | Broad Elliptic |
| 24 Grain color | White | White | White | White |
| 25 Grain: presence of spotting/ridges | Absent | Absent | Absent | Absent |
| 26 Grain: size of spots | Absent | Absent | Absent | Absent |
| 27 Kernel (not polished) color | Light Yellow | Light Yellow | Light Yellow | Light Yellow |
| 28 Kernel intensity of brown color of placental spot | Medium | Medium | Dark | Dark |
| 29 Kernel: type of endosperm | Non-waxy | Non-waxy | Non-waxy | Non-waxy |

| Sr. | Trait | DLG148 | Huntsman | Plateau | Sunup |
|---|---|---|---|---|---|
| 1 | Flag leaf attitude of blade | Semi erect | Semi erect | Semi erect | Semi erect |
| 2 | Flag leaf anthocyanin coloration | Absent | Absent | Absent | Absent |
| 3 | Flag leaf intensity of anthocyanin coloration | Absent | Absent | Absent | Absent |
| 4 | Flag leaf length (cm) | 30.54 | 32.3 | 30.6 | 28.8 |
| 5 | Flag leaf width (cm) | 2.05 | 2.16 | 1.92 | 1.98 |
| 6 | Number of internodes | 5 | 5 | 5 | 5 |
| 7 | Length of upper internode (cm) | 14.06 | 16.4 | 15 | 17.1 |
| 8 | Thickness of internodes (cm) | 0.54 | 0.54 | 0.48 | 0.62 |
| 9 | Time of panicle emergence (days) | 35 | 36 | 30 | 35 |
| 10 | Natural height (cm) | 108.59 | 107.67 | 94.44 | 116.23 |
| 11 | Angle of panicle branches | Very acute | Very acute | Moderately acute | Very acute |
| 12 | Panicle attitude | Semi erect | Semi erect | Moderately dropping | Semi erect |
| 13 | Panicle length, excluding peduncle (cm) | 22.79 | 22.79 | 32.25 | 23.01 |
| 14 | Panicle width (cm) | 5.46 | 6.47 | 5.39 | 4.63 |
| 15 | Panicle density | Dense | Dense | Medium | Dense |
| 16 | Degree of curvature of lateral branches | Weak | Medium | Strong | Weak |
| 17 | Number of pillows | None | None | None | None |
| 18 | Length of primary branches (cm) | 12.38 | 13.71 | 19.07 | 13.74 |
| 19 | Spikelet shape | Broad Elliptic | Broad Elliptical | Broad Elliptical | Broad Elliptical |
| 20 | Glume anthocyanin coloration | Absent | Absent | Absent | Absent |
| 21 | Stigma color | White | White | White | White |
| 22 | Grain size of spots | Large | Large | Large | Large |
| 23 | Grain shape | Broad Elliptic | Broad Elliptic | Broad Elliptic | Broad Elliptic |
| 24 | Grain color | White | White | White | White |
| 25 | Grain: presence of spotting/ridges | Absent | Absent | Absent | Absent |
| 26 | Grain: size of spots | Absent | Absent | Absent | Absent |
| 27 | Kernel (not polished) color | Light Yellow | Light Yellow | Light Yellow | Light Yellow |

TABLE 18-continued

| DLG148 Ventura IA | | | | |
|---|---|---|---|---|
| 28 Kernel intensity of brown color of placental spot | Medium | Medium | Dark | Dark |
| 29 Kernel: type of endosperm | Non-waxy | Non-waxy | waxy | Non-waxy |

TABLE 19A

DLG148 small plot yield trials

| Year | Trial type | Location | Seed rate | Plot size | Rows spacing (inch) |
|---|---|---|---|---|---|
| 2018 | Small plot | Akron CO | 20 lbs/ac | 125 sq. ft | 10 |
| 2018 | Small plot | Burlington CO | 20 lbs/ac | 125 sq. ft | 8 |
| 2018 | Small plot | Sidney NE | 20 lbs/ac | 125 sq. ft | 10 |
| 2019 | Small plot | Burlington CO | 20 lbs/ac | 125 sq. ft | 8 |
| 2019 | Small plot | Fleming CO | 20 lbs/ac | 125 sq. ft | 8 |
| 2019 | Small plot | Sidney NE | 20 lbs/ac | 125 sq. ft | 10 |
| 2020 | Small plot | Burlington CO | 20 lbs/ac | 125 sq. ft | 8 |
| 2020 | Small plot | Sidney NE | 20 lbs/ac | 125 sq. ft | 10 |

TABLE 19B

DLG148 foundation plot

| Year | Plot type | Location | Seed rate | Plot size | Row spacing (inch) |
|---|---|---|---|---|---|
| 2019 | Foundation | Paine Chile | 20 lbs/ac | 0.25 acre | 12 |
| 2019 | Foundation | Matheson CO | 12 lbs/ac | 10 acres | 10 |

TABLE 20A

DLG148 average grain yield (lbs/ac dry weight)

| | 2018 | | | 2019 | | | 2020 | |
|---|---|---|---|---|---|---|---|---|
| Variety | Akron | Burlington | Sidney | Fleming | Burlington | Sidney | Burlington | Sidney |
| DLG148 | 1812 | 3589 | 1561 | 2750 | 2143 | 1115 | 718 | 1592 |
| Dawn | 1150 | 1568 | 725 | na | 1011 | 1011 | 892 | 1958 |
| Earlybird | 1324 | 3032 | 1307 | na | 1742 | 1454 | 770 | 1674 |
| Horizon | 1394 | 3101 | 1721 | na | 1429 | 1394 | 676 | 1536 |
| Huntsman | 1499 | 3136 | 1512 | 2195 | 1673 | 1429 | 753 | 1518 |
| Plateau | 488 | 2335 | 1349 | na | 1708 | 1289 | 627 | 1288 |
| Sunup | 1568 | 3554 | 1495 | na | 1812 | 1812 | 732 | 1539 |
| Mean | 1319 | 2902 | 1381 | 2472 | 1645 | 1358 | 738 | 1586 |

TABLE 20B

DLG148 average grain yield (lbs/ac GPS adjusted mean)

| | 2018 | | | 2019 | | | 2020 | |
|---|---|---|---|---|---|---|---|---|
| Variety | Akron | Burlington | Sidney | Fleming | Burlington | Sidney | Burlington | Sidney |
| DLG148 | 2136 | 4255 | 1669 | 2729 | 1868 | 1174 | 556 | 1618 |
| Dawn | 728 | 1896 | 896 | na | 1021 | 958 | 606 | 1826 |
| Earlybird | 1523 | 3628 | 1415 | na | 1777 | 1394 | 655 | 1565 |
| Horizon | 1620 | 3642 | 1896 | na | 1453 | 1282 | 700 | 1582 |
| Huntsman | 1760 | 3729 | 1666 | 2265 | 1652 | 1432 | 519 | 1641 |
| Plateau | 1261 | 2600 | 1537 | na | 1746 | 1195 | 446 | 1425 |
| Sunup | 1798 | 4203 | 1655 | na | 1889 | 1715 | 575 | 1516 |
| Mean | 1547 | 3422 | 1533 | 2497 | 1629 | 1307 | 580 | 1596 |

TABLE 20C

DLG148 average as-is grain yield (lbs/ac)

| Variety | 2019 Paine Chile | 2019 Matheson |
|---|---|---|
| DLG148 | 2680 | 1600 |
| Huntsman | na | 1750 |

TABLE 21

DLG148 average test weight (pounds per bushel)

| | 2018 | | | 2019 | | 2020 | |
|---|---|---|---|---|---|---|---|
| Variety | Akron | Burlington | Sidney | Fleming | Burlington | Sidney | Burlington | Sidney |
| DLG148 | 54 | 54 | 54 | 53 | 53 | 48 | 44 | 48 |
| Dawn | na | 51 | na | na | 54 | 48 | 53 | 49 |
| Earlybird | 52 | 55 | 51 | na | 55 | 47 | 46 | 49 |
| Horizon | 54 | 53 | 54 | na | 54 | 50 | 42 | 49 |
| Huntsman | 48 | 54 | 54 | 54 | 54 | 48 | 45 | 49 |
| Plateau | na | 53 | 49 | na | 51 | 46 | 41 | 47 |
| Sunup | 52 | 55 | 51 | na | 55 | 50 | 47 | 48 |
| Mean | 52 | 54 | 52 | 54 | 54 | 48 | 45 | 48 |

TABLE 22

DLG148 average heading date (days)

| | 2018 | | 2020 |
|---|---|---|---|
| Variety | Akron | Sidney | Sidney |
| DLG148 | 45 | 46 | 48 |
| Dawn | 42 | 45 | 47 |
| Earlybird | 45 | 45 | 48 |
| Huntsman | 48 | 45 | 47 |
| Horizon | 46 | 45 | 49 |
| Plateau | 43 | 43 | 44 |
| Sunup | 47 | 46 | 50 |
| Mean | 45 | 45 | 48 |

TABLE 23

DLG148 average plant height (cm)

| | 2018 | | 2020 |
|---|---|---|---|
| Variety | Akron | Sidney | Sidney |
| DLG148 | 60.75 | 100.75 | 43.18 |
| Dawn | 51.82 | 61.98 | 43.18 |
| Earlybird | 62.99 | 107.70 | 43.18 |
| Huntsman | 68.07 | 102.62 | 43.18 |
| Horizon | 59.94 | 96.52 | 43.18 |
| Plateau | 77.22 | 105.66 | 45.72 |
| Sunup | 67.06 | 106.68 | 45.72 |
| Mean | 63.98 | 97.42 | 43.91 |

TABLE 24

DLG148 average 1000 grain weight (in grams)

| | 2018 | | 2020 | |
|---|---|---|---|---|
| Line name | Burlington | Sidney | Burlington | Sidney |
| DLG148 | 7.7 | 7.9 | 5.8 | 6.4 |
| Dawn | 6.4 | 7.1 | 5.6 | 5.8 |
| Earlybird | 7.1 | 7.0 | 5.8 | 6.1 |
| Huntsman | 7.5 | 7.3 | 6.0 | 5.9 |
| Horizon | 7.9 | 7.0 | 6.2 | 6.2 |
| Plateau | 5.8 | 6.2 | 5.4 | 5.4 |
| Sunup | 7.8 | 7.1 | 6.6 | 6.4 |
| Mean | 7.2 | 7.1 | 5.9 | 6.0 |

DLG149

Tables 25 and 26 provide a detailed description of the morphological, physiological, and other characteristics of the DLG149 plants and seed that distinguish it from other varieties. In 2019, 30 plants of DLG149 and various commercial cultivars were space planted to collect the detailed data on each at Gilbert, IA (Table 25) and Ventura, IA (Table 26). The Gilbert Iowa trial was planted on Jun. 14, 2019 and harvested between Sep. 3-20, 2019. The Ventura, Iowa trial was planted on Jun. 20, 2019 and harvested between Sep. 3-20, 2019. These data were collected between June to September of 2019.

Tables 27A and 27B provide comparative yield data and other characteristics identifying the variety. Table 27A provides a summary of proso millet small plot yield trials grown during 2018-2020 in Colorado and Nebraska. Table 27B provides a summary of a proso millet foundation plot grown in 2019 in Chile and Colorado.

Tables 28-32 provide a trait data comparison between DLG149 and other known released check varieties. Table 28A provides a summary of average grain yield (lbs/ac) based on dry weight basis of variety DLG149 as compared to commercial proso millet cultivars grown at various Colorado and Nebraska locations from 2018 to 2020 in small yield plot trials planted as per Table 27A. Yield/acre was calculated using small plot trial data, adjusted for grain moisture. Table 28B provides a summary of average grain yield (lbs/ac) based on GPS adjusted mean (spatially variation adjustment) of variety DLG149 as compared to commercial proso millet cultivars grown at various Colorado and Nebraska locations from 2018-2020 in small yield plot trials planted as per Table 27A. Yield/acre was calculated using small plot trial data and adjusted for grain moisture. Table 28C provides a summary of average as-is grain yields (lbs/ac) of DLG149 and Huntsman from foundation plots grown in Colorado during 2019 planted as per Table 27B.

Table 29 provides a summary of average test weight (pounds per bushel) of DLG149 and commercial checks at various locations in Colorado and Nebraska in small yield plot trials grown from 2018 to 2020 planted as per Table 27A. Table 30 provides data for average heading date (days) of DLG149 and commercial checks (Dawn, Earlybird, Huntsman, Horizon, Plateau, Sunup) at Akron, CO and Sidney, NE in 2018 and 2020 small plot trials planted as per Table 27A. Table 31 provides data for average plant height (cm) of DLG149 and commercial checks (Dawn, Earlybird, Huntsman, Horizon, Plateau, Sunup) at Akron, CO and Sidney, NE locations in 2018 and 2020 small plot trials planted as per Table 27A. Table 32 provides the average 1000 grain weight (in grams) of DLG149 and commercial checks (Dawn, Earlybird, Huntsman, Horizon, Plateau, Sunup) in 2018 yield plot trials planted as per Table 27A.

TABLE 25

DLG149 Gilbert IA

| Sr. | Trait | DLG149 | Dawn | Earlybird | Horizon |
|---|---|---|---|---|---|
| 1 | Flag leaf attitude of blade | Semi erect | Semi erect | Semi erect | Semi erect |
| 2 | Flag leaf anthocyanin coloration | Absent | Absent | Absent | Absent |
| 3 | Flag leaf intensity of anthocyanin coloration | Absent | Absent | Absent | Absent |
| 4 | Flag leaf length (cm) | 28.8 | 23.4 | 27.9 | 27.8 |
| 5 | Flag leaf width (cm) | 2.12 | 1.78 | 1.83 | 2.86 |
| 6 | Number of internodes | 5 | 4 | 5 | 5 |
| 7 | Length of upper internode (cm) | 14.75 | 13.45 | 15.64 | 14.15 |
| 8 | Thickness of internodes (cm) | 0.57 | 0.45 | 0.67 | 0.69 |
| 9 | Time of panicle emergence (days) | 41 | 26 | 37 | 37 |
| 10 | Natural height (cm) | 102.66 | 78.8 | 106.32 | 99.03 |
| 11 | Angle of panicle branches | Very acute | Very acute | Very acute | Very acute |
| 12 | Panicle attitude | Semi erect | Semi erect | Semi erect | Semi erect |
| 13 | Panicle length, excluding peduncle (cm) | 21.29 | 19.38 | 22.1 | 21.35 |
| 14 | Panicle width(cm) | 4.75 | 4.82 | 5.45 | 4.49 |
| 15 | Panicle density | Dense | Dense | Dense | Dense |
| 16 | Degree of curvature of lateral branches | Weak | Weak | Weak | Weak |
| 17 | Number of pillows | None | None | None | None |
| 18 | Length of primary branches (cm) | 10.67 | 12.21 | 14.70 | 13.57 |
| 19 | Spikelet shape | Broad Elliptic | Broad Elliptic | Broad Elliptic | Broad Elliptic |
| 20 | Glume anthocyanin coloration | Absent | Absent | Absent | Absent |
| 21 | Stigma color | White | White | White | White |
| 22 | Grain size of spots | Large | Large | Large | Large |
| 23 | Grain shape | Broad Elliptic | Broad Elliptic | Broad Elliptic | Broad Elliptic |
| 24 | Grain color | White | White | White | White |
| 25 | Grain: presence of spotting/ridges | Absent | Absent | Absent | Absent |
| 26 | Grain: size of spots | Absent | Absent | Absent | Absent |
| 27 | Kernel (not polished) color | Light Yellow | Light Yellow | Light Yellow | Light Yellow |
| 28 | Kernel intensity of brown color of placental spot | Dark | Medium | Dark | Dark |
| 29 | Kernel: type of endosperm | Non-waxy | Non-waxy | Non-waxy | Non-waxy |

| Sr. | Trait | DLG149 | Huntsman | Plateau | Sunup |
|---|---|---|---|---|---|
| 1 | Flag leaf attitude of blade | Semi erect | Semi erect | Semi erect | Semi erect |
| 2 | Flag leaf anthocyanin coloration | Absent | Absent | Absent | Absent |
| 3 | Flag leaf intensity of anthocyanin coloration | Absent | Absent | Absent | Absent |
| 4 | Flag leaf length (cm) | 28.8 | 29.4 | 28.9 | 33.3 |
| 5 | Flag leaf width (cm) | 2.12 | 2.15 | 2.05 | 1.88 |
| 6 | Number of internodes | 5 | 5 | 5 | 5 |
| 7 | Length of upper internode (cm) | 14.75 | 14.75 | 13.30 | 14.24 |

TABLE 25-continued

| | DLG149 Gilbert IA | | | | |
|---|---|---|---|---|---|
| 8 | Thickness of internodes (cm) | 0.57 | 0.53 | 0.51 | 0.52 |
| 9 | Time of panicle emergence (days) | 41 | 36 | 29 | 38 |
| 10 | Natural height (cm) | 102.66 | 101.09 | 98.13 | 102.41 |
| 11 | Angle of panicle branches | Very acute | Very acute | Moderately acute | Very acute |
| 12 | Panicle attitude | Semi erect | Semi erect | Moderately dropping | Semi erect |
| 13 | Panicle length, excluding peduncle (cm) | 21.29 | 23.03 | 30.85 | 21.82 |
| 14 | Panicle width (cm) | 4.75 | 7.6 | 7.68 | 3.44 |
| 15 | Panicle density | Dense | Dense | Medium | Dense |
| 16 | Degree of curvature of lateral branches | Weak | Medium | Strong | Weak |
| 17 | Number of pillows | None | None | None | None |
| 18 | Length of primary branches (cm) | 10.67 | 14.09 | 19.77 | 13.69 |
| 19 | Spikelet shape | Broad Elliptic | Broad Elliptic | Broad Elliptic | Broad Elliptic |
| 20 | Glume anthocyanin coloration | Absent | Absent | Absent | Absent |
| 21 | Stigma color | White | White | White | White |
| 22 | Grain size of spots | Large | Large | Large | Large |
| 23 | Grain shape | Broad Elliptic | Broad Elliptic | Broad Elliptic | Broad Elliptic |
| 24 | Grain color | White | White | White | White |
| 25 | Grain: presence of spotting/ridges | Absent | Absent | Absent | Absent |
| 26 | Grain: size of spots | Absent | Absent | Absent | Absent |
| 27 | Kernel (not polished) color | Light Yellow | Light Yellow | Light Yellow | Light Yellow |
| 28 | Kernel intensity of brown color of placental spot | Dark | Medium | Dark | Dark |
| 29 | Kernel: type of endosperm | Non-waxy | Non-waxy | Waxy | Non-waxy |

TABLE 26

| | DLG149 Ventura IA | | | | |
|---|---|---|---|---|---|
| Sr. | Trait | DLG149 | Dawn | Earlybird | Horizon |
| 1 | Flag leaf attitude of blade | Semi erect | Semi erect | Semi erect | Semi erect |
| 2 | Flag leaf anthocyanin coloration | Absent | Absent | Absent | Absent |
| 3 | Flag leaf intensity of anthocyanin coloration | Absent | Absent | Absent | Absent |
| 4 | Flag leaf length (cm) | 26.45 | 21.8 | 31.4 | 32.6 |
| 5 | Flag leaf width (cm) | 1.67 | 1.75 | 2.24 | 2.27 |
| 6 | Number of internodes | 6 | 4 | 5 | 5 |
| 7 | Length of upper internode (cm) | 13.2 | 16.3 | 16.2 | 15.7 |
| 8 | Thickness of internodes (cm) | 0.47 | 0.40 | 0.54 | 0.52 |
| 9 | Time of panicle emergence (days) | 35 | 28 | 35 | 33 |
| 10 | Natural height (cm) | 115.00 | 78.08 | 102.70 | 99.63 |
| 11 | Angle of panicle branches | Very acute | Very acute | Very acute | Very acute |
| 12 | Panicle attitude | Semi erect | Semi erect | Semi erect | Semi erect |
| 13 | Panicle length, excluding peduncle (cm) | 22.41 | 17.81 | 22.46 | 22.42 |
| 14 | Panicle width (cm) | 4.54 | 3.58 | 6.62 | 6 |
| 15 | Panicle density | Dense | Dense | Dense | Dense |
| 16 | Degree of curvature of lateral branches | Weak | Weak | Weak | Weak |
| 17 | Number of pillows | None | None | None | None |
| 18 | Length of primary branches (cm) | 11.58 | 11.53 | 13.58 | 13.31 |
| 19 | Spikelet shape | Broad Elliptic | Broad Elliptical | Broad Elliptical | Broad Elliptical |
| 20 | Glume anthocyanin coloration | Absent | Absent | Absent | Absent |
| 21 | Stigma color | White | White | White | White |
| 22 | Grain size of spots | Large | Large | Large | Large |
| 23 | Grain shape | Broad Elliptic | Broad Elliptic | Broad Elliptic | Broad Elliptic |

TABLE 26-continued

DLG149 Ventura IA

| | | | | | |
|---|---|---|---|---|---|
| 24 | Grain color | White | White | White | White |
| 25 | Grain: presence of spotting/ridges | Absent | Absent | Absent | Absent |
| 26 | Grain: size of spots | Absent | Absent | Absent | Absent |
| 27 | Kernel (not polished) color | Light Yellow | Light Yellow | Light Yellow | Light Yellow |
| 28 | Kernel intensity of brown color of placental spot | Dark | Medium | Dark | Dark |
| 29 | Kernel: type of endosperm | Non-waxy | Non-waxy | Non-waxy | Non-waxy |

| Sr. | Trait | DLG149 | Huntsman | Plateau | Sunup |
|---|---|---|---|---|---|
| 1 | Flag leaf attitude of blade | Semi erect | Semi erect | Semi erect | Semi erect |
| 2 | Flag leaf anthocyanin coloration | Absent | Absent | Absent | Absent |
| 3 | Flag leaf intensity of anthocyanin coloration | Absent | Absent | Absent | Absent |
| 4 | Flag leaf length (cm) | 26.45 | 32.3 | 30.6 | 28.8 |
| 5 | Flag leaf width (cm) | 1.67 | 2.16 | 1.92 | 1.98 |
| 6 | Number of internodes | 6 | 5 | 5 | 5 |
| 7 | Length of upper internode (cm) | 13.2 | 16.4 | 15.0 | 17.1 |
| 8 | Thickness of internodes (cm) | 0.47 | 0.54 | 0.48 | 0.62 |
| 9 | Time of panicle emergence (days) | 35 | 36 | 30 | 35 |
| 10 | Natural height (cm) | 115.00 | 107.67 | 94.44 | 116.23 |
| 11 | Angle of panicle branches | Very acute | Very acute | Moderately acute | Very acute |
| 12 | Panicle attitude | Semi erect | Semi erect | Moderately dropping | Semi erect |
| 13 | Panicle length, excluding peduncle (cm) | 22.41 | 22.79 | 32.25 | 23.01 |
| 14 | Panicle width (cm) | 4.54 | 6.47 | 5.39 | 4.63 |
| 15 | Panicle density | Dense | Dense | Medium | Dense |
| 16 | Degree of curvature of lateral branches | Weak | Medium | Strong | Weak |
| 17 | Number of pillows | None | None | None | None |
| 18 | Length of primary branches (cm) | 11.58 | 13.71 | 19.07 | 13.74 |
| 19 | Spikelet shape | Broad Elliptic | Broad Elliptical | Broad Elliptical | Broad Elliptical |
| 20 | Glume anthocyanin coloration | Absent | Absent | Absent | Absent |
| 21 | Stigma color | White | White | White | White |
| 22 | Grain size of spots | Large | Large | Large | Large |
| 23 | Grain shape | Broad Elliptic | Broad Elliptic | Broad Elliptic | Broad Elliptic |
| 24 | Grain color | White | White | White | White |
| 25 | Grain: presence of spotting/ridges | Absent | Absent | Absent | Absent |
| 26 | Grain: size of spots | Absent | Absent | Absent | Absent |
| 27 | Kernel (not polished) color | Light Yellow | Light Yellow | Light Yellow | Light Yellow |
| 28 | Kernel intensity of brown color of placental spot | Dark | Medium | Dark | Dark |
| 29 | Kernel: type of endosperm | Non-waxy | Non-waxy | waxy | Non-waxy |

TABLE 27A

DLG149 small plot yield trials

| Year | Trial type | Location | Seed rate | Plot size | Rows spacing (inch) |
|---|---|---|---|---|---|
| 2018 | Small plot | Akron CO | 20 lbs/ac | 125 sq. ft | 10 |
| 2018 | Small plot | Burlington CO | 20 lbs/ac | 125 sq. ft | 8 |
| 2018 | Small plot | Sidney NE | 20 lbs/ac | 125 sq. ft | 10 |
| 2019 | Small plot | Burlington CO | 20 lbs/ac | 125 sq. ft | 8 |
| 2019 | Small plot | Fleming CO | 20 lbs/ac | 125 sq. ft | 8 |
| 2019 | Small plot | Sidney NE | 20 lbs/ac | 125 sq. ft | 10 |
| 2020 | Small plot | Burlington CO | 20 lbs/ac | 125 sq. ft | 8 |
| 2020 | Small plot | Sidney NE | 20 lbs/ac | 125 sq. ft | 10 |

TABLE 27B

DLG149 foundation plot

| Year | Plot type | Location | Seed rate | Plot size | Row spacing (inch) |
|---|---|---|---|---|---|
| 2019 | Foundation | Paine Chile | 20 lbs/ac | 0.25 acre | 12 |
| 2019 | Foundation | Matheson CO | 12 lbs/ac | 10 acres | 10 |

TABLE 28A

DLG149 average grain yield (lbs/ac dry weight)

| | 2018 | | | 2019 | | | 2020 | |
|---|---|---|---|---|---|---|---|---|
| Variety | Akron | Burlington | Sidney | Fleming | Burlington | Sidney | Burlington | Sidney |
| DLG149 | 1742 | 3729 | 1568 | 2694 | 2165 | 1115 | 582 | 1525 |
| Dawn | 1150 | 1568 | 725 | na | 1011 | 1011 | 892 | 1958 |
| Earlybird | 1324 | 3032 | 1307 | na | 1742 | 1454 | 770 | 1674 |
| Horizon | 1394 | 3101 | 1721 | na | 1429 | 1394 | 676 | 1536 |
| Huntsman | 1499 | 3136 | 1512 | 2195 | 1673 | 1429 | 753 | 1518 |
| Plateau | 488 | 2335 | 1349 | na | 1708 | 1289 | 627 | 1288 |
| Sunup | 1568 | 3554 | 1495 | na | 1812 | 1812 | 732 | 1539 |
| Mean | 1309 | 2922 | 1382 | 2444 | 1649 | 1358 | 719 | 1577 |

TABLE 28B

DLG149 average grain yield (lbs/ac GPS adjusted mean)

| | 2018 | | | 2019 | | | 2020 | |
|---|---|---|---|---|---|---|---|---|
| Variety | Akron | Burlington | Sidney | Fleming | Burlington | Sidney | Burlington | Sidney |
| DLG149 | 1951 | 4328 | 1715 | 2722 | 1882 | 1171 | 456 | 1635 |
| Dawn | 728 | 1896 | 896 | na | 1021 | 958 | 606 | 1826 |
| Earlybird | 1523 | 3628 | 1415 | na | 1777 | 1394 | 655 | 1565 |
| Horizon | 1620 | 3642 | 1896 | na | 1453 | 1282 | 700 | 1582 |
| Huntsman | 1760 | 3729 | 1666 | 2265 | 1652 | 1432 | 519 | 1641 |
| Plateau | 1261 | 2600 | 1537 | na | 1746 | 1195 | 446 | 1425 |
| Sunup | 1798 | 4203 | 1655 | na | 1889 | 1715 | 575 | 1516 |
| Mean | 1520 | 3432 | 1540 | 2494 | 1631 | 1307 | 565 | 1599 |

TABLE 28C

DLG149 average as-is grain yield (lbs/ac)

| Variety | 2019 Paine Chile | 2019 Matheson |
|---|---|---|
| DLG149 | 2168 | 1250 |
| Huntsman | Na | 1750 |

TABLE 29

DLG149 average test weight (pounds per bushel)

| Variety | 2018 Akron | 2018 Burlington | 2018 Sidney | 2019 Fleming | 2019 Burlington | 2019 Sidney | 2020 Burlington | 2020 Sidney |
|---|---|---|---|---|---|---|---|---|
| DLG149 | 52 | 55 | 53 | 51 | 53 | 48 | 39 | 47 |
| Dawn | na | 51 | na | na | 54 | 48 | 53 | 49 |
| Earlybird | 52 | 55 | 51 | na | 55 | 47 | 46 | 49 |
| Horizon | 54 | 53 | 54 | na | 54 | 50 | 42 | 49 |
| Huntsman | 48 | 54 | 54 | 54 | 54 | 48 | 45 | 49 |
| Plateau | na | 53 | 49 | na | 51 | 46 | 41 | 47 |
| Sunup | 52 | 55 | 51 | na | 55 | 50 | 47 | 48 |
| Mean | 52 | 54 | 52 | 53 | 54 | 48 | 45 | 48 |

TABLE 30

DLG149 average heading date (days)

| Variety | 2018 Akron | 2018 Sidney | 2020 Sidney |
|---|---|---|---|
| DLG149 | 46 | 45 | 49 |
| Dawn | 42 | 45 | 47 |
| Earlybird | 45 | 45 | 48 |
| Huntsman | 48 | 45 | 47 |
| Horizon | 46 | 45 | 49 |
| Plateau | 43 | 43 | 44 |
| Sunup | 47 | 46 | 50 |
| Mean | 45 | 45 | 48 |

TABLE 31

DLG149 average plant height (cm)

| Variety | 2018 Akron | 2018 Sidney | 2020 Sidney |
|---|---|---|---|
| DLG149 | 61.97 | 104.39 | 43.18 |
| Dawn | 51.82 | 61.98 | 43.18 |
| Earlybird | 62.99 | 107.70 | 43.18 |
| Huntsman | 68.07 | 102.62 | 43.18 |
| Horizon | 59.94 | 96.52 | 43.18 |
| Plateau | 77.22 | 105.66 | 45.72 |
| Sunup | 67.06 | 106.68 | 45.72 |
| Mean | 64.15 | 97.94 | 43.91 |

TABLE 32

DLG149 average 1000 grain weight (in grams)

| Line name | 2018 Burlington | 2018 Sidney | 2020 Burlington | 2020 Sidney |
|---|---|---|---|---|
| DLG149 | 7.7 | 7.5 | 6.1 | 5.8 |
| Dawn | 6.4 | 7.1 | 5.6 | 5.8 |
| Earlybird | 7.1 | 7.0 | 5.8 | 6.1 |
| Huntsman | 7.5 | 7.3 | 6.0 | 5.9 |
| Horizon | 7.9 | 7.0 | 6.2 | 6.2 |
| Plateau | 5.8 | 6.2 | 5.4 | 5.4 |
| Sunup | 7.8 | 7.1 | 6.6 | 6.4 |
| Mean | 7.1 | 7.0 | 5.9 | 5.9 |

Genotypic Characteristics

The genotypic characteristics of the higher-yielding Proso varieties are summarized in a table of single nucleotide polymorphisms (SNPs) entitled "Proso_SNP_Table.txt" that is available in electronic form from the USPTO web site. An electronic copy of the table will also be available from the USPTO upon request and payment of the fee set forth in 37 CFR 1.19 (b) (3).

In the table provided in the file "Proso_SNP_table.txt", SNP data are provided for the DLG240, DLG40, DLG148, and DLG149 varieties described herein. The first column of the table indicates the *Panicum miliaceum* chromosome number (1 through 18, indicated by "PmChr01" through "PmChr18") on which the SNP is located. The *Panicum miliaceum* chromosome nucleotide sequences are provided by the Zou *Panicum miliaceum* reference sequence (Zou (2019) "The genome of broomcorn millet" Nature Communications 10:436, incorporated herein by reference). Accession numbers for the reference nucleotide sequences for each chromosome are provided in Table 33.

TABLE 33

Reference Proso genome sequence accession numbers

| Proso sequence | NCBI accession |
|---|---|
| Chromosome 1 | CM009690.2 |
| Chromosome 2 | CM009691.2 |
| Chromosome 3 | CM009692.2 |
| Chromosome 4 | CM009693.2 |
| Chromosome 5 | CM009694.2 |
| Chromosome 6 | CM009695.2 |

TABLE 33-continued

Reference Proso genome sequence accession numbers

| Proso sequence | NCBI accession |
| --- | --- |
| Chromosome 7 | CM009696.2 |
| Chromosome 8 | CM009697.2 |
| Chromosome 9 | CM009698.2 |
| Chromosome 10 | CM009699.2 |
| Chromosome 11 | CM009700.2 |
| Chromosome 12 | CM009701.2 |
| Chromosome 13 | CM009702.2 |
| Chromosome 14 | CM009703.2 |
| Chromosome 15 | CM009704.2 |
| Chromosome 16 | CM009705.2 |
| Chromosome 17 | CM009706.2 |
| Chromosome 18 | CM009707.2 |
| Chloroplast | CM009689.1 |

The second column provides the nucleotide position within the reference chromosome nucleotide sequence where the SNP is located. Nucleotide position within the chromosomal nucleotide sequences use the numbering according to the Zou reference nucleotide sequence. The third column lists the nucleotide base of the SNP allele present in the reference sequence at the nucleotide position indicated in the second column. The fourth column lists the nucleotide base present for the alternative SNP allele that differs from the reference sequence at the nucleotide position indicated in the second column. The fifth through eighth columns indicate for each Proso variety described herein (DLG148, DLG149, DLG240, and DLG40, respectively) that the variety has a nucleotide sequence with the reference SNP allele or the alternative allele at the indicated SNP position of the second column. For each Proso variety, an "A" indicates a polymorphic position where the Proso variety carries the reference allele and a "B" indicates a polymorphic position where the Proso variety carries the alternate allele. For example, the table indicates that the DLG148 variety carries the alternative SNP allele (indicated by a "B") at position 56678 in chromosome 1 ("PmChr1"). In particular, the table indicates that the DLG148 variety has an adenine base at nucleotide position 56678 in chromosome 1 where the reference sequence has a guanine at nucleotide position 56678 in chromosome 1.

All publications and patents mentioned in the above specification are incorporated herein by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

We claim:

1. A plant of Proso cultivar DLG40, representative seed of said Proso cultivar having been deposited under ATCC Accession No. PTA. 127821.

2. A seed that produces the plant of claim 1.

3. A cell of the plant of claim 1.

4. A tissue culture of regenerable cells comprising the cell of claim 3.

5. A method of Proso breeding, said method comprising crossing the plant of claim 1 with itself or a second Proso plant to produce Proso seed.

6. The method of claim 5, further comprising crossing a plant of Proso cultivar DLG40 with a second Proso plant of a different genotype to produce hybrid Proso seed.

7. An $F_1$ hybrid Proso seed produced by the method of claim 6.

8. A method of introducing a locus conversion into a Proso plant, said method comprising: (a) crossing a plant of Proso cultivar DLG40 with a second plant comprising a desired locus to produce $F_1$ progeny plants, representative seed of said Proso cultivar DLG40 having been deposited under ATCC Accession No. PTA-127821; (b) selecting at least a first progeny plant from step (a) that comprises the locus to produce a selected progeny plant; (c) crossing the selected progeny plant from step (b) with a plant of Proso cultivar DLG40 to produce at least a first backcross progeny plant that comprises the locus; and (d) repeating steps (b) and (c) with the first backcross progeny plant produced from step (c) used in place of the first progeny plant of step (b) during said repeating, wherein steps (b) and (c) are repeated until at least a backcross progeny plant is produced comprising the locus conversion.

9. The method of claim 8, wherein the locus confers a trait selected from the group consisting of male sterility, herbicide tolerance, insect or pest resistance, disease resistance, modified fatty acid metabolism, altered water efficiency, altered nitrogen efficiency, altered protein quantity, modified protein composition, altered oil quantity, modified oil composition, altered starch quantity, modified starch composition, abiotic stress resistance, and modified carbohydrate metabolism.

10. A Proso plant of Proso cultivar DLG40, further comprising a locus conversion, wherein the plant comprises the locus conversion and otherwise comprises all of the morphological and physiological characteristics of Proso cultivar DLG40, representative seed of Proso cultivar DLG40 having been deposited under ATCC Accession No. PTA-127821.

11. The method of claim 6, wherein the method further comprises: (a) crossing a plant grown from said hybrid Proso seed with itself or a different Proso plant to produce a seed of a progeny plant of a subsequent generation.

12. The method of claim 11, wherein the method further comprises: (b) growing a progeny plant of a subsequent generation from said seed of a progeny plant of a subsequent generation and crossing the progeny plant of a subsequent generation with itself or a second plant to produce a progeny plant of a further subsequent generation.

13. The method of claim 12, wherein the method further comprises: (c) repeating steps (a) and (b) using said progeny plant of a further subsequent generation from step (b) in place of the plant grown from said hybrid Proso seed in step (a), wherein steps (a) and (b) are repeated with sufficient inbreeding to produce an inbred Proso plant derived from the Proso cultivar DLG40.

14. A method of introducing a mutation into the genome of Proso cultivar DLG40, said method comprising applying a mutagen to the plant of claim 1, or a part thereof, wherein the resulting plant comprises a genome mutation.

15. A method of producing a commodity plant product, said method comprising obtaining the plant of claim 1 or a part thereof and producing said commodity plant product therefrom.

16. The method of claim 15, wherein the commodity plant product is seed, meal, flour, protein, or oil.

\* \* \* \* \*

UNITED STATES PATENT AND TRADEMARK OFFICE
CERTIFICATE OF CORRECTION

| | |
|---|---|
| PATENT NO. | : 12,336,472 B2 |
| APPLICATION NO. | : 18/441777 |
| DATED | : June 24, 2025 |
| INVENTOR(S) | : Patrick S. Schnable, James C. Schnable and Santosh Rajput |

Page 1 of 1

It is certified that error appears in the above-identified patent and that said Letters Patent is hereby corrected as shown below:

In the Claims

Claim 1, Column 73, Line 63 reads:
"Accession No. PTA. 127821"
Whereas it should read:
"Accession No. PTA-127821".

Signed and Sealed this
Nineteenth Day of August, 2025

Coke Morgan Stewart
*Acting Director of the United States Patent and Trademark Office*